(12) United States Patent
Braathen et al.

(10) Patent No.: US 12,268,736 B2
(45) Date of Patent: Apr. 8, 2025

(54) VACCINE MOLECULES

(71) Applicant: University of Oslo, Oslo (NO)

(72) Inventors: Ranveig Braathen, Oslo (NO); Bjarne Bogen, Oslo (NO)

(73) Assignee: University of Oslo, Oslo (NO)

( * ) Notice: Subject to any disclaimer, the term of this patent is extended or adjusted under 35 U.S.C. 154(b) by 760 days.

(21) Appl. No.: 16/645,140

(22) PCT Filed: Sep. 7, 2018

(86) PCT No.: PCT/IB2018/001119
§ 371 (c)(1),
(2) Date: Mar. 6, 2020

(87) PCT Pub. No.: WO2019/048928
PCT Pub. Date: Mar. 14, 2019

(65) Prior Publication Data
US 2022/0118076 A1     Apr. 21, 2022

Related U.S. Application Data

(60) Provisional application No. 62/555,305, filed on Sep. 7, 2017.

(51) Int. Cl.
*A61K 39/145*     (2006.01)
*A61K 39/00*     (2006.01)
*A61P 31/16*     (2006.01)

(52) U.S. Cl.
CPC ........ *A61K 39/145* (2013.01); *A61K 39/0011* (2013.01); *A61P 31/16* (2018.01); *A61K 2039/53* (2013.01); *A61K 2039/6056* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,596,556 A | 6/1986 | Morrow et al. |
| 4,675,189 A | 6/1987 | Kent et al. |
| 5,057,540 A | 10/1991 | Kensil et al. |
| 5,075,109 A | 12/1991 | Tice et al. |
| 5,133,974 A | 7/1992 | Paradissis et al. |
| 5,284,656 A | 2/1994 | Platz et al. |
| 5,407,686 A | 4/1995 | Patel et al. |
| 5,451,569 A | 9/1995 | Wong et al. |
| 5,736,152 A | 4/1998 | Dunn |
| 5,993,412 A | 11/1999 | Deily et al. |
| 6,005,099 A | 12/1999 | Davies et al. |
| 6,651,655 B1 | 11/2003 | Licalsi et al. |
| 8,932,603 B2 | 1/2015 | Bogen et al. |
| 2005/0238660 A1 | 10/2005 | Babiuk et al. |
| 2005/0281843 A1 | 12/2005 | Singh et al. |
| 2016/0031991 A1* | 2/2016 | Brekke ............... C07K 14/005 435/69.3 |

FOREIGN PATENT DOCUMENTS

| | | |
|---|---|---|
| EP | 0468520 | 1/1992 |
| EP | 0517565 | 5/1992 |
| EP | 0362279 | 1/1995 |
| EP | 0549074 | 1/1999 |
| EP | 0729473 | 8/2000 |
| EP | 0689454 | 2/2005 |
| EP | 1599504 | 3/2014 |
| WO | WO 92/19265 | 11/1992 |
| WO | WO 93/13202 | 7/1993 |
| WO | WO 94/00153 | 1/1994 |
| WO | WO 95/17210 | 6/1995 |
| WO | WO 96/11711 | 1/1996 |
| WO | WO 96/02555 | 2/1996 |
| WO | WO 96/33739 | 10/1996 |
| WO | WO 97/48440 | 12/1997 |
| WO | WO 98/16247 | 4/1998 |
| WO | WO 98/20734 | 5/1998 |
| WO | WO 98/28037 | 7/1998 |
| WO | WO 98/56414 | 12/1998 |
| WO | WO 99/10008 | 3/1999 |
| WO | WO 99/11241 | 3/1999 |
| WO | WO 99/12565 | 3/1999 |
| WO | WO 99/27961 | 6/1999 |
| WO | WO 2004/076489 | 9/2004 |
| WO | WO 2011/034605 | 3/2011 |
| WO | WO 2013/092875 | 6/2013 |

OTHER PUBLICATIONS

Spang et al., Heterodimeric Barnase-Barstar Vaccine Molecules: Influence of One versus Two Targeting Units Specific for Antigen Presenting Cells, 2012, PLoS One, vol. 7, No

(56) References Cited

OTHER PUBLICATIONS

Anderson et al., Simultaneous Targeting of Multiple Hemagglutinins to APCs for Induction of Broad Immunity against Influenza. J Immunol. Mar. 15, 2018;200(6):2057-2066.
Baier et al., Immunogenic targeting of recombinant peptide vaccines to human antigen-presenting cells by chimeric anti-HLA-DR and anti-surface immunoglobulin D antibody Fab fragments in vitro. J Virol. Apr. 1995;69(4):2357-65.
Braquet et al., Effect of endothelin-1 on blood pressure and bronchopulmonary system of the guinea pig. J Cardiovasc Pharmacol. 1989;13 Suppl 5:S143.
Brazolot-Millan et al., CpG DNA can induce strong Th1 humoral and cell-mediated immune responses against hepatitis B surface antigen in young mice. Proc Natl Acad Sci U S A. Dec. 22, 1998;95(26):15553-8.
Busch et al., Stabilization of soluble, low-affinity HLA-DM/HLA-DR1 complexes by leucine zippers. J Immunol Methods. May 1, 2002;263(1-2):111-21.
Castro et al., CD11c provides an effective immunotarget for the generation of both CD4 and CD8 T cell responses. Eur J Immunol. Aug. 2008;38(8):2263-73.
Davis et al., CpG DNA is a potent enhancer of specific immunity in mice immunized with recombinant hepatitis B surface antigen. J Immunol. Jan. 15, 1998;160(2):870-6.
Debs et al., Lung-Specific delivery of cytokines induces sustained pulmonary and systemic immunomodulation in rats. J. Immunol. 1988; 140:3482-3488.
Demangel et al., Single chain antibody fragments for the selective targeting of antigens to dendritic cells. Mol Immunol. May 2005;42(8):979-85.
Fredriksen et al., Chemokine-idiotype fusion DNA vaccines are potentiated by bivalency and xenogeneic sequences. Blood. Sep. 15, 2007;110(6):1797-805.
Fredriksen et al., DNA vaccines increase immunogenicity of idiotypic tumor antigen by targeting novel fusion proteins to antigen-presenting cells. Mol Ther. Apr. 2006;13(4):776-85.
Fredriksen et al., Targeted DNA vaccines for enhanced induction of idiotype-specific B and T cells. Front Oncol. Oct. 30, 2012;2:154.
Grodeland et al., DNA vaccine that targets hemagglutinin to MHC class II molecules rapidly induces antibody-mediated protection against influenza. J Immunol. Sep. 15, 2013;191(6):3221-31.
Grodeland et al., The specificity of targeted vaccines for APC surface molecules influences the immune response phenotype. PLoS One. Nov. 11, 2013;8(11):e80008. 11 pages.
Guyre et al., Increased potency of Fc-receptor-targeted antigens. Cancer Immunol Immunother. Nov.-Dec. 1997;45(3-4):146-8.
Hawiger et al., Dendritic cells induce peripheral T cell unresponsiveness under steady state conditions in vivo. J Exp Med. Sep. 17, 2001;194(6):769-79.
Hilgers et al., Synergistic effects of synthetic adjuvants on the humoral immune response. Int Arch Allergy Appl Immunol. 1986;79(4):392-6.
Hilgers et al., Synthetic sulpholipopolysaccharides: novel adjuvants for humoral immune responses. Immunology. Jan. 1987;60(1):141-6.
Hofgaard et al., A novel mouse model for multiple myeloma (MOPC315.BM) that allows noninvasive spatiotemporal detection of osteolytic disease. PLoS One. 2012;7(12):e51892. 13 pages.
Hubbard et al., Anti-neutrophil-elastase defenses of the lower respiratory tract in alpha 1-antitrypsin deficiency directly augmented with an aerosol of alpha 1-antitrypsin. Ann Intern Med. Aug. 1, 1989;111(3):206-12.

Illum et al., Hyaluronic acid ester microspheres as a nasal delivery system for insulin. J. Controlled Rel., 1994, 29:133-141.
Itoh et al., In vitro and in vivo characterization of new swine-origin H1N1 influenza viruses. Nature. Aug. 20, 2009;460(7258):1021-5.
Kensil et al., Separation and characterization of saponins with adjuvant activity from Quillaja saponaria Molina cortex. J Immunol. Jan. 15, 1991;146(2):431-7.
Kensil, Saponins as vaccine adjuvants. Crit Rev Ther Drug Carrier Syst. 1996;13(1-2):1-55.
Lacaille-Dubois et al., A review of the biological and pharmacological activities of saponins. Phytomedicine. Mar. 1996;2(4):363-86.
Liu et al., Recruitment of antigen-presenting cells to the site of inoculation and augmentation of human immunodeficiency virus type 1 DNA vaccine immunogenicity by in vivo electroporation. J Virol. Jun. 2008;82(11):5643-9.
Lunde et al., Antibodies engineered with IgD specificity efficiently deliver integrated T-cell epitopes for antigen presentation by B cells. Nat Biotechnol. Jul. 1999;17(7):670-5.
McCluskie et al., CpG DNA is a potent enhancer of systemic and mucosal immune responses against hepatitis B surface antigen with intranasal administration to mice. J Immunol. Nov. 1, 1998;161(9):4463-6.
Mestecky, The common mucosal immune system and current strategies for induction of immune responses in external secretions. J Clin Immunol. Jul. 1987;7(4):265-76.
Moll et al., Designed heterodimerizing leucine zippers with a ranger of pIs and stabilities up to 10(-15) M. Protein Sci. Mar. 2001;10(3):649-55.
Nchinda et al., The efficacy of DNA vaccination is enhanced in mice by targeting the encoded protein to dendritic cells. J Clin Invest. Apr. 2008;118(4):1427-36.
Neumann et al., Emergence and pandemic potential of swine-origin H1N1 influenza virus. Nature. Jun. 18, 2009;459(7249):931-9.
Norderhaug et al., Versatile vectors for transient and stable expression of recombinant antibody molecules in mammalian cells. J Immunol Methods. May 12, 1997;204(1):77-87.
Oeswein, et al. "Aerosolization of Proteins", 1990; Proceedings of Symposium on Respiratory Drug Delivery II Keystone, Colorado. 34 pages.
Powell et al., Vaccine Design—the Subunit and Adjuvant Approach, Plenum Press, New York, 1995. TOC only. 42 pages.
Ruffini et al., Genetic fusions with viral chemokines target delivery of nonimmunogenic antigen to trigger antitumor immunity independent of chemotaxis. J Leukoc Biol. Jul. 2004;76(1):77-85.
Schjetne et al., Delivery of antigen to CD40 induces protective immune responses against tumors. J Immunol. Apr. 1, 2007;178(7):4169-76.
Smith et al. Pulmonary deposition and clearance of aerosolized alpha-1-proteinase inhibitor administered to dogs and to sheep. J Clin Invest. Oct. 1989;84(4):1145-54.
Spang et al., Heterodimeric barnase-barstar vaccine molecules: influence of one versus two targeting units specific for antigen presenting cells. PLoS One. 2012;7(9):e45393. 10 pages.
Xie et al., A new format of bispecific antibody: highly efficient heterodimerization, expression and tumor cell lysis. J Immunol Methods. Jan. 2005;296(1-2):95-101.
Zapata et al., Engineering linear F(ab')2 fragments for efficient production in *Escherichia coli* and enhanced antiproliferative activity. Protein Eng. Oct. 1995;8(10):1057-62.

\* cited by examiner

FIG. 18

VACCINE MOLECULES

FIELD OF INVENTION

Provided herein is technology relating to vaccines and particularly, but not exclusively, to compositions, methods, and uses of heterodimer vaccine molecules formed from monomers comprising a variant targeting unit and a variant antigenic unit joined by heterodimerization units.

BACKGROUND

Influenza A viruses circulate among human populations engender significant morbidity and mortality. Most inactivated and live-attenuated vaccines against seasonal and pandemic influenza are strain specific, requiring constant updating of the strains used in yearly multivalent vaccine preparations. In addition, zoonotic infections, against which there is an absence of immunity in the human population, occasionally result in the emergence of pandemic strains [1], like the swine flu in 2009 [2]. Human infections by avian H5N1 and H7N9 viruses further highlight the potential risk posed by animal reservoirs of influenza A viruses. Thus, there is an urgent need for an influenza vaccine inducing broadly neutralizing antibodies towards optimally all serotypes of influenza.

A well-known method to increase the immunogenicity of protein antigens in subunit vaccines is to chemically [3-5] or genetically [6-9] incorporate the antigen into antibodies or antibody fragments that target antigen presenting cells (APC). This principle has been extended to DNA vaccination by constructing DNA plasmids that encode for APC-specific fusion proteins. Thus, cells transfected in vivo by DNA vaccination secrete fusion proteins that enhance delivery of antigen to APC, resulting in improved immune responses [10-14]. Electroporation of the injection site of the DNA vaccine ensure efficient uptake and translation into vaccine protein [12]. To increase the immunogenicity even further, Bogen and coworkers have developed a dimeric targeted DNA vaccine [12, 13]. The dimeric version containing two targeting units and two antigenic units increased the avidity. This bivalency in combination with xenogenic sequences found in this homodimeric vaccine increased the antibody responses than for monomeric equivalents in short term assays [15].

SUMMARY

Provided herein is technology relating to vaccines and particularly, but not exclusively, to compositions, methods, and uses of heterodimer vaccine molecules formed from monomers comprising a variant targeting unit and a variant antigenic unit joined by heterodimerization units.

Accordingly, in some embodiments the present invention provides a DNA vaccine comprising first and second nucleic acid constructs encoding first and second fusion proteins comprising a targeting unit, a heterodimerization unit, and an antigenic unit in operable association, wherein the antigenic unit for each of the first and second fusion proteins are variant target antigenic proteins and wherein when the first and second nucleic acid constructs are introduced into a cell the first and second fusion proteins are expressed and associate to form a first heterodimeric protein via association of the heterodimerization units.

In some embodiments, the heterodimerization unit in one of the first and second nucleic acid constructs is an ACID heterodimerization unit and the heterodimerization unit in the other of the first and second nucleic acid constructs is a BASE heterodimerization unit that interact to form an ACID/BASE heterodimerization domain is the first heterodimeric protein. In some embodiments, the heterodimerization unit in one of the first and second nucleic acid constructs is a barstar heterodimerization unit and the heterodimerization unit in the other of the first and second nucleic acid constructs is a barnase heterodimerization unit that interact to form an barstar/barnase heterodimerization domain is the first heterodimeric protein.

In some embodiments, the targeting units of the first and second fusion proteins are identical. In some embodiments, the targeting units of the first and second fusion proteins are different. In some embodiments, the targeting unit is an antigen binding protein. In some embodiments, the antigen binding protein is a scFv. In some embodiments, the targeting unit is an Antigen Presenting Cell (APC) targeting unit. In some embodiments, the APC targeting unit binds to a target selected from the group consisting of MHC-II molecules, CD40, CD11c, CD14, HLA-DP, Toll-like receptors, and chemokine receptors.

In some embodiments, the variant antigenic target proteins have greater than about 30%, 40%, 50%, 60%, 70%, 80%, 90% or 95% sequence identity or conserved regions of more than 8, 10, 12, 15, 20, 30, 40, 50 or 60 amino acids in length and up to 100 to 200 amino acids in length within the variant antigenic target proteins have greater than about 30%, 40%, 50%, 60%, 70%, 80%, 90% or 95% sequence identity. In some embodiments, the different variant antigenic target proteins are from different strains or serotypes of an organism. In some embodiments, the organism is a pathogenic organism. In some embodiments, the organism is selected from the group consisting of a virus, a bacterium, a fungus and a protozoan. In some embodiments, the different variant antigenic target proteins are variants of hemagglutinin (HA). In some embodiments, the vaccine comprises variants of HA from at least three, four, five or six and up to 12 or 18 strains or serotypes of influenza viruses. In some embodiments, the influenza viruses are selected from the group consisting of group 1 and group 2 influenza viruses. In some embodiments, the group 1 influenza viruses are selected from the group consisting of H1, H2, H5, H6, H8, H9, H11, H12, H13, H16, H17 and H18 and the group 2 influenza viruses are selected from the group consisting of H3, H4, H7, H10, H14 and H15. In some embodiments, the different variant antigenic target proteins are variants of a cancer antigen (e.g., neo-epitope).

In some embodiments, the DNA vaccine further comprises at least third and fourth nucleic acid constructs encoding third and fourth fusion proteins comprising a targeting unit, a heterodimerization domain, and an antigenic unit in operable association, wherein the antigenic unit for each of the third and fourth fusion proteins are variant target antigenic proteins. In some embodiments, expression of the third and fourth fusion proteins in a cell with the first and second fusion proteins results in the production of a mixture of heterodimeric proteins. In some embodiments, when the first and second nucleic acid constructs are expressed in a cell, the production of the heterodimeric proteins is characterized by the substantial absence of the production of homodimeric proteins comprising the same target antigenic protein. In some embodiments, when the first and second nucleic acid constructs and the at least third and fourth nucleic acid constructs are expressed in a cell, the production of the heterodimeric proteins is characterized by the substantial absence of the production of homodimeric proteins comprising the same target antigenic protein.

In some embodiments, the sequence encoding the fusion protein is operably linked to a promoter, preferably an exogenous promoter.

In some embodiments, the present invention provides vaccine compositions comprising a heterodimeric protein molecule, wherein the heterodimeric protein molecule comprises first and second fusion protein monomers comprising a targeting unit, a heterodimerization unit, and an antigenic unit in operable association, wherein the antigenic unit for each of the first and second fusion protein monomers differ by encoding different variant target antigenic proteins, and wherein the heterodimeric protein molecule comprises two of the monomers joined by association of the dimerization domains.

In some embodiments, the heterodimerization unit in one of the first and second fusion protein monomers is an ACID heterodimerization unit and the heterodimerization unit in the other of the first and second fusion protein monomers is a BASE heterodimerization unit that interact to form an ACID/BASE heterodimerization domain is the first heterodimeric protein. In some embodiments, the heterodimerization unit in one of the first and second fusion protein monomers is a barstar heterodimerization unit and the heterodimerization unit in the other of the first and second fusion protein monomers is a barnase heterodimerization unit that interact to form a barstar/barnase heterodimerization domain is the first heterodimeric protein. In some embodiments, the targeting units of the first and second fusion proteins are identical. In some embodiments, the targeting units of the first and second fusion proteins are different. In some embodiments, the targeting unit is an antigen binding protein. In some embodiments, the antigen binding protein is a scFv. In some embodiments, the targeting unit is an Antigen Presenting Cell (APC) targeting unit. In some embodiments, the APC targeting unit binds to a target selected from the group consisting of MHC-II molecules, CD40, CD11c, CD14, HLA-DP, Toll-like receptors, and chemokine receptors.

In some embodiments, the different variant antigenic target proteins have greater than about 30%, 40%, 50%, 60%, 70%, 80%, 90% or 95% sequence identity or conserved regions of more than 8, 10, 12, 15, 20, 30, 40, 50 or 60 amino acids in length and up to 100 to 200 amino acids in length within the variant antigenic target proteins have greater than about 30%, 40%, 50%, 60%, 70%, 80%, 90% or 95% sequence identity. In some embodiments, the different variant antigenic target proteins are from different strains or serotypes of an organism. In some embodiments, the organism is a pathogenic organism. In some embodiments, the organism is selected from the group consisting of a virus, a bacterium, a fungus and a protozoan. In some embodiments, the different variant antigenic target proteins are variants of hemagglutinin (HA). In some embodiments, the vaccine comprises variants of HA from at least three, four, five or six and up to 12 or 18 strains or serotypes of influenza viruses. In some embodiments, the influenza viruses are selected from the group consisting of group 1 and group 2 influenza viruses. In some embodiments, the group 1 influenza viruses are selected from the group consisting of H1, H2, H5, H6, H8, H9, H11, H12, H13, H16, H17 and H18 and the group 2 influenza viruses are selected from the group consisting of H3, H4, H7, H10, H14 and H15. In some embodiments, the different variant antigenic target proteins are variants of a cancer antigen.

In some embodiments, the vaccine compositions further comprise at least third and fourth fusion protein monomers comprising a targeting unit, a heterodimerization domain, and an antigenic unit in operable association, wherein the antigenic units for each of the third and fourth fusion protein monomers differ by encoding different versions of the variant target antigenic protein. In some embodiments, the vaccine comprises a mixture of heterodimeric proteins characterized in having all possible combinations of the first and second and at least third and fourth monomers. In some embodiments, the vaccine composition is characterized by the substantial absence of homodimeric proteins comprising the same target antigenic protein. In some embodiments, the vaccine composition is characterized by the substantial absence of homodimeric proteins comprising the same target antigenic protein.

In some embodiments, the present invention provides a pharmaceutical formulation comprising the DNA vaccine or vaccine composition as described above and a pharmaceutically acceptable carrier.

In some embodiments, the present invention provides a vaccine formulation comprising a vaccine composition as described above and an adjuvant.

In some embodiments, the present invention provides a method of immunizing or inducing an immune response to variant target antigenic proteins in a subject comprising administering to the subject a DNA vaccine, vaccine composition, pharmaceutical formulation or vaccine formulation as described above to a subject. In some embodiments, the method further comprises a second administration to the subject of a DNA vaccine, vaccine composition, pharmaceutical formulation or vaccine formulation as described above. In some embodiments, the method further comprises administering to the subject a second DNA vaccine, vaccine composition, pharmaceutical formulation or vaccine formulation comprising one or more non-targeted variant target antigenic protein subunits.

In some embodiments, the present invention provides for use of a DNA vaccine, vaccine composition, pharmaceutical formulation or vaccine formulation as described above to immunize or induce an immune response in a subject in need thereof.

In some embodiments, the present invention provides for use of a DNA vaccine, vaccine composition, pharmaceutical formulation or vaccine formulation as described above as a vaccine to prevent or to treat infection by a pathogen.

In some embodiments, the present invention provides for use of a DNA vaccine, vaccine composition, pharmaceutical formulation or vaccine formulation as described above as a vaccine to prevent or to treat cancer.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIGS. 1A-E provide schematics and data related heterodimeric vaccine moelcules of the present invention. A. The homodimeric targeting vaccine molecule is formed by two identical chains consisting of a targeting unit binding specific binding to APC, a dimerization unit connecting the targeting to the antigen and finally the antigenic unit. The dimerization unit consists of a shorten hinge and CH3 from human IgG3 inducing disulfide bridges and noncovalent interactions between the two chains. B. The ACID (A)/ BASE (B) motif from a modified leucine zipper subcloned with targeting units N-terminal and antigens C-terminal, inducing formation of heterodimers. C. The Barnase (Bn) and Barstar (Bs) subcloned with targeting units N-terminal and antigens C-terminal. In addition hl from the hinge in human IgG3 is added to the N-terminal of both barnase and barstar inducing stabilizing disulfidebridges. Interaction between the barnase-barstar protein pair induces heterodimers. D. Schematic depiction of gene constructs. E. ELISA results.

FIGS. 2A-D provide data related to expression of heterodimeric vaccine molecules of the present invention. A. All ACID/BASE heterodimers are secreted at similar leves as the homodimeric. B. The barnase-barstar heterodimers are also expressed but may be at some reduced levels compared to the homodimeric vaccine molecules. C and D. The same supernatants were analyzed in an ELISA measuring heterodimeric molecules from ACID/BASE and barnase-barstar heterodimeric pair. MIP1α-scFv315 is the positive control of the ELISA.

FIGS. 3A-B present schematics and data related to formation of heterodimeric vaccine molecules of the present invention. A. Schematic showing heterodimers expressing both OVA and mCherry as antigens and with either two XCL-1, two scFv$^{antiNIP}$ or one of each as targeting units. B. The ELISA detects only fusionproteins containing both XCL-1 and mCherry. Results: Fusionprotein of only ACID or BASE are equally expressed by HEK293 cells as well as heterodimers of ACID/BASE. OVA as well as mCherry can be antigen both on ACID and BASE, and similarly, the XCL-1 and scFv$^{antiNIP}$ can be expressed as targeting units of both ACID and BASE.

FIGS. 4A-D present data related to vaccine molecules of the present invention with different antigenic units. A. The ACID/BASE heterodimers subcloned to have monovalent targeting of both MIP-1a and scFvantiNIP expressing various antigens like ESAT (E), 85b (Tuberculosis antigens), scFvantiM315 and hemagglutinin (HA). The secreted proteins were detected in an ELISA specific for heterodimers, as only heterodimers expressing both antiNIP and MIP-1$^α$ is detected. B. The same supernatants were also analyzed with specific antibodies against HA. C. The ACID/BASE heterodimers subcloned to have monovalent targeting of both MIP-1α or XCL-1 and scFvantiNIP expressing various antigens like ESAT (E), 85b (Tuberculosis antigens), scFv$^{antiM315}$ and hemagglutinin (HA), and D. OVA, mCherry or scFv$^{antiM315}$ (F). The secreted proteins were detected in an ELISA specific for heterodimers as the coat is with mAb towards the ACID/BASE dimer.

FIGS. 5A-B present data related to the retention of chemotactic activity of an MIP1a targeting unit.

FIGS. 6A-B present data showing ACID/BASE heterodimer induce antigen specific responses in vivo after vaccination in BALB/c mice.

FIG. 7 presents data showing that an ACID/BASE heterodimer of the present invention induced protection against MOPC315 tumor cells after one vaccination.

FIGS. 8A-E present data relevant to design and characterization of heterodimeric vaccine molecules. A. Schematic demonstration of heterodimeric vaccine proteins. B. Schematic depiction of DNA cassettes for vaccine molecules of the present invention. C. ELISA analysis of heterodimeric molecules. D. Western blot of heterodimeric vaccine molecules. E. Flow cytometry of heterodimeric proteins molecules specific binding to targeted receptor (I-Ed/MHCII) expressed by fibroblasts.

FIGS. 9A-I present data showing bivalency of heterodimeric vaccine molecules increases IgG titers in mice. A.-I. ELISA results for mice vaccinated with vaccine constructs of the present invention.

FIGS. 10A-E present data showing antibody titers after vaccination with heterodimeric anti-tumor vaccines. A. Schematic of heterodimeric DNA vaccines with anti-tumor antigens. B-E. ELISA results for immune response following vaccination in mice.

FIGS. 11A-F present data showing bivalent DNA vaccines completely protect mice against homologous H1N1 influenza infection. Data are provided for mean weight loss (FIGS. 11 A, C and E) and survival after infection (FIGS. 11 B, D and F).

FIGS. 12A-C present data showing that bivalency of heterodimeric vaccine molecules increases antigen specific germinal centers and B cell population in bone marrow. A. Dilution curve of rHA probe fitted with non-linear regression. B. Representation of individual mice with 200 nM rHA probe. C. Cell suspensions from the bone marrow were analyzed with a B-cell ELISPOT to detect PR8 or Ca107 specific B cells. *p<0.05 and **p<0.01, unpaired two tailed student's t-test.

FIGS. 13A-D provide additional data related to vaccine molecules of the present invention. A. Heterodimeric ACID/BASE targeting vaccine. B. Vaccination of balb/c mice gave higher PR8-specific IgG1 for bivalent molecules than monovalent molecules. C. Only bivalent heterodimer induced full protection in a PR8 challenge. D. Competing ELISA. PR8 is used as coat and the sera from vaccinated mice is competed with Ca107 (Ca107/PR8 inhibited more than Ca107/Ca107) or with PR8 (Ca107/PR8 less inhibited than PR8/PR8).

FIGS. 14A-D provide a schematic model for induction of antibodies with targeted and bivalent DNA vaccines.

FIG. 15 provides a sequence comparison of Ca107 (SEQ ID NO:12) and PR8 (SEQ ID NO:13) from the hemagglutinin (HA) from H1: 81.5% identity.

FIG. 16 shows that ACID/BASE heterodimeric DNA vaccines induce protection against bone marrow myeloma (MOPC.315.BM) tumor after a single vaccination in BALB/c mice. Survival curves of the various vaccines compared to antigen control and NaCl vaccinated mice. The tumor-specific antigen M315 is measured in sera and ACID/BASE vaccinated mice shows significantly less M315 in sera then control vaccinated mice.

Figure 18:
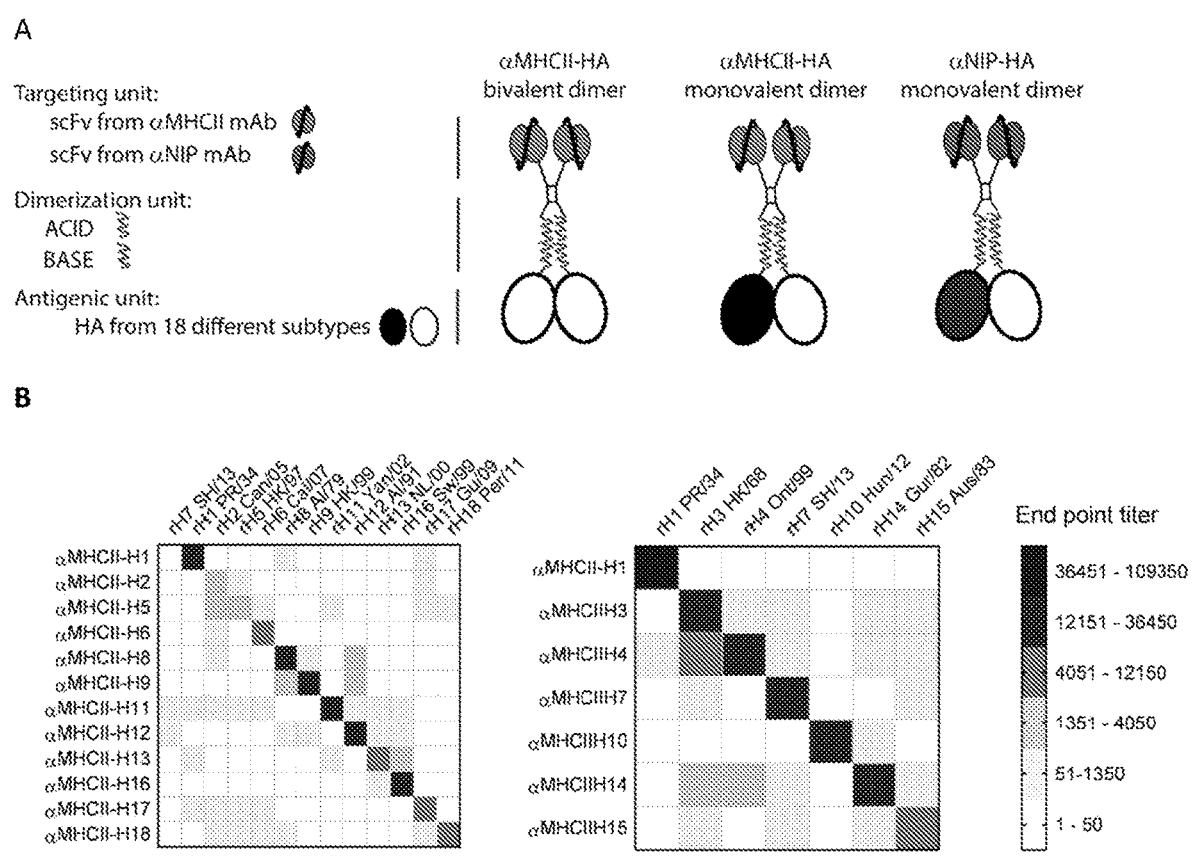

FIG. 18 shows that DNA vaccines with HA as antigen are functionally expressed in vitro and in vivo (A) Representation of vaccine proteins. (B) Balb/c mice were vaccinated intradermally with aMHCII-Hx bivalent dimers carrying HA from one of the 18 subtypes.

Figure 1:
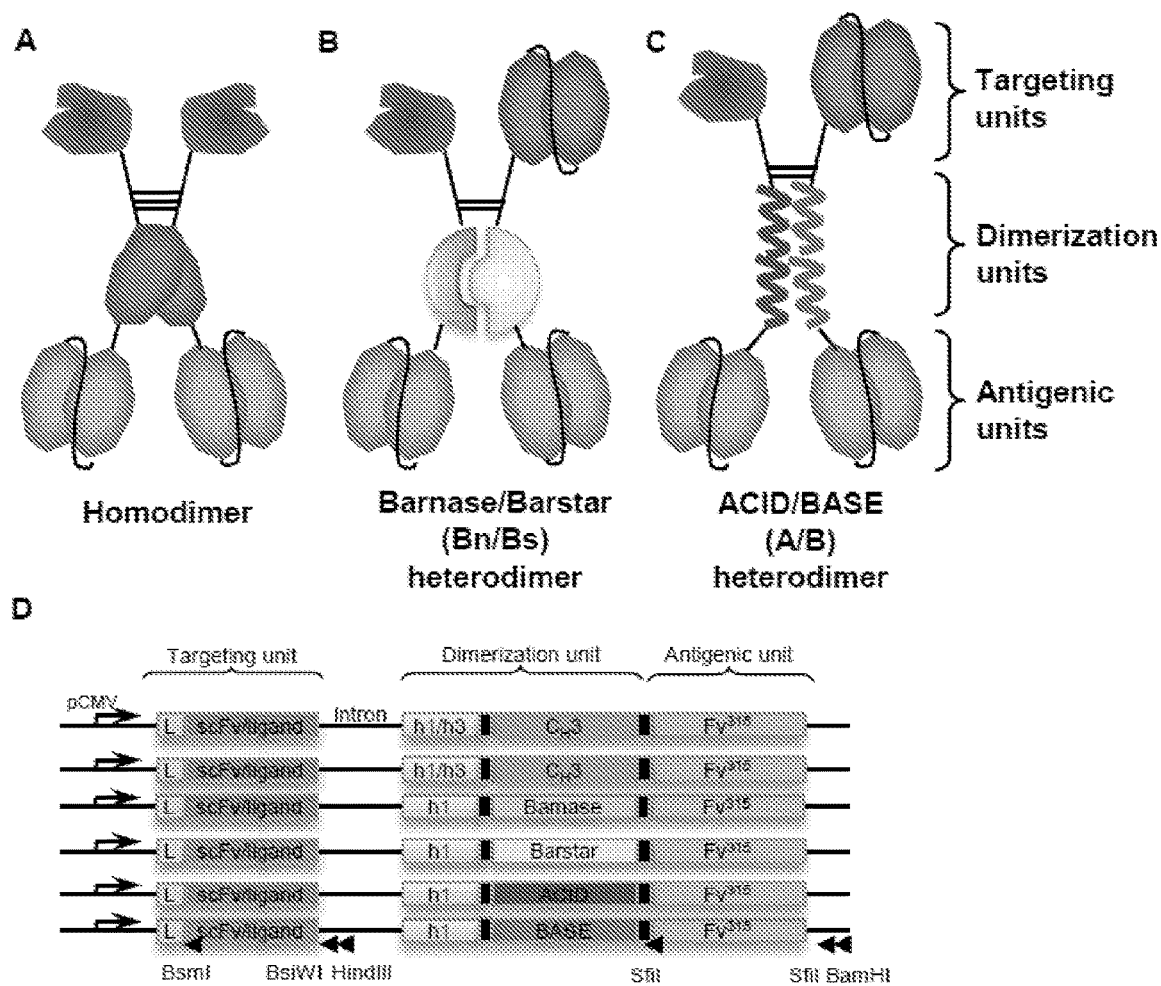
Figure 1E:
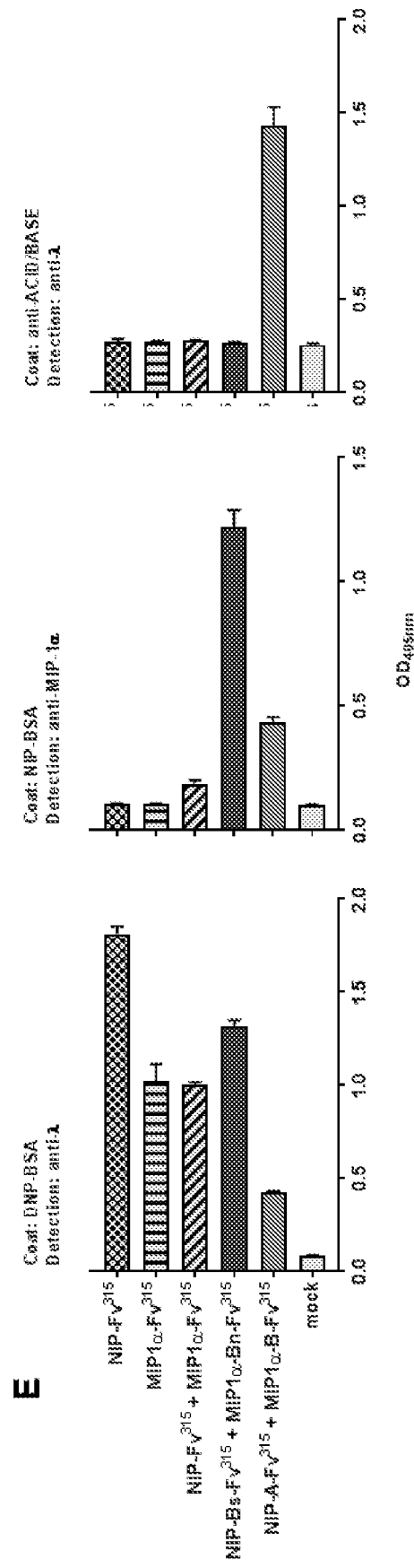

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to vaccines and particularly, but not exclusively, to compositions, methods, and uses of heterodimer vaccine molecules formed from monomers comprising a variant targeting unit and a variant antigenic unit joined by heterodimerization units.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "subject" and "patient" refer to any animal, such as a mammal like a dog, cat, bird, livestock, and preferably a human.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (e.g., minimize or lessen) the targeted pathologic condition or disorder. Those in need of treatment include those already with the disorder as well as those prone to have the disorder or those in whom the disorder is to be prevented.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F' $(ab)_2$, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments.

A molecule that "specifically binds to" or is "specific for" another molecule is one that binds to that particular molecule without substantially binding to any other molecule.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the term "administration" refers to the act of giving a drug, prodrug, antibody, vaccine, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, "carriers" include pharmaceutically acceptable carriers, excipients, or stabilizers which are nontoxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids;

antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "protein," "polypeptide," and "peptide" refer to a molecule comprising amino acids joined via peptide bonds. In general, "peptide" is used to refer to a sequence of 20 or less amino acids and "polypeptide" is used to refer to a sequence of greater than 20 amino acids.

As used herein, the term, "synthetic polypeptide," "synthetic peptide", and "synthetic protein" refer to peptides, polypeptides, and proteins that are produced by a recombinant process (i.e., expression of exogenous nucleic acid encoding the peptide, polypeptide, or protein in an organism, host cell, or cell-free system) or by chemical synthesis.

As used herein, the term "protein of interest" refers to a protein encoded by a nucleic acid of interest.

As used herein, the term "native" (or wild type) when used in reference to a protein refers to proteins encoded by the genome of a cell, tissue, or organism, other than one manipulated to produce synthetic proteins.

As used herein, "domain" (typically a sequence of three or more, generally 5 or 7 or more amino acids) refers to a portion of a molecule, such as proteins or the encoding nucleic acids, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as proteolytic activity. As such, a domain refers to a folded protein structure that retains its tertiary structure independently of the rest of the protein. Generally, domains are responsible for discrete functional properties of proteins, and in many cases may be added, removed or transferred to other proteins without loss of function of the remainder of the protein and/or of the domain.

A protein can have one, or more than one, distinct domains. For example, a domain can be identified, defined or distinguished by homology of the sequence therein to related family members, such as homology to motifs that define a protease domain or a gla domain. In another example, a domain can be distinguished by its function, such as by proteolytic activity, or an ability to interact with a biomolecule, such as DNA binding, ligand binding, and dimerization. A domain independently can exhibit a biological function or activity such that the domain independently or fused to another molecule can perform an activity, such as, for example proteolytic activity or ligand binding. A domain can be a linear sequence of amino acids or a non-linear sequence of amino acids. Many polypeptides contain a plurality of domains. Some domains are known and can be identified by those of skill in the art. It is to be understood that it is well within the skill in the art to recognize particular domains by name. If needed, appropriate software can be employed to identify domains.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism). The term "host cell" refers to any cell capable of replicating and/or transcribing and/or translating a heterologous gene. Thus, a "host cell" refers to any eukaryotic or prokaryotic cell, whether located in vitro or in vivo. For example, host cells may be located in a transgenic animal.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid or polypeptide or protein refers to a nucleic acid or polypeptide or protein sequence that is identified and separated from at least one contaminant nucleic acid or polypeptide or protein with which it is ordinarily associated in its natural source. Isolated nucleic acids or polypeptides or proteins are molecules present in a form or setting that is different from that in which they are found in nature. In contrast, non-isolated nucleic acids or polypeptides or proteins are found in the state in which they exist in nature.

The term "antigen" refers to a molecule (e.g., a protein, glycoprotein, lipoprotein, lipid, nucleic acid, or other substance) that is reactive with an antibody specific for a portion of the molecule.

The term "antigenic determinant" refers to that portion of an antigen that makes contact with a particular antibody (e.g., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (e.g., the "immunogen" used to elicit the immune response) for binding to an antibody. In some embodiments, the "antigenic determinant" or "epitope" is a "neo-epitope" or new epitope.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

As used herein, a "vaccine" comprises one or more immunogenic antigens intentionally administered to induce acquired immunity in the recipient (e.g., a subject).

Embodiments of the Technology

Although the disclosure herein refers to certain illustrated embodiments, it is to be understood that these embodiments are presented by way of example and not by way of limitation.

Figure 8:
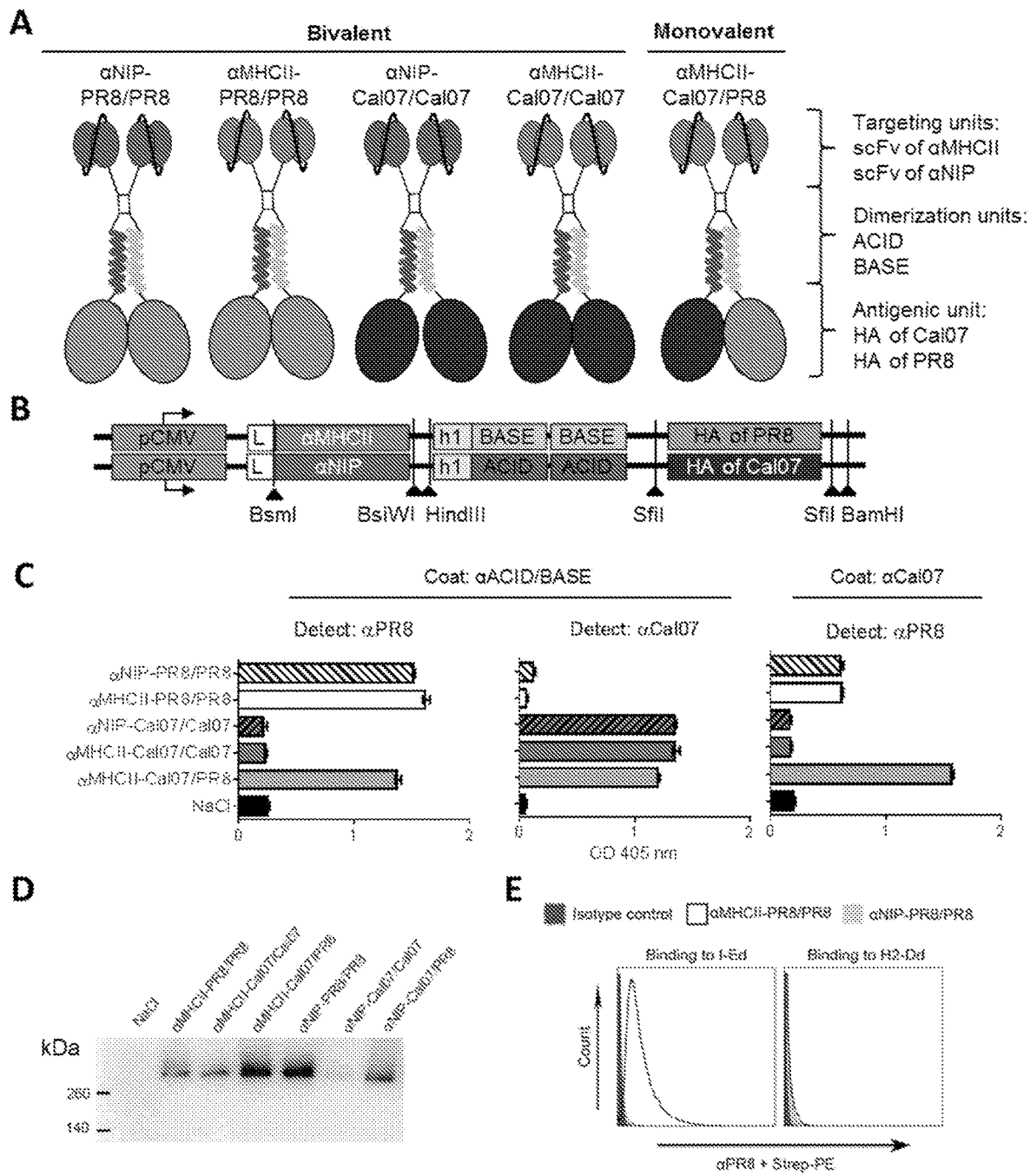
Figure 9:
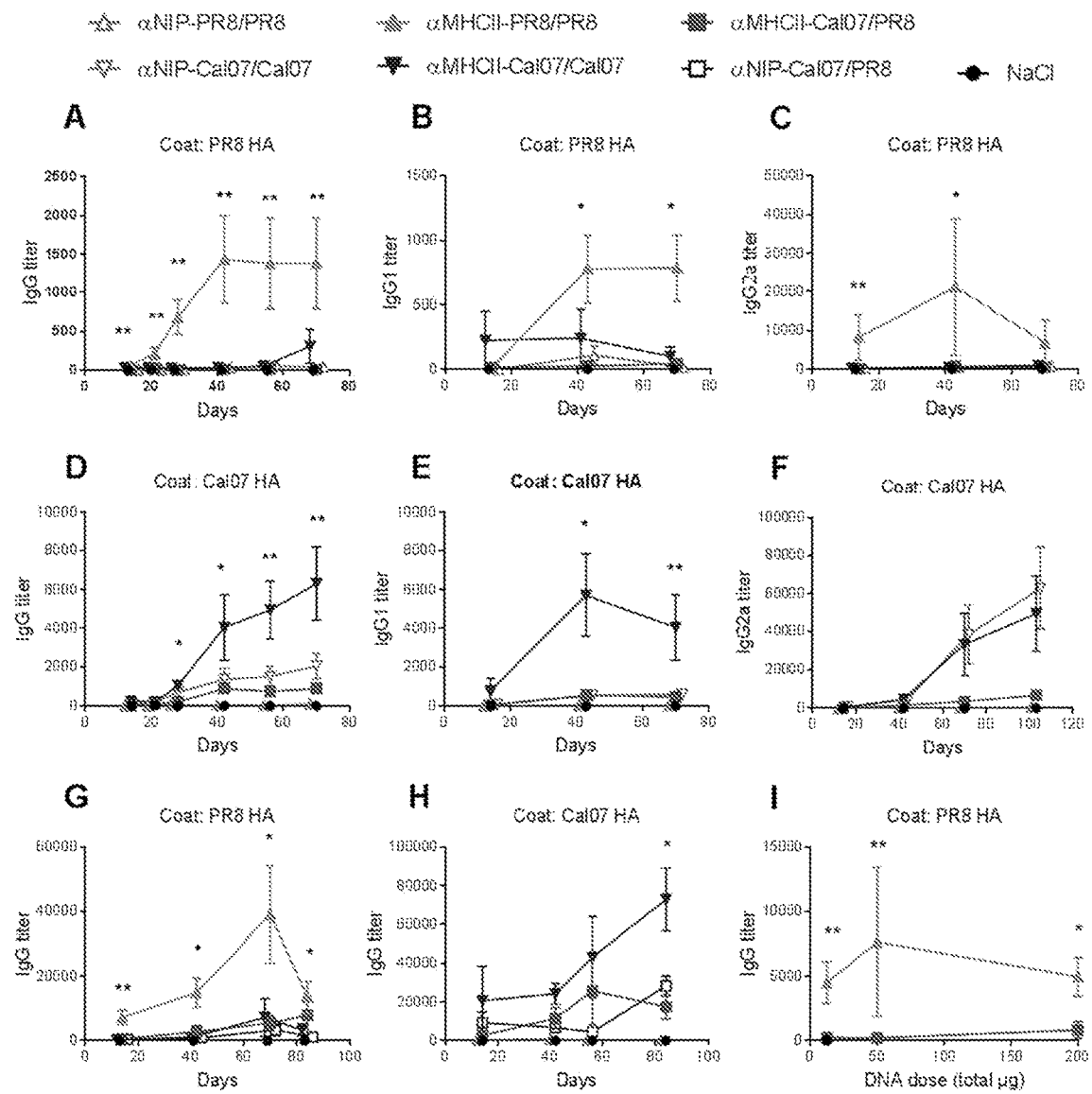
Figure 10:
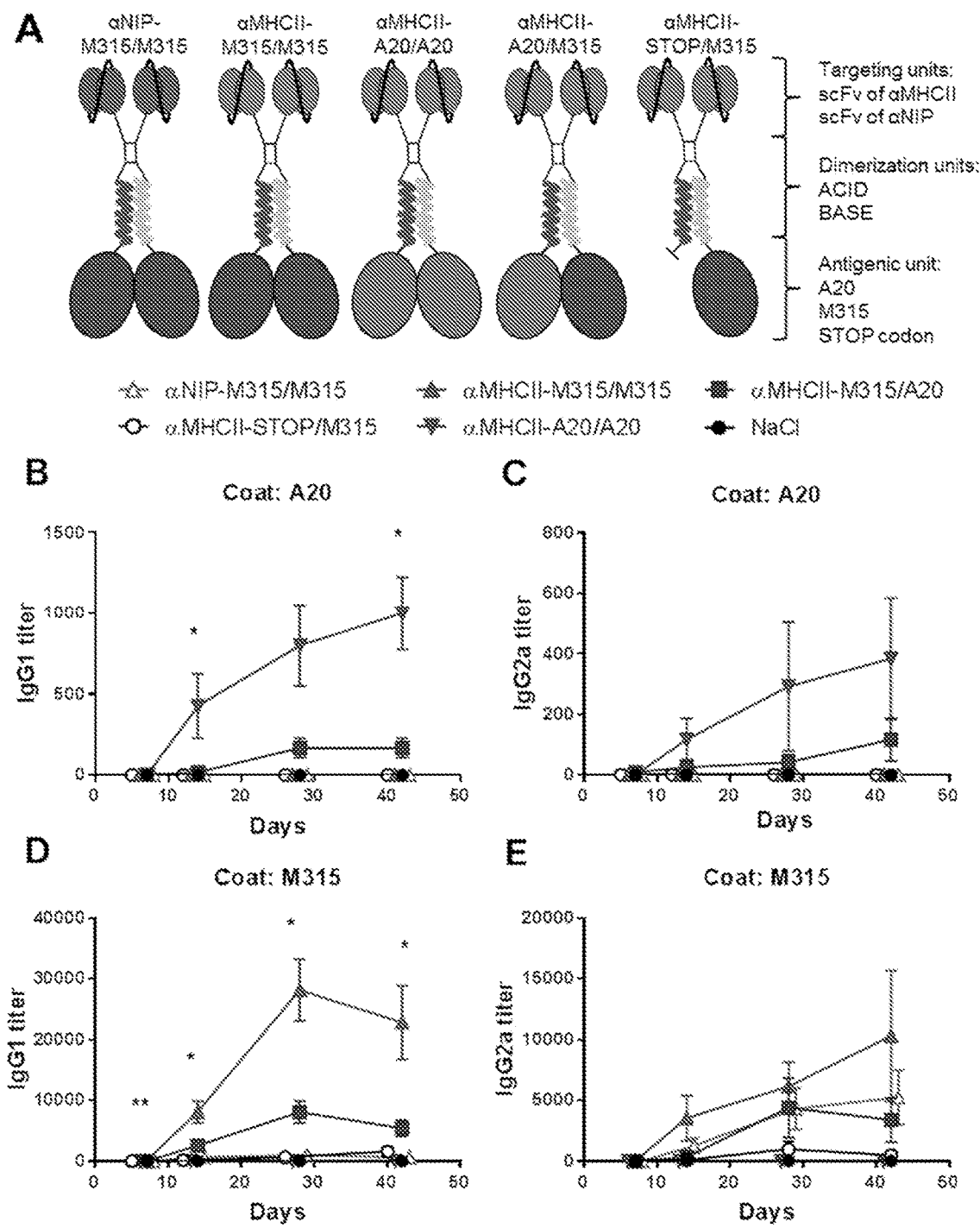
Figure 11:
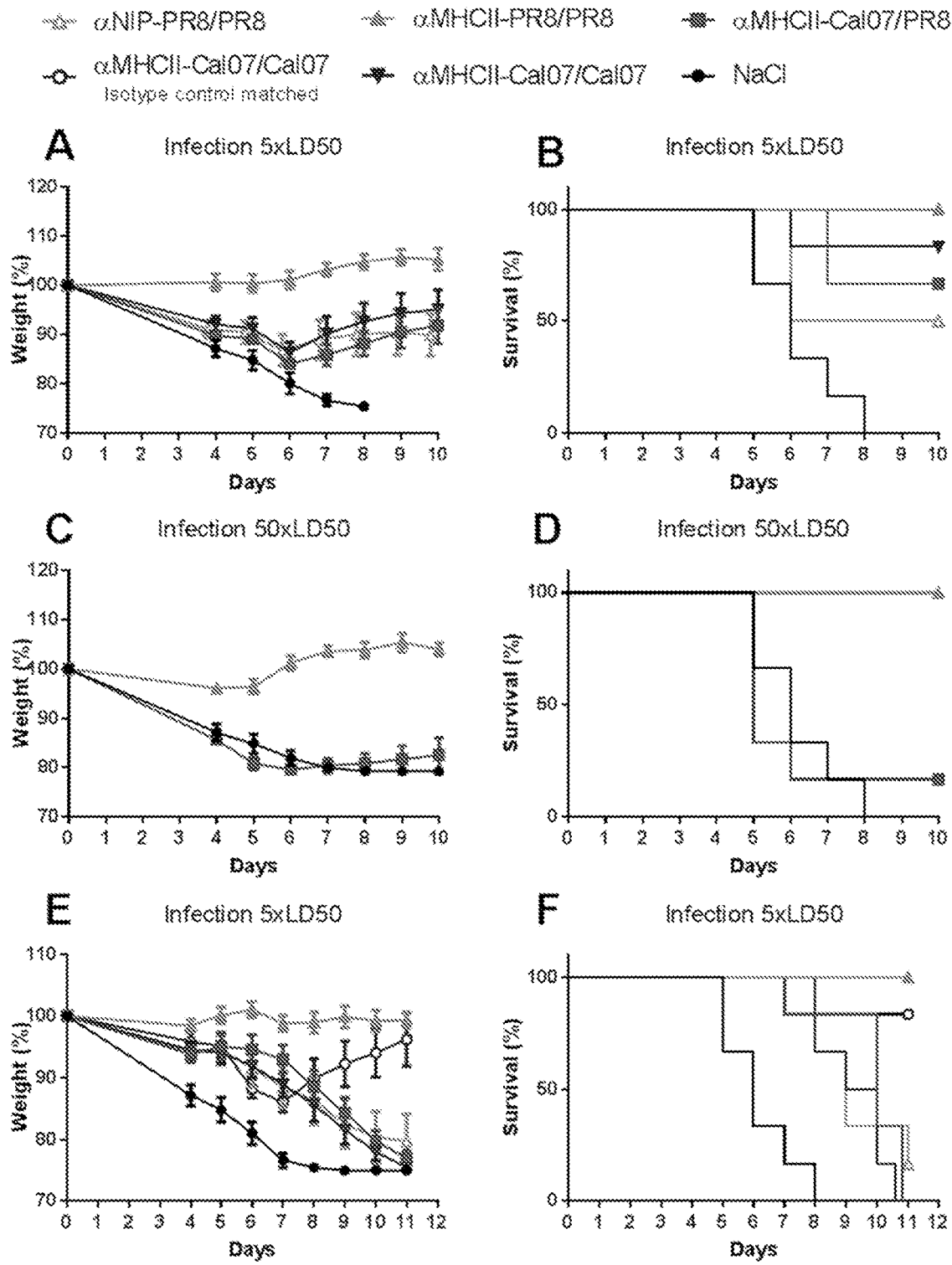
Figure 12:
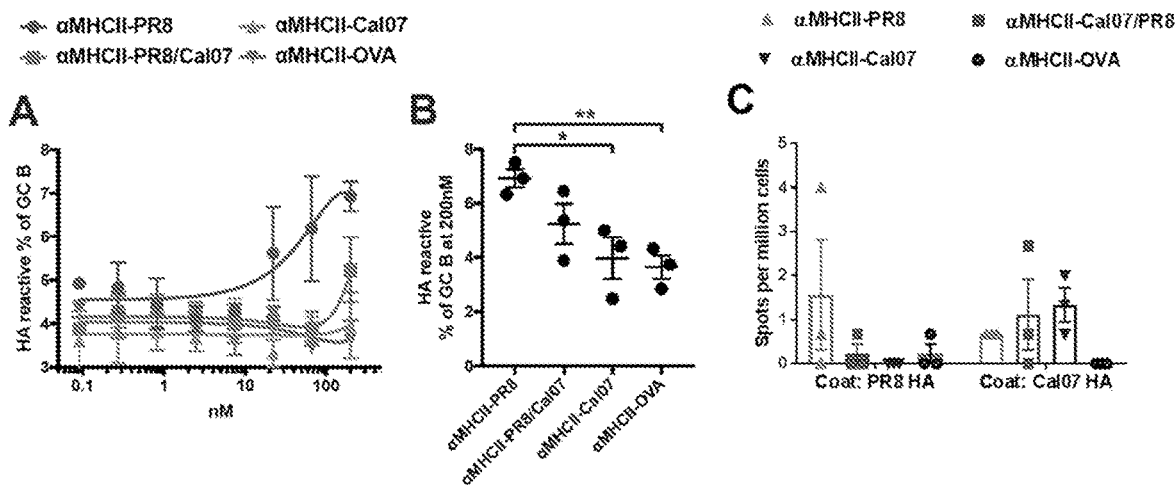

In some embodiments, the present invention provides a DNA vaccine comprising at least first and second nucleic acid constructs encoding at least first and second fusion proteins comprising a targeting unit, a heterodimerization domain, and an antigenic unit in operable association. In some embodiments, the antigenic unit for each of said first and second fusion proteins are variant target antigenic proteins. In some embodiments, when said first and second nucleic acid constructs are introduced into a cell the first and second fusion proteins are expressed and associate to form a first heterodimeric protein via association of said heterodimerization domains. This is shown schematically, for example, in FIGS. 1 and 8. As can be seen in these figures, introduction of the vaccine nucleic acid constructs into a host cell results in the production of monomer units comprising a targeting unit (exemplified by scFv such as anti-MHCII and anti-NIP), a heterodimerization unit (exemplified by ACID/BASE domains and barstar/barnase domains), and different antigenic units (exemplified by Fv315, and HA from PR8 and Ca107). Upon expression, monomers with the ACID domain pair with monomers with the BASE domain and, likewise, monomers with the barstar domain pair with monomers with the barnase domain to form heterodimeric protein molecules. Exemplary sequences for fusion proteins of the present invention are provided herein. For example, SEQ ID NOs:1 and 2 provide the nucleic acid sequences for constructs encoding a fusion protein with a MIP1a targeting unit and M315 antigenic unit separated by a hinge region and an ACID-ACID domain. SEQ ID NO:3 provides the corresponding amino acid sequence for the fusion protein. SEQ ID NOs:4 and 5 provide the nucleic acid sequences for constructs encoding a fusion protein with a MIP1a targeting unit and M315 antigenic unit separated by a hinge region and an BASE-BASE domain. SEQ ID NO:6 provides the corresponding amino acid sequence for the fusion protein. It will be understood that the exemplified constructs and fusion proteins are modular and that, for example, the exemplified targeting unit may be substituted with a different targeting units as described in more detail herein, the exemplified antigenic units may be substituted with different antigenic units as described in more detail herein, and the heterodimerization domains may be substituted with different heterodimerization domains as described in more detail herein. Additional antigenic units are exemplified by those provided as SEQ ID NOs: 7-13.

It will be recognized that the constructs may also be used to produce polypeptide vaccine compositions by expressing suitable expression vectors comprising the constructs in a host cell. Accordingly, the present invention also provides vaccine compositions comprising one or more heterodimeric protein molecules, wherein the heterodimeric protein molecules comprise at least first and second fusion protein monomers comprising a targeting unit, a heterodimerization domain, and an antigenic unit in operable association, wherein the antigenic unit for each of the first and second fusion protein monomers differ by encoding different variant target antigenic proteins, and wherein the heterodimeric protein molecule comprises two of the monomers joined by association of the heterodimerization domains.

In preferred embodiments, the different antigenic units are variants of a target antigenic protein, for example an antigenic protein from a pathogen such as a virus, bacterium, fungus or protozoa, or a target cancer antigen. In some embodiments, the cancer antigen is a neo epitope, which result from somatic or passenger mutations within the tumor that give rise to new epitopes or neoepitopes. Neoepitopes are recognized by the adaptive immune system as 'mutated self' and serve as the means by which immune systems can differentiate cancer from normal cells. Thus, neoepitopes may make strong candidates for personalized cancer immunotherapy vaccines. In some embodiments, the variants of a target antigenic protein are variants of the target antigenic protein from different strains of a target pathogen such as different strains of a virus, bacterium, fungus, or protozoan. In some embodiments, the variants of a target antigenic protein are variants of the target antigenic protein from different species or genera of a target pathogen such as different species or genera of a virus, bacterium, fungus, or protozoan. In some embodiments, the variants may be defined by the degree of identity of sequence shared by the variants of the target antigenic protein. A high degree of sequence identity is not required as variants target antigenic proteins from different strains of, for example, the same pathogenic organism may be quite diverse in sequence. In some embodiments, the variants may have about greater than 30%, 40%, 50%, 60%, 70%, 80%, 90%, 95%, 96%, 97%, 98% or 99% sequence identity. Accordingly, the DNA vaccine and vaccine compositions of the present invention may comprise sequences encoding 2, 3, 4, 5, 6, 7, 8, 9, 10, 11, 12, 13, 14, 15, 16, 17, 18, 19, or 20 variant target antigenic proteins, or from 2 to 10, 2 to 20, 2 to 30, 2 to 50, 3 to 10, 3 to 20, 3 to 30, 3 to 50, 4 to 10, 4 to 20, 4 to 30, 4 to 50, 5 to 10, 5 to 20, 5 to 30, 5 to 50, 6 to 10, 6 to 20, 6 to 30, or 6 to 50 variant target antigenic proteins, or greater than 2, 3, 4, 5, 6, 7, 8, 9 or 10 variant target antigenic proteins.

Figure 14:
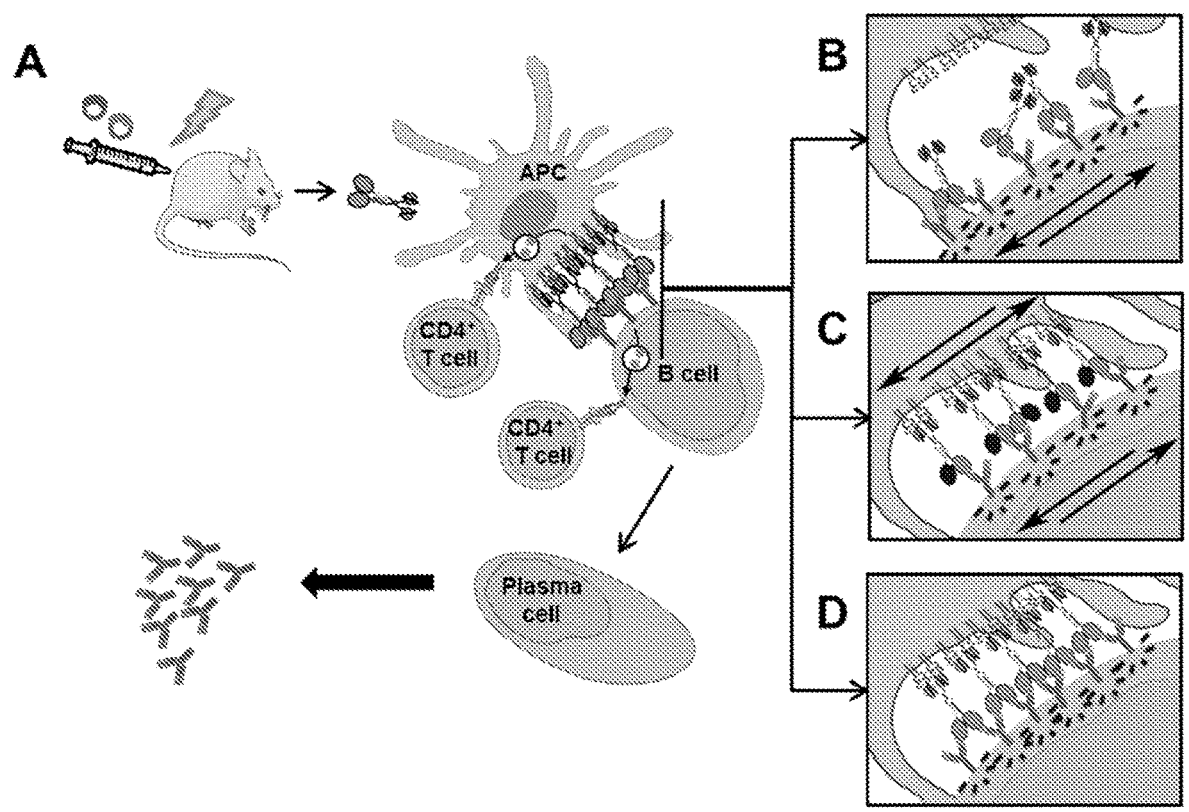

The present invention is not limited to a particular mechanism of action. Indeed, an understanding of the mechanism of action is not necessary to practice the present invention. Nevertheless, FIG. 14 provides a model for induction of an immune response with the vaccines of the present invention. Referring to FIG. 14, after DNA vaccination followed by electroporation, host cells can take up DNA and transcribe vaccine protein. See FIG. 14A. Targeting units on the vaccine effectively bind and activate APCs and are internalized and processed for display of antigen on MHCII to CD4+ T cells. Antigen specific BCRs recognize epitopes on the antigenic unit, which will cause vaccine protein to be internalized and processed by B cells. Display of antigen on MHCII of the B cell surface enables B cells to receive help from CD4+ T cells, activating the B cell to differentiate into plasma cells and production of antibodies. Additionally, targeted vaccine dimers could form a synapse between B cells and APC. Bivalent targeted vaccines enable one BCR to bind two arms of the vaccine dimers. When multiple APC bound vaccine dimers and BCR bind in tandem, as shown in (FIG. 14D), a synapse may be formed in which the BCRs are immobilized relative to one another in the B cell membrane. This forces the BCRs to remain close together in the membrane. This might amplify BCR signaling, resulting in increased B cell activation and eventually increased secretion of antigen specific antibodies. Monovalent targeted vaccines can promote the formation of a synapse, as shown in (FIG. 14C), but are not able to form the same rigid binding formation with the BCRs. The BCRs will be able to move in the membrane relative to one another (indicated by the arrows), causing less restrained BCR proximity. Non-targeted vaccines will not stabilize a B cell-APC synapse (FIG. 14B), and will likewise not be able to restrain the BCRs in the B cell membrane.

The constructs, components of the constructs, vaccines and uses of the vaccines are described in more detail below.

Antigenic Units

The vaccine molecules of the present invention preferably comprise different antigenic units that are variants of a target antigenic protein, for example an antigenic protein from a pathogen such as a virus, bacterium, fungus or protozoa, or a target cancer antigen. As described above, the variants may be defined by the degree of identity of sequence shared by the variants of the target antigenic protein or conserved regions with a target antigenic protein. In some embodiments, the variants may have about greater than 30%, 40%, 50%, 60%, 70%, 80%, 90%, 95%, 96%, 97%, 98% or 99% sequence identity. In still other embodiments, a conserved regions within the target variant proteins of more than 8, 10, 12, 15, 20, 30, 40, 50 or 60 amino acids in length and up to 100 to 200 amino acids in length may have greater than about 30%, 40%, 50%, 60%, 70%, 80%, 90% or 95% sequence identity. According to the present technology, an antigenic unit comprises an antigen, which is a substance that evokes the production of one or more antibodies in an organism such as a subject. Each antibody binds to a specific antigen. In some contexts, the term refers to any molecule or molecular fragment that can be bound by a major histocompatibility complex (MHC) and presented to a T-cell receptor.

In some contexts, an immunogen is a specific type of antigen. An immunogen is a substance that induces an adaptive immune response if injected alone (or, e.g., as a part of an antigenic unit of a dimeric vaccine molecule). Thus, an immunogen induces an immune response, whereas an antigen combines with the products of an immune response (e.g., antibodies) once they are made. As an aspect of the instant technology, "antigen" is used in its broadest sense to refer to a molecule, substance, chemical, or polymer such as a protein, polypeptide, and/or peptide against which an immune response is induced in a subject, e.g., as a prophylactic measure or as a treatment, whether it can be otherwise characterized as an immunogen and/or an antigen.

At the molecular level, an antigen can sometimes be characterized by its ability to be "bound" at the antigen-binding site of an antibody. Antibodies discriminate between the specific molecular structures present on the surface of the antigen. Antigens are usually proteins (e.g., polypeptides, peptides, proteins) or polysaccharides that are present, e.g., as parts (coats, capsules, cell walls, flagella, fimbrae, and toxins) of bacteria, viruses, and other microorganisms. Lipids and nucleic acids can be made antigenic by combining them with proteins and polysaccharides.

Cells present their immunogenic antigens to the immune system via a histocompatibility molecule. Depending on the antigen presented and the type of the histocompatibility molecule, several types of immune cells can become activated. By endocytosis or phagocytosis, exogenous antigens are taken into the antigen-presenting cells (APCs) and processed into fragments. APCs then present the fragments to T helper cells (CD4+) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages, and other particles.

According to embodiments of the technology, the dimeric vaccine molecule can be extended to a general medical treatment through induction of an immune response against any polypeptide of any origin. It is possible to incorporate any antigenic sequence provided it is of sufficient length to allow proper folding of the polypeptide. This sequence may be derived from, e.g., a pathogen of a cancer protein. In some embodiments, the target antigenic protein is a protein (or nucleic acid encoding a protein) used therapeutically to induce immune responses that will aid or remedy disease progression (e.g., viral infection, autoimmune diseases, or cancer).

In some embodiments, the molecule of interest is a pathogen-derived antigen (e.g., a nucleic acid or a polypeptide encoding an antigen or antigens from a pathogen). Exemplary pathogenic organisms include, but are not limited to, bacteria, viruses, fungi and protozoa. In some preferred embodiments, the pathogen-derived antigen is influenza hemagglutinin (HA). In some particularly preferred embodiments, the HA is from a group 1 influenza virus. In some embodiments, the group 1 influenza viruses are selected from the group consisting of two or more (i.e., 2 or more, 3 or more, 4 or more, five or more or all twelve) of H1, H2, H5, H6, H8, H9, H11, H12, H13, H16, H17 and H18. In still other embodiments, the HA is from a group 2 influenza virus selected from the group consisting of two or more (i.e., 2 or more, 3 or more, 4 or more, five or more or all six) of H3, H4, H7, H10, H14 and H15.

Antigens from other pathogenic organisms may also be used in the fusion of the present invention. Exemplary pathogens from which antigens may be obtained from include, but are not limited to, In some embodiments, the microorganism is *Bacillus*, including *Bacillus anthracis; Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*; *Staphylococcus*, e.g. *S. aureus*; *Haemophilus*, e.g. *H. influenzae*; *Neisseria*, e.g. *N. meningitidis*, *N. gonorrhoeae*; *Yersinia*, e.g. *Y. lamblia*, *Y. pestis*, *Pseudomonas*, e.g. *P. aeruginosa*, *P. putida*; *Chlamydia*, e.g. *C. trachomatis*; *Bordetella*, e.g. *B. pertussis*; *Treponema*, e.g. T palladium; *B. anthracis*, *Y. pestis*, *Brucella* spp., *F. tularensis*, *B. mallei*, *B. pseudomallei*, *B. mallei*, *B. pseudomallei*, *C. botulinum*, *Salmonella* spp., SEB *V. cholerae* toxin B, *E. coli* O157:H7, *Listeria* spp., *Trichosporon beigelii*, *Rhodotorula* species, *Hansenula anomala*, *Enterobacter* sp., *Klebsiella* sp., *Listeria* sp., *Mycoplasma* ssp., *Francisella* spp., *Bartonella* spp., *Borrelia* spp., *Campylobacter* spp., *Chlamydia* spp., *Simkania* spp., *Ehrlichia* spp., *Enterococcus* spp., *Coccidioides* spp., *Bordetella* spp., *Coxiella* spp., *Ureaplasma* spp., *Trichomatis* spp., *Helicobacter* spp., *Legionella* spp., *Mycobacterium* spp., *Corynebacterium* spp., *Rhodococcus* spp., *Rickettsia* spp., *Arcanobacterium* spp., *Listeria* spp., *Treponema* spp., *Brucella* spp., *Campylobacter* spp., *Pasteurella* spp., *Pseudomonas* ssp., *Burkholderii* spp. and the like, orthomyxoviruses, (e.g. influenza virus), paramyxoviruses (e.g., respiratory syncytial virus, mumps virus, measles virus), adenoviruses, rhinoviruses (human and porcine), coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B, C and E), herpesviruses (e.g., Herpes simplex virus, HV-I and HV-II, varicella-zoster virus, cytomegalovirus, Epstein-Barr virus), rotaviruses, Norwalk viruses, hantavirus, arenavirus, rhabdovirus (e.g. rabies virus), retroviruses (including HIV-1, HIV-2, HTLV-I and —II), papovaviruses (e.g. papillomavirus), polyomaviruses, picornaviruses, Dengue virus, Filoviruses (e.g., Marburg and Ebola viruses), Hantavirus, Rift Valley virus, HHV-8, Human papillomavirus, Bovine leukemia virus, Influenza virus, Guanarito virus, Lassa virus, Measles virus, Rubella virus, Mumps virus, Chickenpox (Varicella virus), Monkey pox, Epstein Bahr virus, Parvovirus B19, Hantaan virus, Sin Nombre virus, Venezuelan equine encephalitis, Sabia virus, West Nile virus, Yellow Fever virus, and the like, causative agents of transmissible spongiform encephalopathies, Creutzfeldt-Jakob disease agent, variant Creutzfeldt-Jakob disease agent, *Candida* strains including *C. glabrata, C. albicans, C. krusei, C. lusitaniae* and *C. maltosa*, as well as species of *Aspergillus, Cryptococcus, Histoplasma, Coccidioides, Blastomyces*, and *Penicillium, Cryptcooccus, Cryptosporidium, Giardia lamblia*, Microsporidia, *Plasmodium vivax, Plasmodium falciparum, Pneumocystis carinii, Toxoplasma gondii, Trichophyton mentagrophytes, Enterocytozoon bieneusi, Cyclospora cayetanensis, Encephalitozoon hellem, Encephalitozoon cuniculi, Ancylostama, Strongylus, Trichostrongylus, Haemonchus, Ostertagia, Ascaris, Toxascaris, Uncinaria, Trichuris, Dirofilaria, Toxocara, Necator, Enterobius, Strongyloides* and *Wuchereria; Acanthamoeba* and other amoebae, *Cryptosporidium, Fasciola, Hartmanella, Acanthamoeba, Giardia lamblia, Isospora belli, Leishmania, Naegleria, Plasmodium* spp., *Pneumocystis carinii, Schistosoma* spp., *Toxoplasma gondii*, and *Trypanosoma* spp., among other viruses, bacteria, archaea, protozoa, fungi, and the like).

The fusion molecules described herein can further comprise antigens from mammalian targets, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAMS, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11 c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAMS, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta7, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEMS, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R3Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1 BB CD137, ILA), TNFRSF21 (DR6), TNFRSF22 (DcTRAIL R2TNFRH2), TNFRST23 (DcTRAIL R1 TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

One skilled in the art will appreciate that the aforementioned list of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target as used herein refers not only to a specific biomolecule, but the set of proteins that interact with said target and the members of the biochemical pathway to which said target belongs. One skilled in the art will further appreciate that any of the aforementioned target antigens, the ligands or receptors that bind them, or other members of their corresponding biochemical pathway, may be operably linked to the Fc variants of the present invention in order to generate an Fc fusion. Thus for example, an Fc fusion that targets EGFR could be constructed by operably linking an Fc variant to EGF, TGF-b, or any other ligand, discovered or undiscovered, that binds EGFR. Accordingly, an Fc variant of the present invention could be operably linked to EGFR in order to generate an Fc fusion that binds EGF, TGF-b, or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the Fc variants of the present invention to develop an Fc fusion.

The choice of suitable antigen depends on the desired application. In some embodiments, constructs described herein target pathogen antigens. For anti-cancer treatment it is desirable to have a target whose expression is restricted to the cancerous cells. Some targets that have proven especially amenable to antibody therapy are those with signaling functions. Other therapeutic antibodies exert their effects by blocking signaling of the receptor by inhibiting the binding between a receptor and its cognate ligand. Another mechanism of action of therapeutic antibodies is to cause receptor down regulation. Other antibodies do not work by signaling through their target antigen. In some cases, antibodies directed against infectious disease agents are used.

In one embodiment, the fusion proteins of the present invention are used for the treatment of autoimmune, inflammatory, or transplant indications. Target antigens and clinical products and candidates that are relevant for such diseases include but are not limited to anti—a4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, anti-TNF (TNF, TNFa, TNFa, TNF-alpha) antibodies such as CDP571, CDP870, D2E7, Infliximab, MAK-195F, and anti-VLA-4 antibodies such as Antegren.

Targeting Units

A method to increase the immunogenicity of protein antigens is to incorporate the antigen into antibodies or antibody fragments that target immune system cells, for example, antigen-presenting cells (APC). APCs process antigens and present them to T-cells for the production of antibodies against the antigens. As such, delivering antigen to APCs provides an efficient route to inducing an immune response to the antigen.

An antigen-presenting cell (APC) is a cell that displays antigen complexes with major histocompatibility complex (MHC) on their surfaces. An APC takes up an antigen, performs antigen processing, and returns all or a portion of the antigen (e.g., an epitope) to the APC's surface within an MHC class II molecule for antigen presentation. The CD4 receptors borne by naive helper T cells ligate MHC class II. The epitope (within the MHC class II molecule) imprints the T cell receptor (TCR) of the naive helper T cell, memorizing that epitope.

T cells cannot recognize, and therefore cannot react to, an isolated antigen. T cells can only react to an antigen that has been processed and presented by cells via an MHC molecule. Most cells in the body can present antigen to CD8+ T cells via MHC class I molecules and, thus, are APCs; in some contexts, the term APC refers to those specialized cells that can prime T cells (e.g., activate a T cell that has not been exposed to antigen, termed a "naïve" T cell). These cells, in general, express MHC class II as well as MHC class I molecules, and can stimulate CD4+("helper") cells as well as CD8+("cytotoxic") T cells, respectively.

APCs are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the APC. An additional co-stimulatory signal is then produced by the APC, leading to activation of the T cell. APCs include dendritic cells, which have the broadest range of antigen presentation. Activated DCs are especially potent Th cell activators because, as part of their composition, they express co-stimulatory molecules such as B7. In addition, APCs include macrophages, B-cells, and some activated epithelial cells. Cells that can act as APCs when stimulated by certain cytokines (e.g., IFN-γ) include fibroblasts, thymic epithelial cells, thyroid epithelial cells, glial cells (brain), pancreatic beta cells, and vascular endothelial cells.

For example, in some embodiments, the targeting unit comprises a single chain fragment variable targeting unit specific for MHC Class II molecules. A single-chain variable fragment (scFv) is a fusion protein of the variable regions of the heavy and light chains of an immunoglobulin connected with a short linker peptide (e.g., about 10 to about 25 amino acids). The linker is usually rich in glycine for flexibility, as well as serine or threonine for solubility, and can either connect the N-terminus of the heavy chain with the C-terminus of the light chain or vice versa. scFv can be created directly from subcloned heavy and light chains derived from a hybridoma, e.g., from a mammalian cell culture, or in a bacterial cell culture such as a culture of E. coli.

The scFvs with a targeting function are either derived from B cell hybridomas expressing monoclonal antibodies (mAbs) that bind to surface molecules on APC, or they may be derived from any source, e.g. phage display libraries. The use of scFvs from B cell hybridomas as the targeting moiety opens for a great range of possible targets due to the large collection of B cell hybridomas that produce mAbs which bind different surface molecules on APC. Furthermore, one may choose the nature of the signal given to the targeted cell by employing agonistic or antagonistic mAbs. Growing knowledge of Ab-Ag interactions will allow the improvement of the binding affinity of such mAbs to their Ag by amino acid replacements in the binding sites. This can be performed by ordinary site-directed mutagenesis. For vaccine purposes, an attractive approach is to target the dimeric vaccine molecule to surface molecules expressed exclusively on subsets of dendritic cells (DC) that are able to initiate a strong, specific immune response towards the patients own Id. Examples of such target surface molecules on APC are MHCII molecules, CD40, CD14, CD11c, HLA-DP, Toll-like receptors, and chemokine receptors. Accordingly, in some embodiments the scFv is anti-MHC-II or anti-HLA (e.g., HLA-DP), anti-CD14, anti-CD11 c, anti-CD40, or anti-toll-like receptor (anti-toll-like receptor 2). In some embodiments, the targeting unit is a ligand (e.g., soluble CD40 ligand or a chemokine (e.g., RANTES, MIP-1α, Flt3-L, GM-SCF or Xcll)), a bacterial antigen (e.g., a flaggelin), Because the targeting scFv is inserted into the V cassette of the expression vector pLNOH2 (Norderhaug, Olafsen et al. 1997), it is easily exchanged with other scFvs Also, antigen may be targeted to antigen presenting cells (APC) by conjugating the antigen to antibodies or other antibody fragments directed against surface molecules (e.g., receptors) on various types of APC. Other targeting units include anti-immunoglobulins (e.g., anti-IgG, anti-IgA, anti-IgM, IgD, etc.), and Fab or Fab' fragments.

Heterodimerization Units

The dimeric vaccine molecules of the technology comprise a heterodimerization domain. In particular, each polypeptide of the dimeric vaccine molecule comprises a heterodimerization unit that interacts specifically with a heterodimerization unit on the other polypeptide to form the heterodimerization domain. Thus, as used herein, the term "heterodimerization domain" refers to a domain in a dimeric molecule formed by the interaction of two heterodimerization units, for example, ACID and BASE heterodimerization units or barstar and barnase heterodimerization units as described in more detail below. Specification examples of heterodimerization domains include, but are not limited to, ACID/BASE heterodimeriation domains and barstar/barnase heterodimerization domains.

In some embodiments, the heterodimerization domain is a leucine zipper is used such as the ACID/BASE heterodimerization system (see Busch, et al. 2002 "Stabilization of soluble, low-affinity HLA-DM/HLA-DR1 complexes by leucine zippers" *J Immunol Methods* 263: 111). In this system, one heterodimerization unit comprises an acidic leucine zipper domain, e.g., an ACID module (e.g., AcidP1 or Fos), and the other heterodimerization unit comprises a basic leucine zipper domain, e.g., a BASE module (e.g., BaseP1 or Jun), which interact specifically with one another to form the heterodimerization domain of the heterodimeric vaccine molecule.

In some embodiments, the heterodimerization domain comprises a bacterial barnase module and a bacterial barstar module. See, e.g., Späng HCL, Braathen R, Bogen B (2012) Heterodimeric Barnase-Barstar Vaccine Molecules: Influence of One versus Two Targeting Units Specific for Antigen Presenting Cells. PLoS ONE 7(9): e45393, incorporated herein by reference in its entirety. The *Bacillus amyloliquefaciens* proteins barnase and barstar bind each other with a very high affinity ($K_D$ of ~10-14 M), comparable to that between biotin and streptavidin. The barnase-barstar module can accommodate fusions with scFv N-terminally of barnase and barstar as well as scFv [29] or a second barnase C-terminal of barnase.

The technology, however, is not limited to heterodimeric vaccine molecules comprising ACID/BASE or barstar/barnase domains. Any dimerization domain can be used, e.g., that comprises two dimerization domains that are specific for one another. In some embodiments, a "knobs and holes" system is used (see Xie, et al. 2005 "A new format of bispecific antibody: highly efficient dimerization, expression and tumor cell lysis." J Immunol Methods 296: 95). This system is based on the CH3 domains of human IgG1 Fc fragment to produce the complementary knobs and holes that provide the dimerization domain of the dimeric vaccine molecule. One polypeptide comprises a knobs module and the other polypeptide comprises a holes module.

It will be understood that the heterodimerization domains of the at least first and second constructs encoding vaccine monomers of the present invention are different and compatible with one another. For example, where a DNA vaccine of the present invention comprises first and second nucleic acid constructs (or third and fourth constructs . . . , etc.), one of the constructs will have an ACID (or barstar) unit and the other construct of the dimer pair will have a BASE (or barnase) unit. Likewise, the heterodimeric vaccine polypeptide molecules of the present invention comprise a pair of monomers, where one of the monomers will have an ACID (or barstar) unit and the other monomer of the dimer pair will have a BASE (or barnase) unit.

DNA Vaccines

The technology provided herein provides DNA vaccines comprising nucleic acids encoding dimeric vaccine molecule. In some embodiments, a single nucleic acid comprises the two polypeptides that dimerize to form the dimer. In some embodiments, two separate nucleic acids comprise the two polypeptides that dimerize to form the dimer (e.g., one nucleic acid encodes one polypeptide and the other nucleic acid encodes the other nucleic acid). In various embodiments, the nucleic acids are any nucleic acid that can be introduced into a cell and from which a polypeptide can be expressed in vivo.

In these embodiments, the DNA vaccine comprises DNA molecules encoding the fusion constructs described above (i.e., a targeting unit operably linked to an antigenic unit via a dimerization domain and/or other linkers), alone or in association with other desired sequences. Unlike recombinant protein vaccines, in which the antigen is taken up by antigen presenting cells and expressed predominantly in the context of MHC class II, DNA in nucleic acid vaccines is taken up and expressed by antigen-presenting cells directly, leading to antigen presentation through both naturally processed MHC class I and II epitopes.

In some embodiments, DNA vaccines comprise nucleic acids encoding a fusion construct described herein in a vector suitable for expression of the nucleic acid. In some embodiments, the nucleic acid is expressed in an expression cassette. In particular embodiments, the expression cassette is a eukaryotic expression cassette. The term "eukaryotic expression cassette" refers to an expression cassette which allows for expression of the open reading frame in a eukaryotic cell. A eukaryotic expression cassette comprises regulatory sequences that are able to control the expression of an open reading frame in a eukaryotic cell, preferably a promoter and polyadenylation signal. Promoters and polyadenylation signals included in the recombinant DNA molecules are selected to be functional within the cells of the subject to be immunized. Examples of suitable promoters, especially for the production of a DNA vaccine for humans, include but are not limited to promoters from cytomegalovirus (CMV), such as the strong CMV immediate early promoter, Simian virus 40 (SV40), Mouse Mammary Tumor Virus (MMTV), Human Immunodeficiency Virus (HIV), such as the HIF Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals.

Other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

The present invention is not limited by the particular formulation of a vaccine composition. When the vaccine is a DNA vaccine, the vaccine may preferably be provided in saline or other physiologically acceptable solution or buffer. In some embodiments, the DNA is administered intramuscularly (i.m.) by needle injection into one or more tissues. In some embodiments, DNA vaccination is i.m. into each quadriceps femoris muscle. In some embodiments, electroporation is performed immediately after injection with delivery of pulses from electrodes inserted i.m. flanking the injection site (Needle EP) by the Elgen electroporator device (Elgen, Inovio Biomedical Co.), as published in Liu et al., (2008, J Virol 82: 5643-5649) with the electric pulses given as 5×60 ms at 50V/400 mA and 200 ms delay. In other embodiments, electroporation is performed sintradermal on the left and right flank followed by electroporation using the DermaVax (Cyto Pulse Sciences, Inc) system with 2 pulses of 450 V/cm×2.5 µs and 8 pulses of 110 V/cm×8.1 ms. Electroporation is performed to increase the translation of DNA vaccines into vaccine proteins. In some embodiments, an effective route is intramuscular injection into the hind leg quadriceps or tibialis anterior, followed by intradermal injection. These routes usually provoke strong, antigen-specific Th1-biased, humoral and cellular immune responses. In other embodiments, a gene gun is utilized. In these embodiments, the DNA vaccine described is above is coated onto particles, preferably gold particles.

The delivery method generally determines the dose required to raise an effective immune response. Saline injections require variable amounts of DNA, from 10 μg-1 mg, whereas gene gun deliveries require 100 to 1000 times. Generally, 0.2 μg-20 μg are required, although quantities as low as 16 ng have been reported. These quantities vary by species. Mice for example, require approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage". Electroporation also reduces the amount of DNA needed (e.g., from 0.04 μg to 12.50 μg pr. plasmid).

Vaccines

Dimeric vaccine molecules as provided by the technology provided herein find use in compositions that are vaccines, vaccine components, and/or a pharmaceutical comprising a dimeric vaccine molecule (e.g., a dimeric polypeptide molecule), DNA/RNA sequences, or expression vectors according to the technology. Where appropriate, this pharmaceutical additionally comprises a pharmaceutically compatible carrier. Suitable carriers and the formulation of such pharmaceuticals are known to a person skilled in the art. Suitable carriers are, e.g., phosphate-buffered common salt solutions, water, emulsions, e.g. oil/water emulsions, wetting agents, sterile solutions, etc. The pharmaceuticals may be administered orally or parenterally. The methods of parenteral administration comprise the topical, intra-arterial, intramuscular, subcutaneous, intramedullary, intrathekal, intraventricular, intravenous, intraperitoneal, or intranasal administration. The suitable dose is determined by the attending physician and depends on different factors, e.g. the patient's age, sex and weight, the kind of administration etc.

In one aspect, vaccines or vaccine components are used to immunize mice to produce hybridomas. In some embodiments, the vaccine is for an infectious disease; in other embodiments the vaccine is a therapeutic vaccine for a cancer. Infectious diseases for which a vaccine may be constructed include but are not limited to viral diseases (including rotavirus, norovirus, rabies, influenza virus, herpesvirus, etc.), bacterial diseases (e.g., gonorrhea, streptococcal pneumonia, tuberculosis, tularemia, etc), fungal diseases (e.g., histoplasmosis, blastomycosis, and candidiasis) and protozoal diseases (e.g., cryptosporidiosis, leishmaniasis, filariasis, etc). Examples of cancers which may respond to therapeutic vaccination are, e.g., cervical cancer, melanoma, myeloma, and breast cancer. In some embodiments, the vaccine is for human use and in some embodiments it is for vaccination of animals, e.g., livestock, companion animals, and any other type of animal (fish, wildlife, etc.). Said vaccines can further also be applied in vitro to cells derived from a subject (e.g., a patient) to cause APC binding and presentation; said cells may then be returned to the host (subject, patient) of origin.

In some embodiments, nucleic acids expressing the polypeptides of the dimeric vaccine molecule are present in a host cell in vitro for the production of the dimeric vaccine molecule. Recombinant methods for producing polypeptides in a cell culture are well known in the art. For example, in some embodiments, the polypeptides of the dimeric vaccine molecule are expressed in a bacterial culture such as a culture of E. coli and the polypeptides of the dimeric vaccine molecule are purified and isolated from the culture to provide the vaccine. In some embodiments, the host cell is a eukaryotic cell kept in cell culture (e.g., transfected into NSO cells, 293E cells and Cos-7 cells) and may or may not by a transformed cell in some embodiments.

In one embodiment, the dimeric vaccine molecule is administered parenterally. In another embodiment the dimeric vaccine molecule is administered to a mucosal surface such as the nasal cavity or other mucosa. In another particular embodiment the dimeric vaccine molecule is administered orally so as to permit presentation to the buccal or gastrointestinal mucosa. In some forms of oral administration the dimeric vaccine molecule is encapsulated in an enteric capsule or gel capsule. In yet other embodiments the dimeric vaccine molecule is combined into a chewable form. When the delivery is to an animal the dimeric vaccine molecule can be incorporated into a bait or foodstuff. In some embodiments, the dimeric vaccine molecule can be applied topically to the skin.

In some embodiments, the present invention provides vaccine compositions comprising a dimeric vaccine molecule as provided herein. The present invention is not limited by the particular formulation of a composition comprising a dimeric vaccine moleculer. Indeed, a vaccine composition of the present invention may comprise one or more different agents in addition to the dimeric vaccine molecule. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a vaccine composition comprising a dimeric vaccine molecule comprises an agent or co-factor that enhances the ability of the antigenic unit to induce an immune response (e.g., an adjuvant). In some preferred embodiments, the presence of one or more co-factors or agents reduces the amount of antigenic unit required for induction of an immune response (e.g., a protective immune response (e.g., protective immunization)). In some embodiments, the presence of one or more co-factors or agents is used to skew the immune response towards a cellular (e.g., T-cell mediated) or humoral (e.g., antibody-mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995, incorporated by reference herein in its entirety for all purposes. The present invention is not limited by the type of adjuvant utilized (e.g., for use in a composition (e.g., a pharmaceutical composition)). For example, in some embodiments, suitable adjuvants include an aluminium salt such as aluminium hydroxide gel (e.g., alum) or aluminium phosphate. In some embodiments, an adjuvant may be a salt of calcium, iron, or zinc, or it may be an insoluble suspension of acylated tyrosine, or acylated sugars, cationically or anionically derivatized polysaccharides, or polyphosphazenes.

In general, an immune response is generated to an antigen through the interaction of the antigen with the cells of the immune system. Immune responses may be broadly categorized into two categories: humoral and cell-mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an antigenic unit). Immune responses can be measured in many ways including activation, proliferation, or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1-type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF, and low levels of TNF-α. Th1 type cytokines promote both cell-mediated immunity and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising an antigenic unit (e.g., dimeric vaccine molecule as provided by the technology described). However, in other embodiments, the present invention provides a method of stimulating a Th2-type immune response in a subject (e.g., if balancing of a T cell mediated response is desired) comprising administering to a subject a composition comprising an antigenic unit (e.g., a dimeric vaccine molecule as provided by the technology described). In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular, 3-de-O-acylated monophosphoryl lipid A (3D-MPL)), is used. 3D-MPL is a well known adjuvant manufactured by Ribi Immunochem, Montana. It is often supplied as a mixture of 3-de-O-acylated monophosphoryl lipid A with either 4, 5, or 6 acylated chains. In some embodiments, diphosphoryl lipid A and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 micrometers in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree Quillaja Saponaria Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146,431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety).

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activates various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63), LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., WO93/13202 and WO92/19265, each of which is hereby incorporated by reference), and other immunogenic substances (e.g., that enhance the effectiveness of a composition of the present invention) are used with a composition comprising a dimeric vaccine molecule of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a dimeric vaccine molecule, or the adjuvant may be formulated with carriers, for example liposomes or metallic salts (e.g., aluminium salts (e.g., aluminium hydroxide)) prior to combining with or co-administration with a composition.

In some embodiments, a composition comprising a dimeric vaccine molecule comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a dimeric vaccine molecule comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives is contemplated to be useful in the present invention including, but not limited to, cross-linked derivatives of poly(acrylic acid) (e.g., carbopol and polycarbophil), polyvinyl alcohol, polyvinyl pyrrolidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a dimeric vaccine molecule) enhances induction of an immune response in a subject (e.g., administered a composition of the present invention) due to an increase in duration and/or amount of exposure to an antigenic unit that a subject experiences when a mucoadhesive is used compared to the duration and/or amount of exposure to a dimeric vaccine molecule in the absence of using the mucoadhesive.

In some embodiments, a composition of the present invention may comprise sterile aqueous preparations. Acceptable vehicles and solvents include, but are not limited to, water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a dimeric vaccine molecule of the present invention can be used therapeutically (e.g., to enhance an immune response) or as a prophylactic (e.g., for immunization (e.g., to prevent signs or symptoms of disease)). A composition comprising a dimeric vaccine molecule of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal, and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the route of administration as it has been shown that mucosal administration of antigens induces protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). In addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a dimeric vaccine molecule of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In some embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a sujbect to be immunized. In some embodiments, a nebulized or aerosolized composition is provided. Enteric formulations such as gastro resistant capsules for oral administration, suppositories for rectal or vaginal administration also form part of this invention. Compositions of the present invention may also be administered via the oral route. Under these circumstances, a composition comprising a dimeric vaccine molecule may comprise a pharmaceutically acceptable excipient and/or include alkaline buffers or enteric capsules. Formulations for nasal delivery may include those with dextran or cyclodextran and saponin as an adjuvant.

Compositions of the present invention may also be administered via a vaginal route. In such cases, a composition comprising a dimeric vaccine molecule may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition comprising a dimeric vaccine molecule is administered to a mucosal surface of a subject in either a priming or boosting vaccination regime. Alternatively, in some embodiments, the composition is administered systemically in either a priming or boosting vaccination regime. In some embodiments, a composition comprising a dimeric vaccine molecule is administered to a subject in a priming vaccination regimen via mucosal administration and a boosting regimen via systemic administration. In some embodiments, a composition comprising a dimeric vaccine molecule is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal, or intravenous administration. A composition comprising a dimeric vaccine molecule may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention is a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers, and/or other agents useful in therapy. Also, the use of liposomes, microcapsules or microspheres, inclusion complexes, or other types of carriers is contemplated.

Thus, in some embodiments, a composition comprising a dimeric vaccine molecule of the present invention may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance a immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., $E.\ coli$). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, transdermal, intranasal, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies, and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics, or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the antigenic unit or other components of the formulation. In some embodiments, immunostimulatory compositions of the present invention are administered in the form of a pharmaceutically acceptable salt. When used, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, vaccine compositions are co-administered with one or more antibiotics. For example, one or more antibiotics may be administered with, before and/or after administration of the composition. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

Numerous antimicrobial agents are currently available for use in treating bacterial, fungal, and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a vaccine composition comprising a dimeric vaccine molecule with one or more additional active and/or immunostimulatory agents (e.g., a composition comprising a different antigenic unit, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a dimeric vaccine molecule is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an antigenic unit or organism from which the antigenic unit is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of the composition) may have a stronger immune response to an antigenic unit than a subject administered a composition via just one route.

Other delivery systems can include time-release, delayed release, or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a vaccine composition of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of a nanomulsion and antigenic unit present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a dimeric vaccine molecule of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an antigenic unit in a boost dose enables vigorous systemic immunity in a subject. The boost can be with the same formulation given for the primary immune response, or can be with a different formulation that contains the antigenic unit or the minimum immunogenic epitope. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing albumin variant, antigenic units, and other components and for screening for new components. Thus, it is not intended that the present invention be limited to any particular subject and/or application setting.

The present invention further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

EXAMPLES

Example 1. Novel Heterodimeric DNA Vaccine Protects Against MOPC315 Myeloma in BALB/c Mice DNA vaccines encoding fusion proteins that target antigen to antigen-presenting cells (APC) have an enhanced ability to induce immune responses. It would be useful to extend this technology to vaccine molecules that can simultaneously target several different surface molecules on APC for delivery of several different antigens. This example describes the production of heterodimeric vaccine molecules that each can express four different fusion moieties.

Two different types of heterodimers were synthesized, the first utilizing the Barnase-barstar protein pair and the second utilizing modified leucine-zipper α-helixes, termed the ACID/BASE-motif. See FIGS. 1B-D. The heterodimers have targeting moieties fused N-terminally and antigens fused C-terminally. These may be compared to the Vaccibody vaccine molecule, which uses the CH3 Ig domain from human IgG3 as dimerisation motif. See FIG. 1A.

Exemplary sequences for constructs and antigenic units of the invention are provided below.

Figure 2:
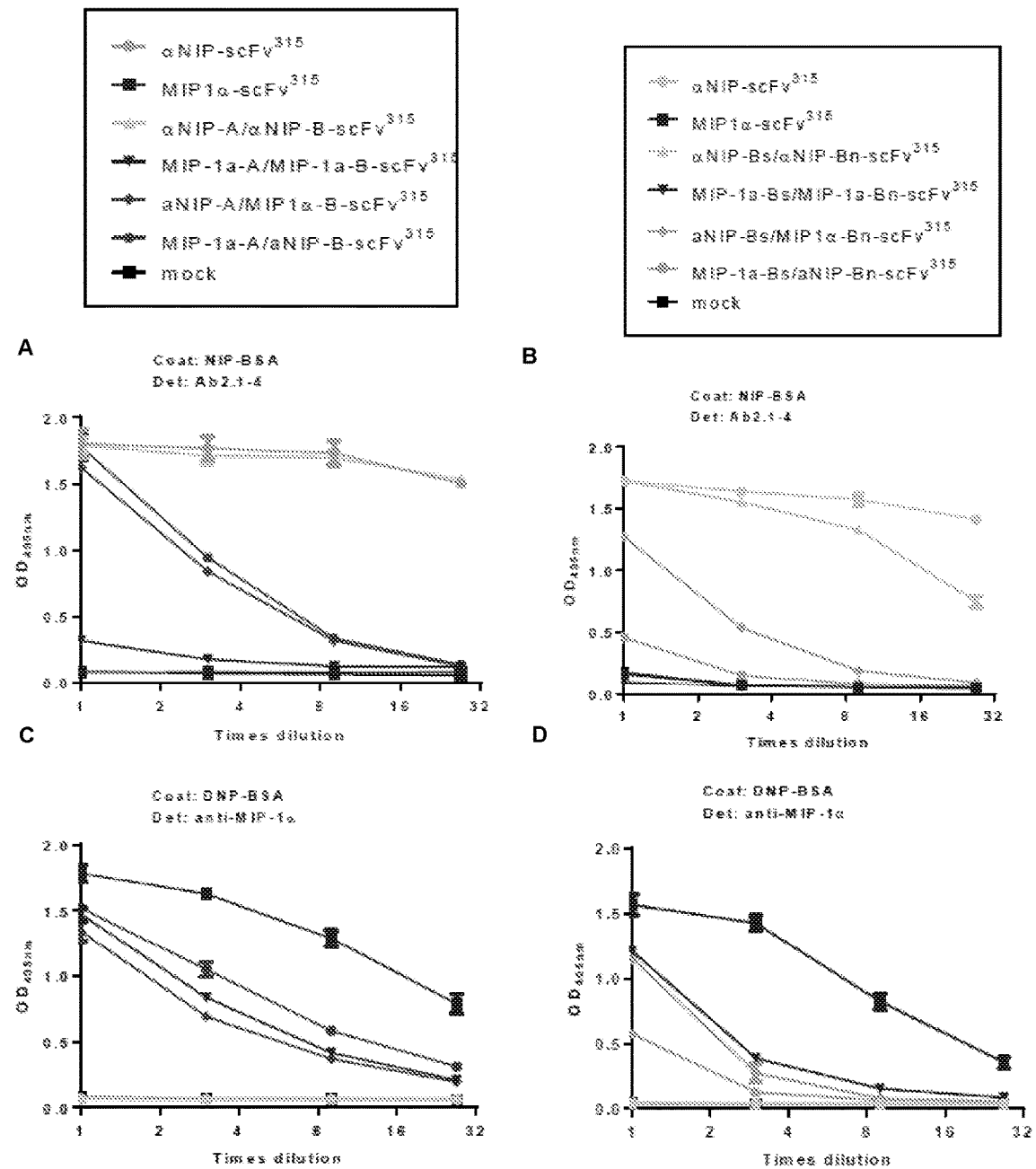
Figure 3:
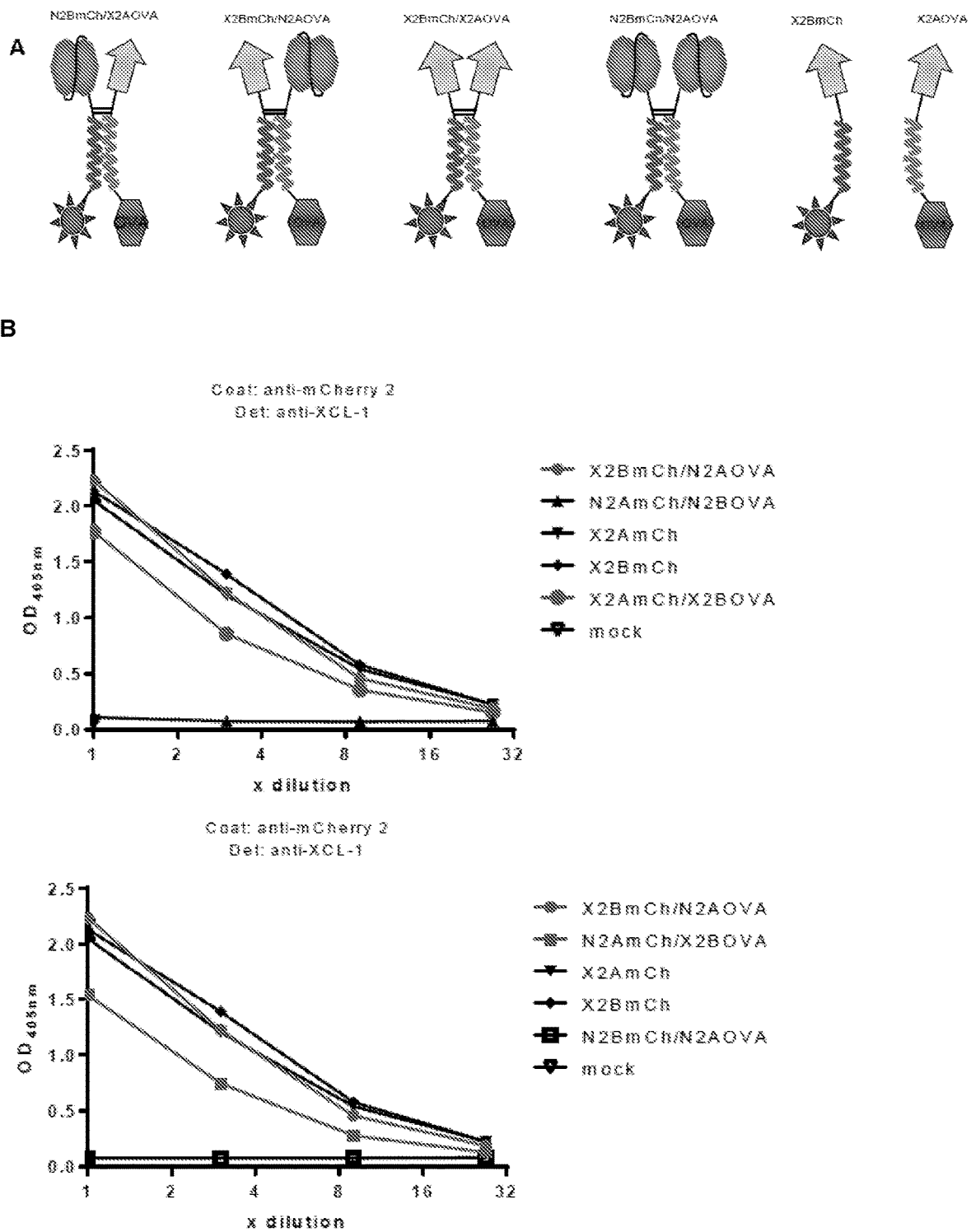
Figure 4:
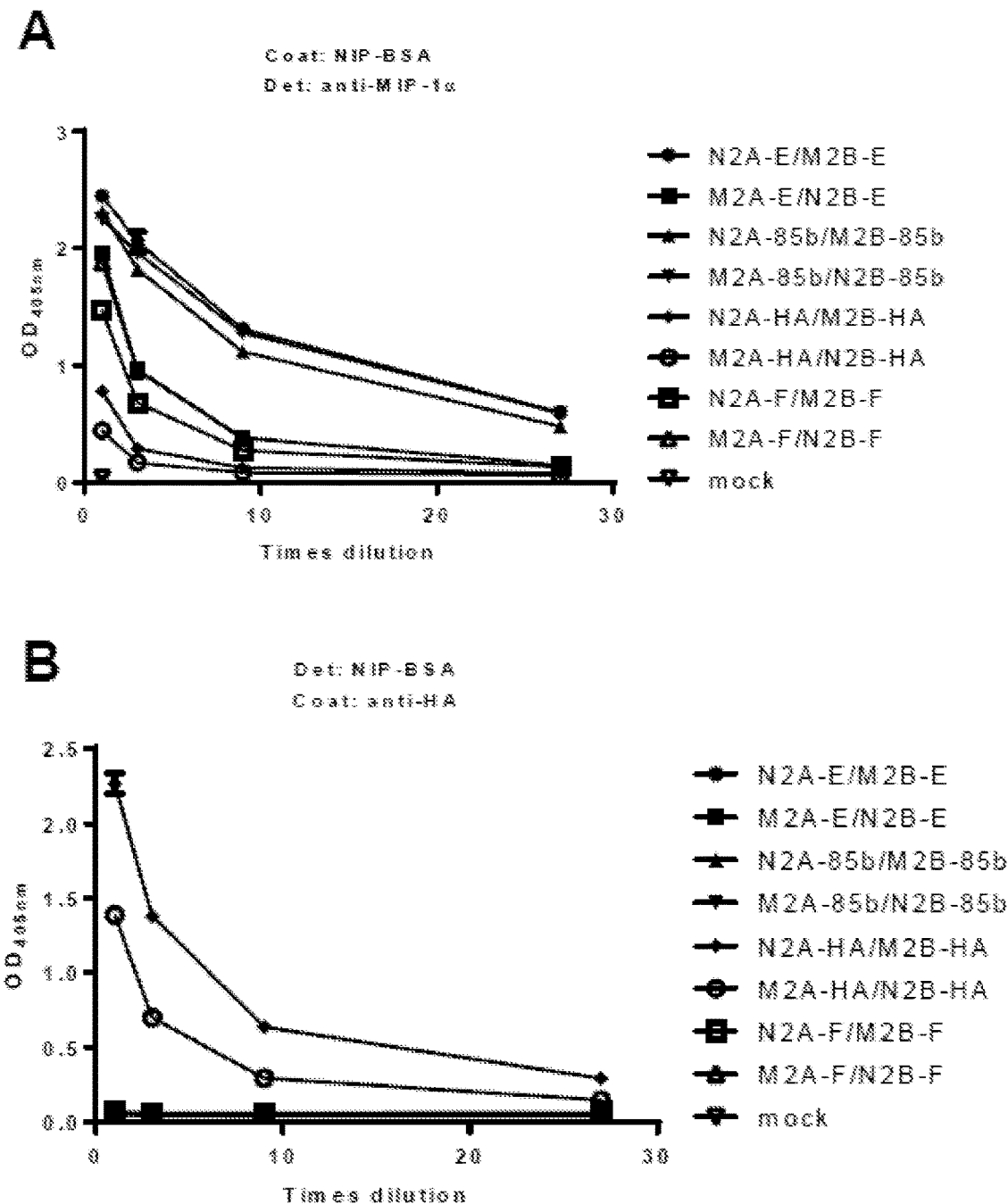
Figure 4:
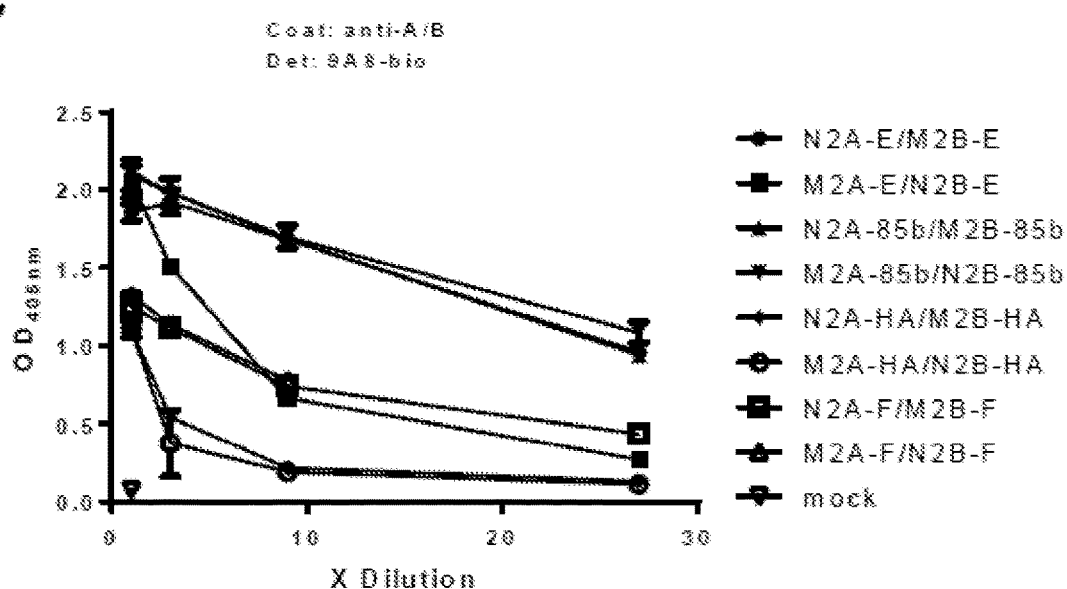
Figure 4:
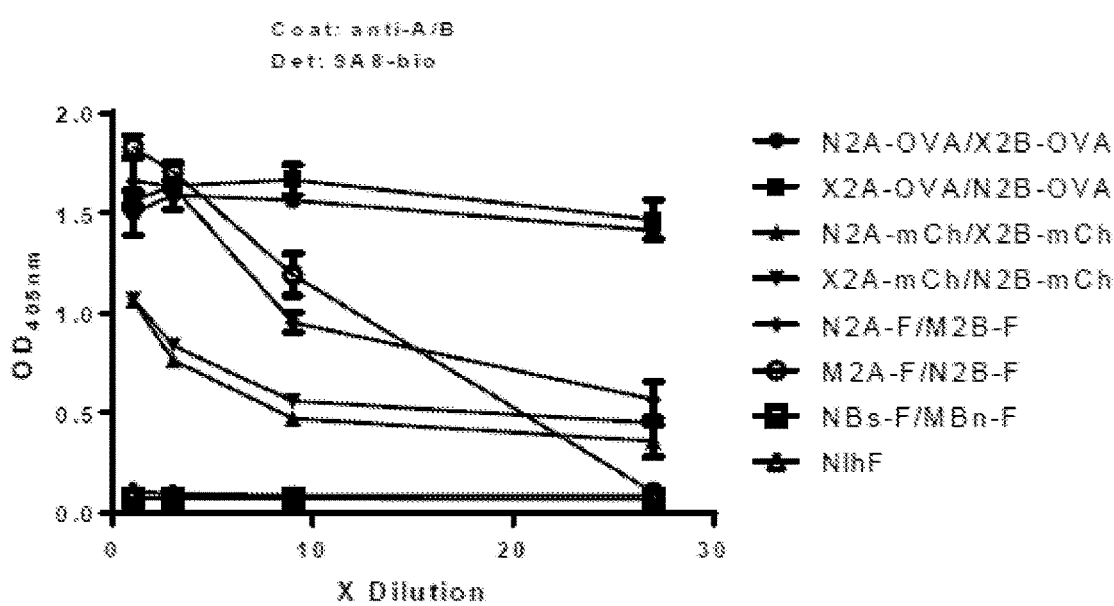
Figure 5:
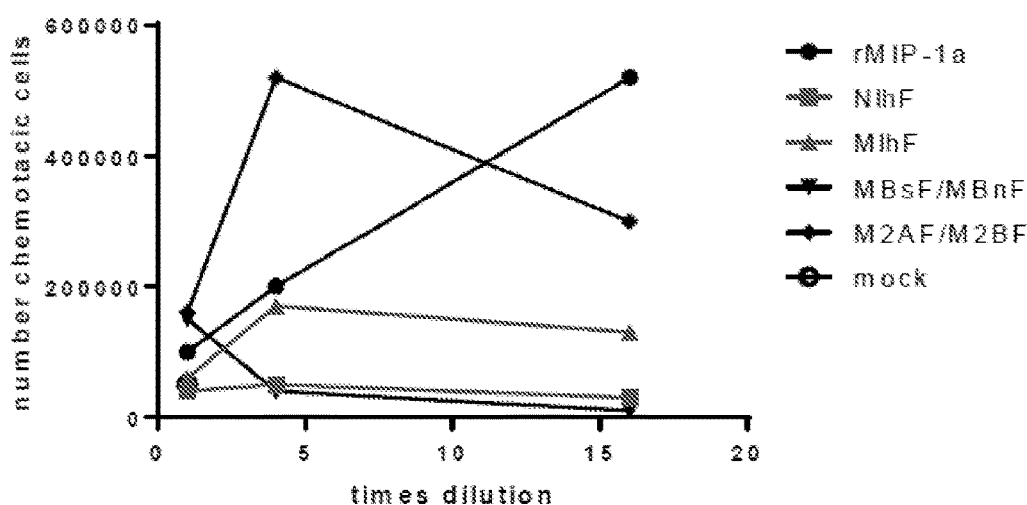
Figure 5:
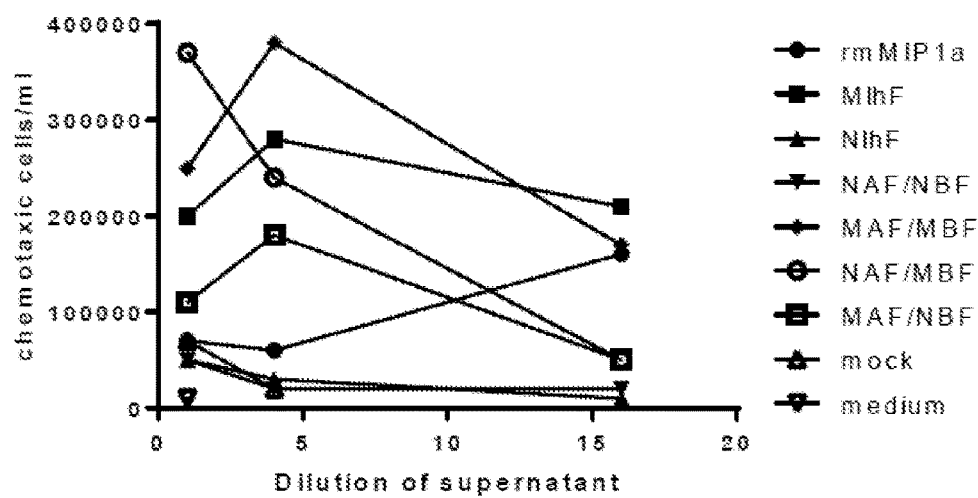

A number of different experiments were conducted to analyze both heterodimer formation and to compare the ability the heterodimers to generate immune responses. The heterodimers were specifically compared to vaccibodies, which are a homodimeric format. The levels of vaccine protein produced in vitro is similar for the ACID/BASE heterodimers ACID/BASE and vaccibody constructs in vitro. See FIG. 2. Briefly, the the various heterodimeric and homodimeric plasmids were transiently transfected into Hek293E cells and the supernatant harvested and analyzed on ELISA. The levels of protein secreted from the cells are measured by DNP-BSA, the antigen bound by scFvM315 (F) and 9A8, a mAb that recognize both λ1 and λ2 which is both in anti-NIP and scFvM315. The results are presented in FIG. 2. The ability of the ACID/BASE dimerization domain to form heterodimers was analyzed. See FIG. 3. Again, various ACID/BASE plasmid pairs and single plasmids were transiently transfected into Hek293E cells and the supernatant harvested and analyzed on ELISA. The results show that antigens and targeting units can be equally expressed on ACID or BASE monomers. Furthermore, monomeric ACID and BASE fusion proteins may be secreted in vitro. A number of different antigens can be used to make vaccine molecules. See FIG. 4, which presents the results of in vitro analysis of various ACID/BASE heterodimers. Plasmids encoding heterodimers comprising antigens for tuberculosis (E and 85b), influenza (HA), myeloma antigen (F=M315) and also model antigens like OVA and mCherry were transiently transfected into Hek293E cells and the supernatant harvested and analyzed by ELISA. The ability of MIP1a to retain chemotactic activity when used as a targeting unit for heterodimers was analyzed. As shown in FIGS. 5a and 5b, supernatant from Hek293E cells transiently transfected with various vaccine molecules attracts CCR1+ and CCR5+ ESb-MP cells through transwell filters.

Figure 6:
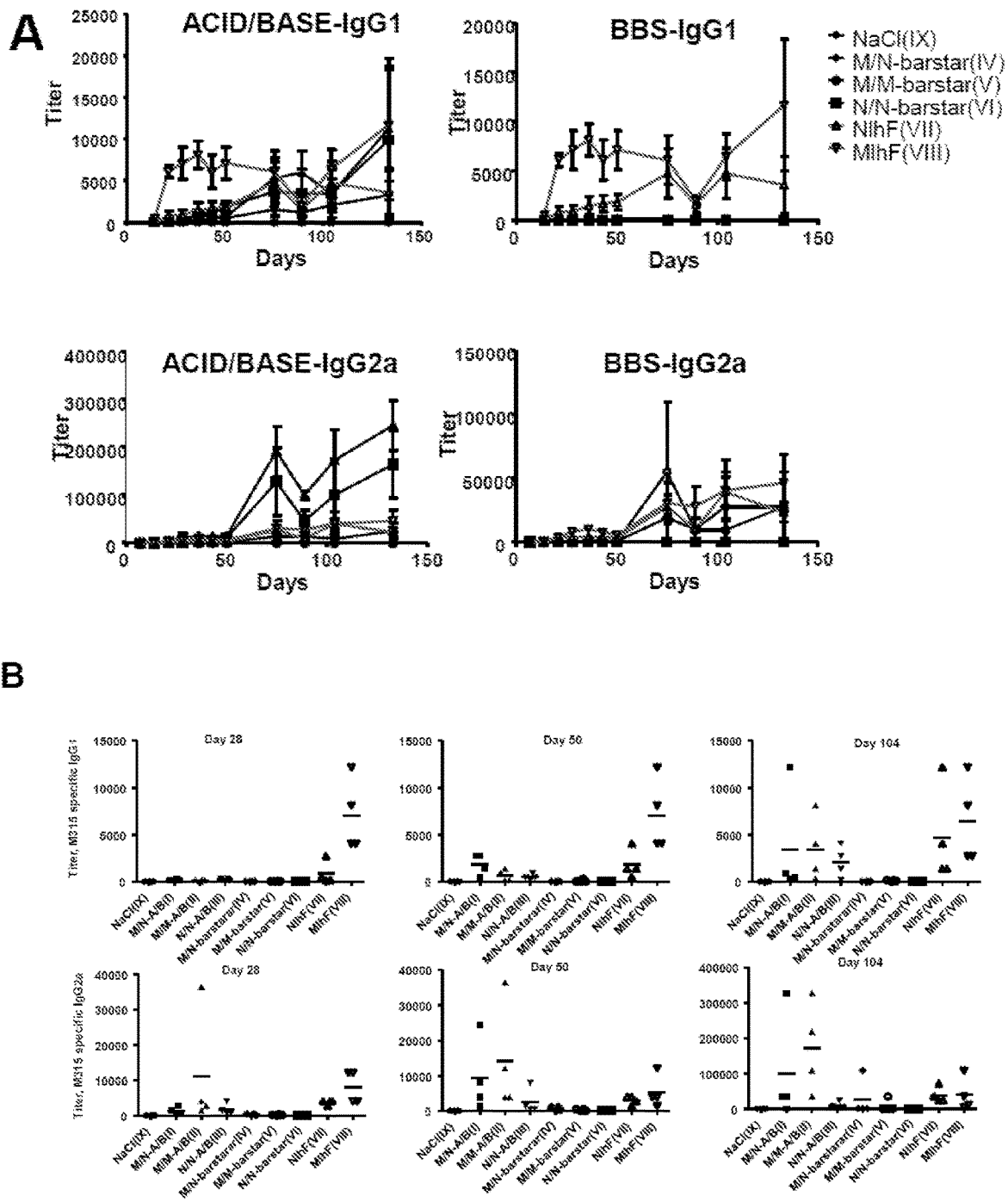
Figure 7:
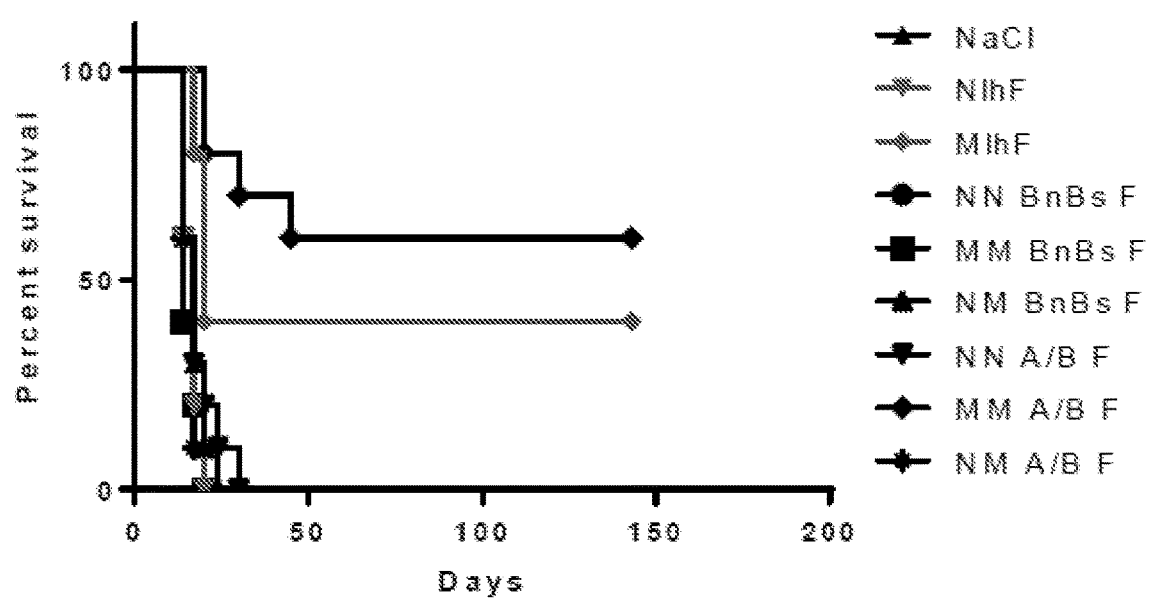

The vaccine molecules were also used in in vivo experiments. The DNA vaccine is administrated into the muscle of mice followed by electroporation to increase uptake of DNA and production of vaccine proteins secreted into the serum. FIG. 6 shows the results of M315-specific immune responses in mice immunized i.m. once and with a protein boost on day 62 with 50 µg M315. When compared to normal vaccibody, the IgG1 responses is slightly slower than vaccibody, but the IgG2a is slightly improved as compared to the vaccibody vaccine. As shown in FIG. 7, the immune response can be generated against MOPC315 tumor cells. Ten mice per group were vaccinated with 50 µg DNA per plasmid and 14 days after challenged with 100 000 MOPC315 tumor cells.

As can be seen from the data above, the Barnase-barstar heterodimer and the ACID/BASE heterodimer are efficiently expressed in vitro and in vivo with fusions proteins attached N-terminal and C-terminal. Both heterodimers were flexible as various targeting and antigenic units were expressed as fusion proteins within the heterodimer in vitro. Finally, MIP-1α targeting induced antigen-specific IgG1 and IgG2a responses with the ACID/BASE heterodimers, even better than homodimeric Vaccibody. Furthermore, the ACID/BASE heterodimer protected the mice against MOPC315 myeloma tumor, and two MIP-1α targeting units were necessary for the protection.

These data show that the heterodimeric vaccine molecules afford a flexible platform for development of novel DNA vaccines with increased potency.

Exemplary Construct Sequences

```
MIP1α-2ACID-M315 DNA sequence with intron (SEQ ID NO: 1):
MIP1α is from nucleotide: 050-256
Hinge: 666-716
ACID-ACID with linkers: 717-1022
Linker: 1023-1037
M315 antigen: 1038-1766
 001    GGGTGACAAT GACATCCACT TTGCCTTTCT CTCCACAGGT GTGCATTCCG

051    CGCCATATGG AGCTGACACC CCGACTGCCT GCTGCTTCTC CTACAGCCGG

101    AAGATTCCAC GCCAATTCAT CGTTGACTAT TTTGAAACCA GCAGCCTTTG

151    CTCCCAGCCA GGTGTCATTT TCCTGACTAA GAGAAACCGG CAGATCTGCG

201    CTGACTCCAA AGAGACCTGG GTCCAAGAAT ACATCACTGA CCTGGAACTG

251    AACGCTGGTG AGTCGTACGC TAGCAAGCTT GGCCAGCGCA GGGAGGGAGG

301    GTGTCTGCTG AAGCCAGGC TCAGCCCTCC TGCCTGGACG CATCCCGGCT

351    GTGCAGTCCC AGCCCAGGGC ACCAAGGCAG GCCCCGTCTG ACTCCTCACC

401    CGGAGGCCTC TGCCCGCCCC ACTCATGCTC AGGGAGAGGG TCTTCTGGCT

451    TTTTCCACCA GGCTCCGGGC AGGCACAGGC TGGATGCCCC TACCCCAGGC

501    CCTTCACACA CAGGGGCAGG TGCTGCGCTC AGAGCTGCCA AAAGCCATAT

551    CCAGGAGGAC CCTGCCCCTG ACCTAAGCCC ACCCCAAAGG CCAAACTCTC

601    TACTCACTCA GCTCAGACAC CTTCTCTCTT CCCAGATCTG AGTAACTCCC

651    AATCTTCTCT CTGCAGAGCT CAAAACCCCA CTTGGTGACA CAACTCACAC

701    ATGCCCACGG TGCCCAGGAG GTAGCAGCGG TGGAAAATTC GGCGGTTCCA

751    CTACAGCTCC ATCAGCTCAG CTCGAAAAAG AGCTCCAGGC CCTGGAGAAG

801    GAAAATGCAC AGCTGGAATG GGAGTTGCAA GCACTGGAAA AGGAACTGGC

851    TCAGGGAGGT GGTAGCGGAG GGTTAACCAA ATTCGGCGGT TCCACTACAG

901    CTCCATCAGC TCAGCTCGAA AAAGAGCTCC AGGCCCTGGA GAAGGAAAAT

951    GCACAGCTGG AATGGGAGTT GCAAGCACTG GAAAAGGAAC TGGCTCAGGG

1001    AGGTGGTAGC GGAGGGTTAA CCGGCCTCAG CGGCCTGGAT GTACAGCTTC

1051    AGGAGTCAGG ACCTGGCCTC GTGAAACCTT CTCAGTCTCT GTCTCTCACC

1101    TGCTCTGTCA CTGGCTACTC CATCACCAGT GGGTATTTCT GGAACTGGAT

1151    ACGGCAGTTT CCAGGAAACA AACTGGAATG GTTGGGCTTC ATAAAGTACG

1201    ACGGTAGCAA TGGCTACAAT CCATCTCTCA AAAATCGAGT TCCATCACT

1251    CGTGACACAT CTGAGAACCA GTTTTTCCTG AAGTTGAATT CTGTGACTAC

1301    TGAGGACACA GCTACATATT ACTGTGCCGG AGATAATGAT CACCTCTACT

1351    ACTTTGACTA CTGGGGCCAA GGCACCACTC TCACAGTCTC CTCAGGTGGA

1401    GGCGGATCTG GCGGAGGTGG CTCTGGCGGT GGCGGATCGC AGGCTGTTGT

1451    GACTCAGGAA TCTGCACTCA CCACATCACC TGGTGGAACA GTCATACTCA

1501    CTTGTCGCTC AAGTACTGGG GCTGTTACAA CTAGTAACTA TGCCAACTGG

1551    ATACAAGAAA AACCAGATCA TTTATTCACT GGTCTAATCG GTGGTACCAG

1601    CAACCGAGCT CCAGGTGTTC CTGTCAGATT CTCAGGCTCC CTGATTGGAG

1651    ACAAGGCTGC CCTCACCATC ACAGGGGCAC AGACTGAGGA TGATGCAATG

1701    TATTTCTGTG CTCTATGGTT CAGAAACCAT TTTGTTTTCG GCGGTGGAAC

1751    CAAGGTCACT GTCCTATGAG GCCTGCAGGG CCGGTCCGTC GACTCTAGAG
```

-continued

MIP1α-2ACID-M315 DNA sequence without intron (SEQ ID NO: 2):
**CTCCACAGGTGTGCATTCCGCGCCATATGGAGCTGACACCCCGACTGCCTGCT
GCTTCTCCTACAGCCGGAAGATTCCACGCCAATTCATCGTTGACTATTTTGAAA
CCAGCAGCCTTTGCTCCCAGCCAGGTGTCATTTTCCTGACTAAGAGAAACCGG
CAGATCTGCGCTGACTCCAAAGAGACCTGGGTCCAAGAATACATCACTGACCT
GGAACTGAACGCTGAGCTCAAAACCCCACTTGGTGACACAACTCACACATGCC
CACGGTGCCCAGGAGGTAGCAGCGGTGGAAAATTCGGCGGTTCCACTACAGCT
CCATCAGCTCAGCTCGAAAAAGAGCTCCAGGCCCTGGAGAAGGAAAATGCACA
GCTGGAATGGGAGTTGCAAGCACTGGAAAAGGAACTGGCTCAGGGAGGTGGT
AGCGGAGGGTTAACCAAATTCGGCGGTTCCACTACAGCTCCATCAGCTCAGCT
CGAAAAAGAGCTCCAGGCCCTGGAGAAGGAAAATGCACAGCTGGAATGGGAG
TTGCAAGCACTGGAAAAGGAACTGGCTCAGGGAGGTGGTAGCGGAGGGTTAA
CCGGCCTCAGCGGCCTGGATGTACAGCTTCAGGAGTCAGGACCTGGCCTCGTG
AAACCTTCTCAGTCTCTGTCTCTCACCTGCTCTGTCACTGGCTACTCCATCACC
AGTGGGTATTTCTGGAACTGGATACGGCAGTTTCCAGGAAACAAACTGGAATG
GTTGGGCTTCATAAAGTACGACGGTAGCAATGGCTACAATCCATCTCTCAAAA
ATCGAGTTTCCATCACTCGTGACACATCTGAGAACCAGTTTTTCCTGAAGTTGA
ATTCTGTGACTACTGAGGACACAGCTACATATTACTGTGCCGGAGATAATGAT
CACCTCTACTACTTTGACTACTGGGGCCAAGGCACCACTCTCACAGTCTCCTCA
GGTGGAGGCGGATCTGGCGGAGGTGGCTCTGGCGGTGGCGGATCGCAGGCTG
TTGTGACTCAGGAATCTGCACTCACCACATCACCTGGTGGAACAGTCATACTC
ACTTGTCGCTCAAGTACTGGGGCTGTTACAACTAGTAACTATGCCAACTGGAT
ACAAGAAAAACCAGATCATTTATTCACTGGTCTAATCGGTGGTACCAGCAACC
GAGCTCCAGGTGTTCCTGTCAGATTCTCAGGCTCCCTGATTGGAGACAAGGCT
GCCCTCACCATCACAGGGGCACAGACTGAGGATGATGCAATGTATTTCTGTG
CTCTATGGTTCAGAAACCATTTTGTTTTCGGCGGTGGAACCAAGGTCACTGTCC
TATGAG**

MIP1α-2ACID-M315 Amino Acid sequence (SEQ ID NO: 3):
MIP1α is from amino acid: 7-75
Hinge: 76-92
ACID-ACID with linkers: 93-194
Linker: 195-199
M315 antigen: 200-442

1 STGVHSAPYG ADTPTACCFS YSRKIPRQFI VDYFETSSLC SQPGVIFLTK RNRQICADSK

61 ETWVQEYITD LELNAELKTP LGDTTHTCPR CPGGSSGGKF GGSTTAPSAQ LEKELQALEK

121 ENAQLEWELQ ALEKELAQGG GSGGLTKFGG STTAPSAQLE KELQALEKEN AQLEWELQAL

181 EKELAQGGGS GGLTGLSGLD VQLQESGPGL VKPSQSLSLT CSVTGYSITS GYFWNWIRQF

241 PGNKLEWLGF IKYDGSNGYN PSLKNRVSIT RDTSENQFFL KLNSVTTEDT ATYYCAGDND

301 HLYYFDYWGQ GTTLTVSSGG GGSGGGGSGG GGSQAVVTQE SALTTSPGGT VILTCRSSTG

361 AVTTSNYANW IQEKPDHLFT GLIGGTSNRA PGVPVRFSGS LIGDKAALTI TGAQTEDDAM

421 YFCALWFRNH FVFGGGTKVT VL*

MIP1α-2BASE-M315 DNA sequence with intron (SEQ ID NO: 4):
MIP1α is from nucleotide: 050-256
Hinge: 666-716
BASE-BASE with linkers: 717-1022
Linker: 1023-1037
M315 antigen: 1038-1766

001 GGGTGACAAT GACATCCACT TTGCCTTTCT CTCCACAGGT GTGCATTCCG

051 CGCCATATGG AGCTGACACC CCGACTGCCT GCTGCTTCTC CTACAGCCGG

101 AAGATTCCAC GCCAATTCAT CGTTGACTAT TTTGAAACCA GCAGCCTTTG

151 CTCCCAGCCA GGTGTCATTT TCCTGACTAA GAGAAACCGG CAGATCTGCG

201 CTGACTCCAA AGAGACCTGG GTCCAAGAAT ACATCACTGA CCTGGAACTG

251 AACGCTGGTG AGTCGTACGC TAGCAAGCTT GGCCAGCGCA GGGAGGGAGG

301 GTGTCTGCTG GAAGCCAGGC TCAGCCCTCC TGCCTGGACG CATCCCGGCT

351 GTGCAGTCCC AGCCCAGGGC ACCAAGGCAG GCCCCGTCTG ACTCCTCACC

401 CGGAGGCCTC TGCCCGCCCC ACTCATGCTC AGGGAGAGGG TCTTCTGGCT

451 TTTTCCACCA GGCTCCGGGC AGGCACAGGC TGGATGCCCC TACCCCAGGC

501 CCTTCACACA CAGGGGCAGG TGCTGCGCTC AGAGCTGCCA AAGCCATAT

551 CCAGGAGGAC CCTGCCCCTG ACCTAAGCCC ACCCCAAAGG CCAAACTCTC

| | |
|---|---|
| 601 | TACTCACTCA GCTCAGACAC CTTCTCTCTT CCCAGATCTG AGTAACTCCC |
| 651 | AATCTTCTCT CTGCAGAGCT CAAAACCCCA CTTGGTGACA CAACTCACAC |
| 701 | ATGCCCACGG TGCCCAGGAG GTAGCAGCGG TGGAAAATTC GGCGGTTCCA |
| 751 | CTACAGCTCC ATCAGCTCAG TTGAAAAAGA AATTGCAAGC ACTGAAGAAA |
| 801 | AAGAACGCTC AGCTGAAGTG GAAACTTCAA GCCCTCAAGA AGAAACTCGC |
| 851 | CCAGGGAGGT GGTAGCGGAG GGTTAACCAA ATTCGGCGGT TCCACTACAG |
| 901 | CTCCATCAGC TCAGTTGAAA AAGAAATTGC AAGCACTGAA GAAAAGAAC |
| 951 | GCTCAGCTGA AGTGGAAACT TCAAGCCCTC AAGAAGAAAC TCGCCCAGGG |
| 1001 | AGGTGGTAGC GGAGGGTTAA CCGGCCTCAG CGGCCTGGAT GTACAGCTTC |
| 1051 | AGGAGTCAGG ACCTGGCCTC GTGAAACCTT CTCAGTCTCT GTCTCTCACC |
| 1101 | TGCTCTGTCA CTGGCTACTC CATCACCAGT GGGTATTTCT GGAACTGGAT |
| 1151 | ACGGCAGTTT CCAGGAAACA AACTGGAATG GTTGGGCTTC ATAAAGTACG |
| 1201 | ACGGTAGCAA TGGCTACAAT CCATCTCTCA AAAATCGAGT TTCCATCACT |
| 1251 | CGTGACACAT CTGAGAACCA GTTTTTCCTG AAGTTGAATT CTGTGACTAC |
| 1301 | TGAGGACACA GCTACATATT ACTGTGCCGG AGATAATGAT CACCTCTACT |
| 1351 | ACTTTGACTA CTGGGGCCAA GGCACCACTC TCACAGTCTC CTCAGGTGGA |
| 1401 | GGCGGATCTG GCGGAGGTGG CTCTGGCGGT GGCGGATCGC AGGCTGTTGT |
| 1451 | GACTCAGGAA TCTGCACTCA CCACATCACC TGGTGGAACA GTCATACTCA |
| 1501 | CTTGTCGCTC AAGTACTGGG GCTGTTACAA CTAGTAACTA TGCCAACTGG |
| 1551 | ATACAAGAAA AACCAGATCA TTTATTCACT GGTCTAATCG GTGGTACCAG |
| 1601 | CAACCGAGCT CCAGGTGTTC CTGTCAGATT CTCAGGCTCC CTGATTGGAG |
| 1651 | ACAAGGCTGC CCTCACCATC ACAGGGGCAC AGACTGAGGA TGATGCAATG |
| 1701 | TATTTCTGTG CTCTATGGTT CAGAAACCAT TTTGTTTTCG GCGGTGGAAC |
| 1751 | CAAGGTCACT GTCCTATGAG GCCTGCAGGG CCGGTCCGTC GACTCTAGAG |

MIP1α-2BASE-M315 DNA sequence withOut intron (SEQ ID NO: 5):
GTGCATTCCGCGCCATATGGAGCTGACACCCCGACTGCCTGCTGCTTCTCCTA
CAGCCGGAAGATTCCACGCCAATTCATCGTTGACTATTTTGAAACCAGCAGCC
TTTGCTCCCAGCCAGGTGTCATTTTCCTGACTAAGAGAAACCGGCAGATCGC
GCTGACTCCAAAGAGACCTGGGTCCAAGAATACATCACTGACCTGGAACTGAA
CGCTGAGCTCAAAACCCCACTTGGTGACACAACTCACACATGCCCACGGTGCC
CAGGAGGTAGCAGCGGTGGAAAATTCGGCGGTTCCACTACAGCTCCATCAGCT
CAGTTGAAAAAGAAATTGCAAGCACTGAAGAAAAGAACGCTCAGCTGAAGTG
GAAACTTCAAGCCCTCAAGAAGAAACTCGCCCAGGGAGGTGGTAGCGGAGGG
TTAACCAAATTCGGCGGTTCCACTACAGCTCCATCAGCTCAGTTGAAAAAGAA
ATTGCAAGCACTGAAGAAAAGAACGCTCAGCTGAAGTGGAAACTTCAAGCCC
TCAAGAAGAAACTCGCCCAGGGAGGTGGTAGCGGAGGGTTAACCGGCCTCAG
CGGCCTGGATGTACAGCTTCAGGAGTCAGGACCTGGCCTCGTGAAACCTTCTC
AGTCTCTGTCTCTCACCTGCTCTGTCACTGGCTACTCCATCACCAGTGGGTATT
TCTGGAACTGGATACGGCAGTTTCCAGGAAACAAACTGGAATGGTTGGGCTTC
ATAAAGTACGACGGTAGCAATGGCTACAATCCATCTCTCAAAAATCGAGTTTCC
ATCACTCGTGACACATCTGAGAACCAGTTTTTCCTGAAGTTGAATTCTGTGACT
ACTGAGGACACAGCTACATATTACTGTGCCGGAGATAATGATCACCTCTACTA
CTTTGACTACTGGGGCCAAGGCACCACTCTCACAGTCTCCTCAGGTGGAGGCG
GATCTGGCGGAGGTGGCTCTGGCGGTGGCGGATCGCAGGCTGTTGTGACTCA
GGAATCTGCACTCACCACATCACCTGGTGGAACAGTCATACTCACTTGTCGCT
CAAGTACTGGGGCTGTTACAACTAGTAACTATGCCAACTGGATACAAGAAAA
CCAGATCATTTATTCACTGGTCTAATCGGTGGTACCAGCAACCGAGCTCCAGG
TGTTCCTGTCAGATTCTCAGGCTCCCTGATTGGAGACAAGGCTGCCCTCACCA
TCACAGGGGCACAGACTGAGGATGATGCAATGTATTTCTGTGCTCTATGGTTC
AGAAACCATTTTGTTTTCGGCGGTGGAACCAAGGTCACTGTCCTATGAG MIP1α-2BASE-M315 Amino Acid sequence (SEQ ID NO: 6):
MIP1α is from amino acid: 4-72
Hinge: 73-89
ACID-ACID with linkers: 90-191
Linker: 192-196
M315 antigen: 197-439

```
  1    VHSAPYGADT PTACCFSYSR KIPRQFIVDY FETSSLCSQP GVIFLTKRNR

61    QICADSKETW

121    VQEYITDLEL NAELKTPLGD TTHTCPRCPG GSSGGKFGGS TTAPSAQLKK

181    KLQALKKKNA

241    QLKWKLQALK KKLAQGGGSG GLTKFGGSTT APSAQLKKKL QALKKKNAQL

301    KWKLQALKKK

361    LAQGGGSGGL TGLSGLDVQL QESGPGLVKP SQSLSLTCSV TGYSITSGYF

421    WNWIRQFPGN
       KLEWLGFIKY DGSNGYNPSL KNRVSITRDT SENQFFLKLN SVTTEDTATY
       YCAGDNDHLY
       YFDYWGQGTT LTVSSGGGGS GGGGSGGGGS QAVVTQESAL TTSPGGTVIL
       TCRSSTGAVT
       TSNYANWIQE KPDHLFTGLI GGTSNRAPGV PVRFSGSLIG DKAALTITGA
       QTEDDAMYFC
       ALWFRNHFVF GGGTKVTVL*
```

Sequence of scFv$^{M315}$ the mutiple myeloma antigen used in heterodimers.
SEQ ID NO: 7. Amino acid sequence: V$_H$-linker-V$_L$
DVQLQESGPGLVKPSQSLSLTCSVTGYSITSGYFWNWIRQFPGNKLEWLGFIKYDGSNG
YNPSLKNRVSITRDTSENQFFLKLNVTTEDTATYYCAGDNDHLYYFDYWGQGTTLTVS
SGGGGSGGGGSGGGGSQAVVTQESALTTSPGGTVILTCRSSTGAVTTSNYANWIQEKPD
HLFTGLIGGTSNRAPGVPVRFSGSLIGDKAALTITGAQTEDDAMYFCALWFRNHFVFGG
GTKVTVL SEQ ID NO: 8. DNA: V$_H$-linker-V$_L$
GATGTACAGCTTCAGGAGTCAGGACCTGGCCTCGTGAAACCTTCTCAGTCTCT
GTCTCTCACCTGCTCTGTCACTGGCTACTCCATCACCAGTGGGTATTTCTGGAA
CTGGATACGGCAGTTTCCAGGAAACAAACTGGAATGGTTGGGCTTCATAAAAT
ACGACGGTAGCAATGGCTACAATCCATCTCTCAAAAATCGAGTTTCCATCACTC
GTGACACATCTGAGAACCAGTTTTTCCTGAAGTTGAATTCTGTGACTACTGAGG
ACACAGCTACATATTACTGTGCCGAGATAATGATCACCTCTACTACTTTGACT
ACTGGGGCCAAGGCACCACTCTCACAGTCTCCTCAGGTGGAGGCGGATCTGGC
GGAGGTGGCTCTGGCGGTGGCGGATCGCAGGCTGTTGTGACTCAGGAATCTG
CACTCACCACATCACCTGGTGGAACAGTCATACTCACTTGTCGCTCAAGTACTG
GGGCTGTTACAACTAGTAACTATGCCAACTGGATACAAGAAAAACCAGATCAT
TTATTCACTGGTCTAATCGGTGGTACCAGCAACCGAGCTCCAGGTGTTCCTGT
CAGATTCTCAGGCTCCCTGATTGGAGACAAGGCTGCCCTCACCATCACAGGGG
CACAGACTGAGGATGATGCAATGTATTTCTGTGCTCTATGGTTCAGAAACCATT
TTGTTTTCGGCGGTGGAACCAAGGTCACTGTCCTATGAG Sequence of scFv$^{420}$-the lymphoma antigen used in the heterodimer.
Linker before VH is underlined and linker between VH and VL is italic.
DNA SEQ is SEQ ID NO: 9, AMINO ACID SEQ is SEQ ID NO: 10

```
1301    ACGCAGAAGA GCCTCTCCCT GTCTCCGGGT AAAGGCCTCG GTGGCCTGAT
        T  Q  K  S  L  S  L  S  P  G  K  G  L  G  G  L  M  Frame 2

1351    GGTCCAACTG CAGCAGTCAG GGCCTGACCT TGTGAAACCT GGGATGTCCG
        V  Q  L  Q  Q  S  G  P  D  L  V  K  P  G  M  S  V  Frame 2

1401    TGAAACTGTC CTGTAAGACT TTGGGTTACA ATTTCTCCGA CAAGTGGATT
        K  L  S  C  K  T  L  G  Y  N  F  S  D  K  W  I  Frame 2

1451    CACTGGATTA AACAGAAGCC TGGCCGAGGC CTTGAATGGG TTGGAAGGAT
        H  W  I  K  Q  K  P  G  R  G  L  E  W  V  G  R  I  Frame 2

1501    TGATCCTTCT AACGGTGATA CTGACTATAA TGCGGACTTC AAGACCCCGG
        D  P  S  N  G  D  T  D  Y  N  A  D  F  K  T  P  Frame 2

1551    CCACACTAAC TGTTGACAGA CCCTCCAACA CAGCCTACTT AGAACTCAAC
        T  L  T  V  D  R  P  S  N  T  A  Y  L  E  L  N  Frame 2

1601    AACCTGACAT CTGGGGACTC TGCGGTCTAT TATTGTTCAA TATCGGGTGA
        N  L  T  S  G  D  S  A  V  Y  Y  C  S  I  S  G  D  Frame 2
```

```
1651    TTATTCCGCC TGCGACTATT GGGGCCAAGG TACCGAACTC ACAGTCTCCT
        Y  S  A  C  D  Y  W  G  Q  G  T  E  L  T  V  S  S  Frame 2

1701    CAGGTGGAGG TGGCTCTGGC GGTGGCGGAT CGGGAGGAGG CGGT TCTGAT
         G  G  G  S  G  G  G  G  S  G  G  G  G  S  D  Frame 2

1751    GTTGTGATGA CGCAGACTCC ACTCTCCCTG GCCGTCAGTC TTGGAGATCA
        V  V  M  T  Q  T  P  L  S  L  A  V  S  L  G  D  H  Frame 2

1801    CGTGAAAATG TCTTGTAGAT GTAATCAGAG CCTTGTAAAC AGTCATGGAG
        V  K  M  S  C  R  C  N  Q  S  L  V  N  S  H  G  D  Frame 2

1851    ACTCCTTTTT ACACTGGTTT CTGCAGAAGC CAGGCCAGTC TCCAAAACTC
        S  F  L  H  W  F  L  Q  K  P  G  Q  S  P  K  L  Frame 2

1901    CTGATCTACA AGGTTTCCAG CCGATTTTTT GGGGTCCCAG AGAGGTTCAG
        L  I  Y  K  V  S  S  R  F  F  G  V  P  E  R  F  S  Frame 2

1951    TGGCAGTGGT TCAGGGACAG ATTTCACACT CGAGATCAGT CGAGTGGAGG
        G  S  G  S  G  T  D  F  T  L  E  I  S  R  V  E  A  Frame 2

2001    CTGAGGATCT GGGAATTTAT TTCTGTTCTC AAGGTGCACA TGTTCCGTGG
        E  D  L  G  I  Y  F  C  S  Q  G  A  H  V  P  W  Frame 2
                                 SfiI 2051    ACGTTCGGTG GAGGCACAAA GCTGGAAGTC AAATGAGGCC TGCAGGGCCG
        T  F  G  G  G  T  K  L  E  V  K  *  Frame 2
                  BamHI

2101    GTCCGTCGAC TCTAGAGGAT CCACTAGTAA CGGCCGCCAG TGTGCTGGAA

Amino acid sequence of the A20 antigen:
VHA20-VLA20
SEQ ID NO: 11 VH-Linker-VL
MVQLQQSGPDLVKPGMSVKLSCKTLGYNFSDKWIHWIKQKPGRGLEWVGRIDPSNGD
TDYNADFKTPATLTVDRPSNTAYLELNNLTSGDSAVYYCSISGDYSACDYWGQGTELT
VSSGGGGSGGGGSGGGGSDVVMTQTPLSLAVSLGDHVKMSCRCNQSLVNSHGDSFLH
WFLQKPGQSPKLLIYKVSSRFFGVPERFSGSGSGTDFTLEISRVEAEDLGIYFCSQGAHVP
WTFGGGTKLEVK
```

Example 2. Bivalency of Targeted DNA Vaccines Increases B-Cell Mediated Responses Multivalent antigens are able to induce cross links between BCR on the B cell membrane, which is thought to be essential in B cell activation. Early B cell activation models described that these cross links are needed to activate B cells (16, 17). Other models for efficient B cell activation have been described recently, each of them incorporating valency as an important factor (17-20). Both with in vitro and in vivo models it has been shown that multivalent antigens induce more potent B cell signaling and antibody responses, but that monovalent antigens are able to activate B cell responses as well (21-28).

DNA vaccines offer a number of advantages over more traditional vaccines, but their immunogenicity in larger animals has been poor (29, 30). One efficient strategy to improve immune responses upon DNA vaccination is to directly target antigen to APC by genetic fusion of antigen to cytokines or single chain variable fragments specific for molecules on the APC surface (31-40).

This example demonstrates the value of antigen valency in the setting of targeted vaccines with different antigens. Monovalent and bivalent DNA vaccines that are targeted to MHCII on the APC were synthesized. These vaccines encode asymmetrical heterodimers that carried either two identical antigens in bivalent vaccines, or two divergent antigens in monovalent vaccines. The exemplary antigens utilized in this example are HA from two different influenza strains A/PR/8/34 and A/California/07/09, and single chain Fv derived from the tumor-specific immunoglobulins secreted by the murine B cell lymphomas MOPC315 and A20. The results indicate that bivalency of an antigen is an important vaccine attribute in the induction of efficient B cell responses.

The data are presented in FIGS. 8-12. FIG. 8A-E provides data related to design and characterization of heterodimeric vaccine molecules. A schematic depiction of the heterodimeric molecules and constructs is provided. FIG. 8A. A sequence alignment for the PR8 and Ca107 HA sequences is provided in FIG. 15. In these exemplary vaccine constructs, hemagglutinin (HA) from influenza H1N1 virus PR8 or Ca107 is targeted to antigen presenting cells with single chain FV specific for mouse MHC class II or hapten NIP as non-binding control. Heterodimers are formed through acid/base interactions between two alpha helices of a leucine zipper motif, enriched with either acidic or basic amino acids. Targeting units and antigenic units are placed on either end of the ACID or BASE dimerization units. DNA cassettes are expressed under a CMV promotor and contain the leader sequence of the pLNOH2 vector, indicated with L. Vectors with ACID and BASE constructs are co-transfected to express heterodimeric vaccine proteins. FIG. 8B. HEK 293E cells were co-transfected with ACID and BASE constructs and supernatant was analyzed by sandwich ELISA. Antigenic arms and dimerization units were detected with antiHA (PR8) and antiHA (Ca107) mAb, and mAb specific for the ACID/BASE motif (2H11)(26). FIG. 8C. Vaccine heterodimers in supernatant were detected on a western blot with biotinylated 2H11. FIG. 8D. Molecular sizes are indicated. Fibroblasts transfected with mouse MHCII (I-Ex and I-Ed) were incubated with non-targeted heterodimeric vaccine proteins containing two HA of PR8, or with MHCII targeted equivalents in undiluted form or in dilutions of 1 to 3 and 1 to 9 in cell medium. FIG. 8E. Bound vaccine proteins are stained with biotinylated αHA (PR8) and detected by streptavidin-PE with flow cytometry.

FIGS. 9A-I present data demonstrating that bivalency of heterodimeric vaccine molecules increases IgG titers in mice. Balb/c mice were vaccinated by intramuscular injection with 10 μg DNA plasmid (5 μg of each ACID and BASE plasmid) followed by electroporation (n=6/group). See FIGS. 9A-F. IgG, IgG1 and IgG2a responses specific for HA (PR8)(A-C) and HA (Ca107) (D-F) were analyzed by ELISA. (G-H) Balb/c mice were vaccinated by intradermal injection with 50 μg DNA (25 μg of each ACID and BASE plasmid) on the lower back, immediately followed by electroporation (n=6/group). Total IgG responses towards HA (PR8) (FIG. 9G) and HA (Ca107) (FIG. 9H) were analyzed. Balb/c mice were vaccinated by i.m. injection of varied DNA doses of bivalent or monovalent vaccine carrying the HA (PR8) antigen. See FIG. 9I. Total IgG specific for HA (PR8) was analyzed at week 6. Titers are defined as the highest serum dilution that produced an absorbance above background. Background absorbance was determined as twice the mean absorbance for signals from the serum of mice vaccinated with NaCl. Mean titers ±SEM are given. Significance is shown where bivalent vaccines outperformed monovalent vaccines. *P<0.05; **P<0.01. Mann Whitney.

FIGS. 10A-E present data showing antibody titers after vaccination with heterodimeric antitumor vaccine molecules of the present invention. Heterodimeric DNA vaccines were designed to carry anti-tumor antigens. FIG. 10A. Tumor antigens were tumor-specific immunoglobulins secreted by the murine B cell lymphomas MOPC315 (annotated M315) and A20. One vaccine was generated to carry a stop codon to form a monovalent vaccine with M315. Balb/c mice were vaccinated with heterodimeric anti-tumor vaccines. Mice received an intramuscular injection with 100 μg DNA plasmid (50 μg of each ACID and BASE plasmid) (n=6/group), followed by electroporation. IgG1 and IgG2a responses specific for A20 (FIGS. 10B-C) and M315 (FIGS. 10D-E) tumor antigens were analyzed by ELISA. Titers are defined as the highest serum dilution that produced an absorbance above background. Background absorbance was determined as twice the mean absorbance for signals from serum of mice vaccinated with NaCl. Mean titers ±SEM are given. Significance is shown to compare bivalent versus monovalent vaccines. *P<0.05; **P<0.01; Mann Whitney.

FIGS. 11A-F provide data showing that bivalent DNA vaccines completely protect mice against homologous H1N1 influenza infection. Balb/c mice were vaccinated by intramuscular injection with 100 μg DNA plasmid (50 μg of each ACID and BASE plasmid), followed by electroporation (n=6/group). After 14 days mice were challenged with influenza virus from strains PR8 with 5×LD50 (FIGS. 11 A and B) or 50×LD50 (FIGS. 11 C and D). Balb/c mice were vaccinated as described above (n=6/group). From day 12, αCD4 and αCD8 mAb were injected intraperitoneally every second day. A control group received isotype matched mAb after vaccination with aMHCII—Ca107/Ca107, shown in blue with open circles. Mice were challenged with PR8 influenza virus (5×LD50) at day 14 after vaccination. Mean weight loss ±SEM and survival after infection are shown for each experiment. FIGS. 11 A-E. Significance is shown for the comparison of bivalent versus monovalent vaccines. *P<0.05; P<0.01; *P<0.001 Mann Whitney and Mantel Cox.

FIGS. 12A-C provide data showing bivalency of heterodimeric vaccine molecules increases antigen specific germinal centers and B cell population in bone marrow. Balb/c mice were vaccinated by intradermal injection of 50 μg DNA plasmid (25 μg of each ACID and BASE plasmid), directly followed by electroporation (n=3). After three weeks draining lymph nodes (iliac or inguinal) and bone marrow from the tibia were harvested. (FIGS. A-B) Single cell suspensions from lymph nodes were stained with serially diluted HA probe and gated on GC B-cells (GL7+CD38lo) and analyzed of binding in flow cytometry. (FIG. A) Dilution curve of rHA probe fitted with non-linear regression. (FIG. B) Representation of individual mice with 200 nM rHA probe. (FIG. C) Cell suspensions from the bone marrow were analyzed with a B-cell ELISPOT to detect PR8 or Ca107 specific B cells. *p<0.05 and **p<0.01, unpaired two tailed student's t-test.

Figure 13:
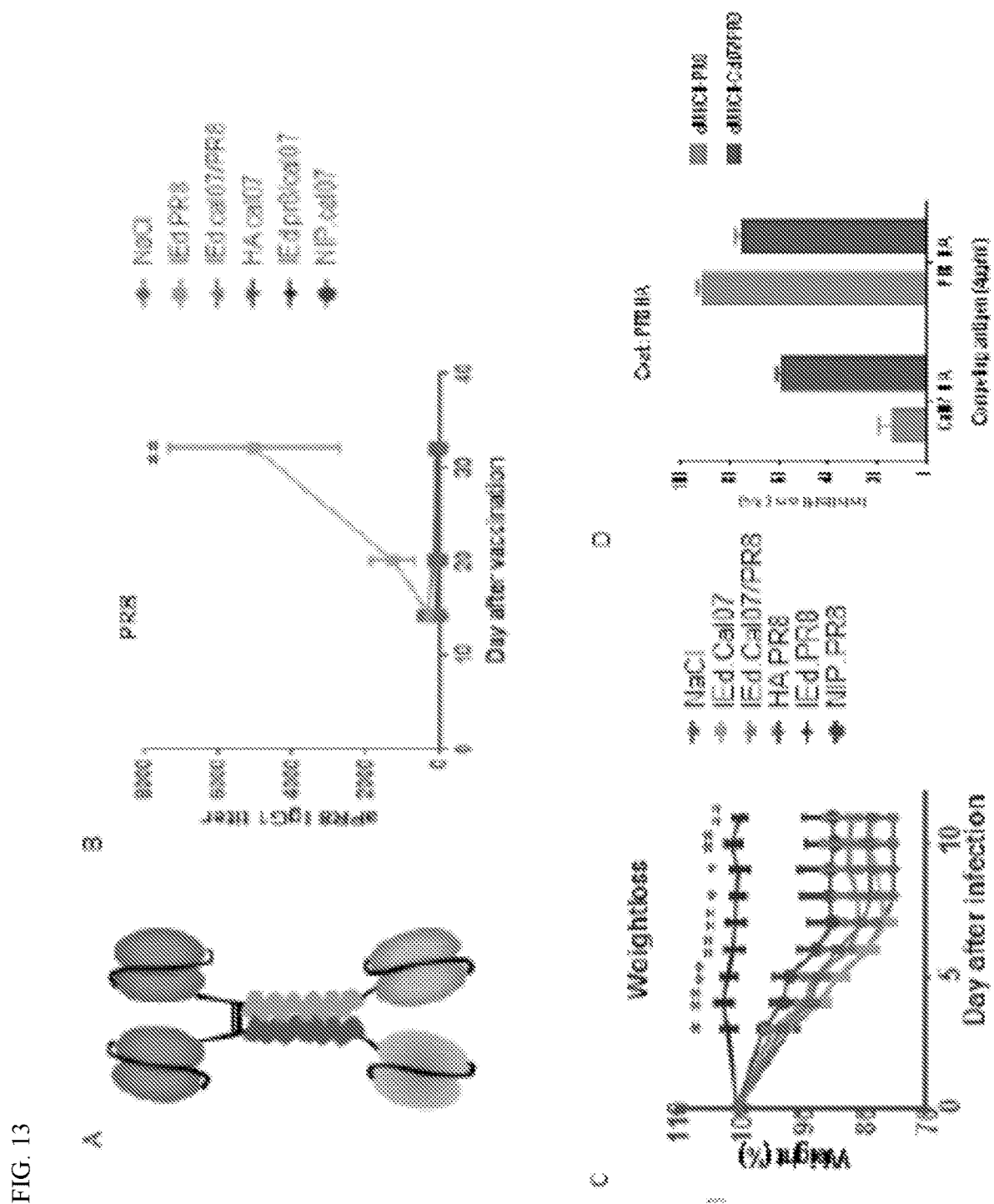

FIGS. 13A-D provide additional data showing that heterodimers with two variants of the hemagglutinin, HA, named PR8 and Ca107 (mixed), showed a clear effect of bivalency both in respect of humoral responses as well as for protecting BALB/c mice in a challenge model for PR8. Both antigens show induction of antigen-specific antibodies in the mice. The heterodimeric ACID/BASE targeting vaccine is schematically depicted in FIG. 13A. Vaccination of balb/c mice gave higher PR8-specific IgG1 for bivalent molecules than monovalent molecules. See FIG. 13 B. Only bivalent heterodimer induced full protection in a PR8 challenge. See FIG. 13C. In addition, a tendency of increased competition in inhibitory ELISA suggested the mixed vaccine to induce more cross-binding antibodies (FIG. 13 D). FIG. 13 D provides results of a competing ELISA where PR8 is used as coat and the sera from vaccinated mice is competed with Ca107 (Ca107/PR8 inhibited more than Ca107/Ca107) or with PR8 (Ca107/PR8 less inhibited than PR8/PR8).

Example 3—Protection Against Tumor Formation in Bone Marrow

This example describes experiments that show that the ACID/BASE heterodimeric vaccine protect mice against the bone marrow homing MOPC.315 tumor model in mice (MOPC.315BM) (Hofgaard, P. O., et al., 2012. PLoS One 7: e51892).

Figures 15, 16:
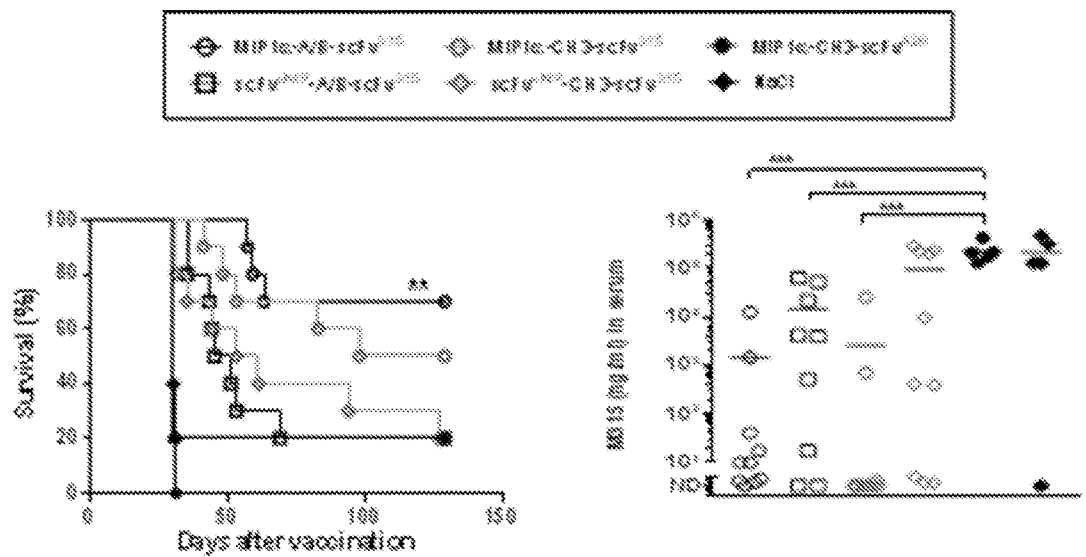

FIG. 16 shows that ACID/BASE heterodimeric DNA vaccines induce protection against bone marrow MOPC.315.BM tumor after a single vaccination in BALB/c mice. Mice were vaccinated with 50 μg DNA i.m. in each quadriceps followed by electroporation of the injection site. After 14 days (n=10/group, n=5 for NaCl group), mice were challenged i.v. with 104 MOPC.315.BM (bone marrow) cells. Mice reaching the endpoint paraplegia, were euthanized. Survival curves of the various vaccines compared to antigen control (MIP1α-CH3-scFvA20) and NaCl vaccinated mice. (p<0.01, Mantel-Cox analysis, MIP1α-targeted groups compared with nontargeted scFv$^{\alpha NIP}$-A/B-scFv315) are shown in FIG. 16A. Blood samples were harvested on day 36 after challenge and analysed for the tumor-specific antigen M315 in ELISA (nondetectable=ND, mean shown as a bar, *p<0.001, Mann-Whitney, two-tailed) (FIG. 16B).

Figure 17:
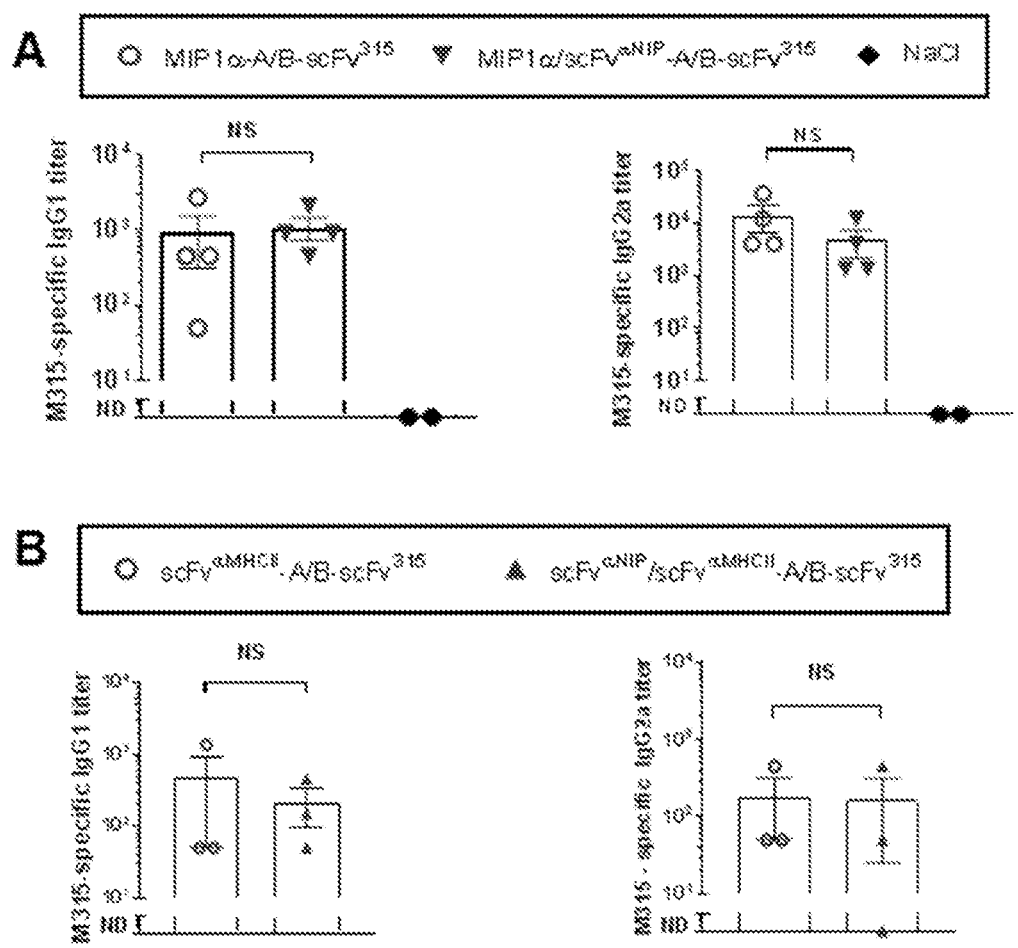
FIG. 17 shows that one targeting unit in the ACID/BASE heterodimeric vaccine is sufficient for antigen-specific IgG1 and IgG2a responses in vivo.
Figure 19:
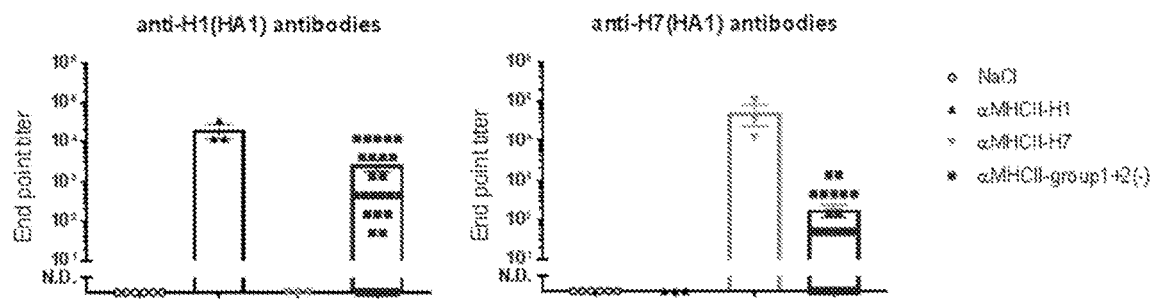
FIG. 19 shows that vaccination with a HA mix vaccine induces antibody against heterologous HA strains (HA' not included in the mix).
Figure 20:
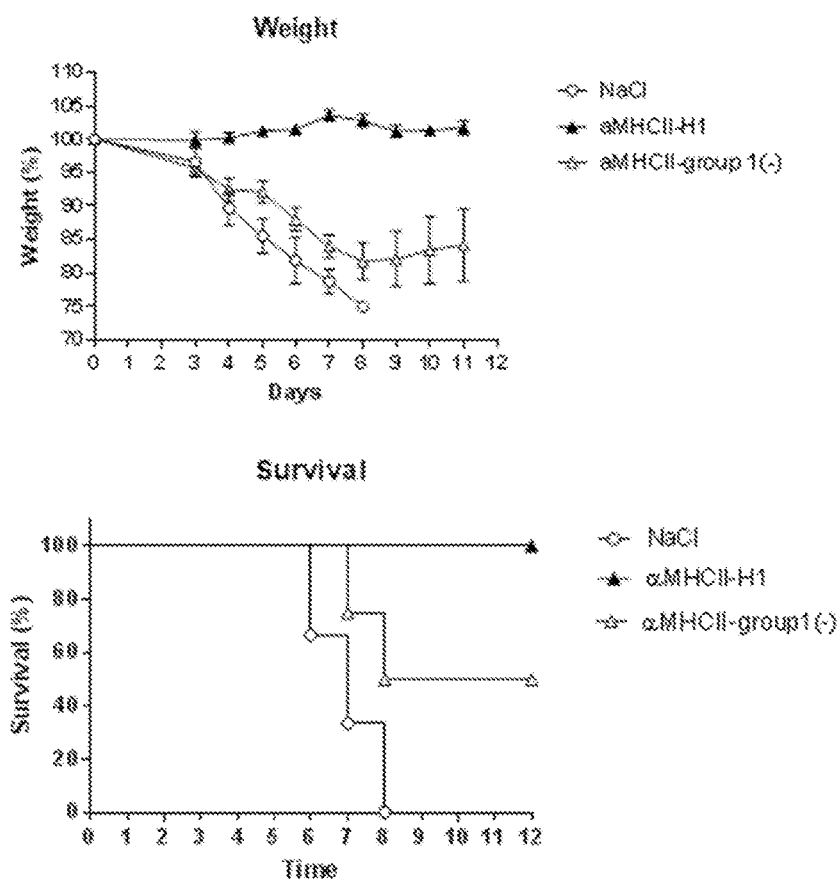
FIG. 20 shows that vaccination with HA mix (lacking H1) gives partial protection against H1 challenge.

FIG. 17 shows that one targeting unit in the ACID/BASE heterodimeric vaccine is sufficient for antigen-specific IgG1 and IgG2a responses in vivo. BALB/c mice were vaccinated with 50 μg DNA i.m. with A/B heterodimeric vaccines as indicated in FIG. 17. 36 days (A, n=4/group) or 14 days (B, n=3/group) after vaccination the mice were bled and M315-specific IgG1 and IgG2a were analysed in the sera (nondetectable=ND, mean±SEM, nonsignificant=ns, Mann Whitney).

In summary, results are shown in FIGS. 16 and 17 and demonstrate that the ACID/BASE heterodimer can protect against a mice model homing to the bone marrow, as seen in human patients, where the myeloma tumor homes to the bone marrow (FIG. 16) and that one targeting is sufficient for the ACID/BASE heterodimer to induce antigen-specific antibody responses (FIG. 17).

Example 4—Mixed Vaccines

This example described ACID/BASE heterodimers that were tested as a mixed vaccine including 18 subtype of hemagglutinin (HA).

TABLE 1

Description of HA mix vaccines used in this study

| VACCINE ANTIGENS | ACID/BASE distribution | VACCINE NAME | H1 | H7 |
|---|---|---|---|---|
| Group 1 HA | Acid: H8, H9, H11, H12, H13, H16 Base: (H1) H2, H5, H6, H17, H18 | αMH 9. Hawiger, D., et al., *Dendritic cells induce peripheral T cell unresponsiveness under steady state conditions in vivo.* J Exp Med, 2001. 194(6): p. 769-79.
10. Ruffini, P. A., et al., *Genetic fusions with viral chemokines target delivery of nonimmunogenic antigen to trigger antitumor immunity independent of chemotaxis.* J Leukoc Biol, 2004. 76(1): p. 77-85.
11. Demangel, C., et al., *Single chain antibody fragments for the selective targeting of antigens to dendritic cells.* Mol Immunol, 2005. 42(8): p. 979-85.
12. Fredriksen, A. B., I. Sandlie, and B. Bogen, *DNA vaccines increase immunogenicity of idiotypic tumor antigen by targeting novel fusion proteins to antigen presenting cells.* Mol Ther, 2006. 13(4): p. 776-85.
13. Schjetne, K. W., A. B. Fredriksen, and B. Bogen, *Delivery of antigen to CD40 induces protective immune responses against tumors.* J Immunol, 2007. 178(7): p. 4169-76.
14. Nchinda, G., et al., *The efficacy of DNA vaccination is enhanced in mice by targeting the encoded protein to dendritic cells.* J Clin Invest, 2008. 118(4): p. 1427-36.
15. Fredriksen, A. B. and B. Bogen, *Chemokine-idiotype fusion DNA vaccines are potentiated by bivalency and xenogeneic sequences.* Blood, 2007. 110(6): p. 1797-805.
16. Tolar P, S. K. P. A conformation-induced oligomerization model for B cell receptor microclustering and signaling. Curr Top Microbiol Immunol. 2010; 340:155-69.
17. Avalos A M, H. L. P. Early BCR Events and Antigen Capture, Processing, and Loading on MHC Class II on B Cells. Front Immunol. 2014; 5(92):5.
18. Yang J, Reth M. The dissociation activation model of B cell antigen receptor triggering. FEBS lett. 2010; 584(24): 4872-77.
19. Treanor B. B-cell receptor: from resting state to activate. Immunology. 2012; 136(1):7.
20. Treanor B, Depoil D, Gonzalez-Granja A, Barral P, Weber M, Dushek 0, et al. The Membrane Skeleton Controls Diffusion Dynamics and Signaling through the B Cell Receptor. Immunity. 2010; 32(2):187-99.
21. Kim Y M, Pan J Y, G. A. K, V. P, M. B, H. L. P. Monovalent ligation of the B cell receptor induces receptor activation but fails to promote antigen presentation. Proc Natl Acad Sci USA. 2006; 103(9):6.
22. Mukherjee S, Zhu J, Zikherman J, Parameswaran R, Kadlecek T A, Wang Q, et al. Monovalent and multivalent ligation of the B cell receptor exhibit differential dependence upon Syk and Src family kinases. Sci Signal 2013; 6(256):doi 10.1126/scisignal.2003220.
23. Volkmann C, Brings N, Becker M, Hobeika E, Yang J, Reth M. Molecular requirements of the B-cell antigen receptor for sensing monovalent antigens. EMBO J. 2016; 35(21):2371-81.
24. Minguet S, Dopfer E P, W. W. S. Low-valency, but not monovalent, antigens trigger the B-cell antigen receptor (BCR). Int Immunol. 2010; 22(3):8.
25. Ubelhart R, Hug E, Bach M P, Wossning T, Minden M D-v, Horn A H, et al. Responsiveness of B cells is regulated by the hinge region of IgD. Nat Immunol. 2015; 16(5):534-43.
26. Puffer E B, Pontrello J K, Hollenbeck J J, Kink J A, Kiessling L L. Activating B cell signaling with defined multivalent ligands. ACS Chem Biol. 2007; 2(4):252-62.
27. Q. Qina, Yina Z, Wua X, Haasb K M, Huanga X. Valency and density matter: Deciphering impacts of immunogen structures on immune responses against a tumor associated carbohydrate antigen using synthetic glycopolymers. Biomaterials. 2016; 101:189-98.
28. Schelling M E, Silverman P H. The effect of route of injection upon the development of circulating antibody in response to a variety of antigens. Immunology. 1968; 14(6):781-5.
29. Kutzler M A, Weiner D B. DNA vaccines: ready for prime time? Nat Rev Genet. 2008; 9(10):776-88.
30. Ferraro B, Morrow M P, Hutnick N A, Shin T H, Lucke C E, Weiner D B. Clinical applications of DNA vaccines: current progress. Clin Infect Dis. 2011; 53(3):296-302.
31. B. Alvarez, T. Poderoso, F. Alonso, A. Ezquerra, J. Dominguez, Revilla C. Antigen targeting to APC: From mice to veterinary species. Dev Comp Immunol. 2013; 41(2):153-63.
32. Wang G, Pan L, Zhan Y. Approaches to improved targeting of DNA vaccines. Hum Vaccin. 2011; 7(12): 1271-81.
33. Fredriksen A B, Sandlie I, bogen B. Targeted DNA vaccines for enhanced induction of idiotype-specific B and T cells. Front Oncol. 2012; 2(154).
34. Kastenmüller W, Kastenmüller K, Kurts C, Seder R A. Dendritic cell-targeted vaccines—hope or hype? Nat Rev Immunol. 2014; 14(10):705-11.
35. Fredriksen A B, Bogen B. Chemokine-idiotype fusion DNA vaccines are potentiated by bivalency and xenogeneic sequences. Blood. 2007; 110(6):10.
36. Fredriksen A B, Sandlie I, Bogen B. DNA vaccines increase immunogenicity of idiotypic tumor antigen by targeting novel fusion proteins to antigen-presenting cells. Mol Ther. 2006; 13(4):776-85.
37. Schjetne K W, Fredriksen A B, Bogen B. Delivery of Antigen to CD40 Induces Protective Immune Responses against Tumorsl. J Immunol. 2007; 178(7):4169-76.
38. Fossum E, Grodeland G, Terhorst D, Tveita A A, Vikse E, Mjaaland S, et al. Vaccine molecules targeting Xcr1 on cross-presenting DCs induce protective CD8+ T-cell responses against influenza virus. Eur J Immunol. 2015; 45(2):624-35.
39. Lovas T O, J C JCB, Øynebraten I, Gundersen K, Bogen B. DNA vaccines: MHC II-targeted vaccine protein produced by transfected muscle fibres induces a local inflammatory cell infiltrate in mice. PLoS One. 2014; 9(10): e108069.
40. Grodeland G, Mjaaland S, Roux K H, Fredriksen A B, Bogen B. DNA vaccine that targets hemagglutinin to MHC class II molecules rapidly induces antibody-mediated protection against influenza. J Immunol. 2013; 191 (6):12.
41. Chang H C, Bao Z, Yao Y, Tse A G, Goyarts E C, Madsen M, et al. A general method for facilitating heterodimeric pairing between two proteins: application to expression of alpha and beta T-cell receptor extracellular segments. Proc Natl Acad Sci USA. 1994; 91(24):11408-12.

We claim:

1. A DNA vaccine comprising first and second nucleic acid constructs encoding first and second fusion proteins comprising a targeting unit, a heterodimerization unit, and an antigenic unit in operable association, wherein said antigenic unit for each of said first and second fusion proteins are variant target antigenic proteins and wherein when said first and second nucleic acid constructs are introduced into a cell the first and second fusion proteins are expressed and associate to form a first heterodimeric protein via association of said heterodimerization units, wherein said heterodimerization unit in one of said first and second nucleic acid constructs is an ACID heterodimerization unit and the heterodimerization unit in the other of the first and second nucleic acid constructs is a BASE heterodimerization unit that interact to form an ACID/BASE heterodimerization domain is said first heterodimeric protein.

2. The DNA vaccine of claim 1, wherein said heterodimerization unit in one of said first and second nucleic acid constructs is a barstar heterodimerization unit and the heterodimerization unit in the other of the first and second nucleic acid constructs is a barnase heterodimerization unit that interact to form a barstar/barnase heterodimerization domain is said first heterodimeric protein.

3. The DNA vaccine of claim 1, wherein said targeting units of said first and second fusion proteins are identical.

4. The DNA vaccine of claim 1, wherein said targeting units of said first and second fusion proteins are different.

5. The DNA vaccine of claim 1, wherein said targeting unit is an antigen binding protein.

6. The DNA vaccine of claim 5, wherein said antigen binding protein is a scFv.

7. The DNA vaccine of claim 1, wherein said targeting unit is an Antigen Presenting Cell (APC) targeting unit.

8. The DNA vaccine of claim 7, wherein said APC targeting unit binds to a target selected from the group consisting of MHC-II molecules, CD40, CD11c, CD14, HLA-DP, Toll-like receptors, and chemokine receptors.

9. The DNA vaccine of claim 1, wherein said variant antigenic target proteins have greater than about 30%, 40%, 50%, 60%, 70%, 80%, 90% or 95% sequence identity or conserved regions of more than 8, 10, 12, 15, 20, 30, 40, 50 or 60 amino acids in length and up to 100 to 200 amino acids in length within the variant antigenic target proteins have greater than about 30%, 40%, 50%, 60%, 70%, 80%, 90% or 95% sequence identity.

10. The DNA vaccine of claim 1, where said different variant antigenic target proteins are from different strains or serotypes of an organism.

11. The DNA vaccine of claim 10, wherein said organism is a pathogenic organism.

12. The DNA vaccine of claim 1, wherein said different variant antigenic target proteins are variants of hemagglutinin (HA).

13. The DNA vaccine of claim 12, wherein said vaccine comprises variants of HA from at least three, four, five or six and up to 12 or 18 strains or serotypes of influenza viruses.

14. The DNA vaccine of claim 13, wherein said influenza viruses are selected from the group consisting of group 1 and group 2 influenza viruses.

15. The DNA vaccine of claim 14, wherein said group 1 influenza viruses are selected from the group consisting of H1, H2, H5, H6, H8, H9, H11, H12, H13, H16, H17 and H18 and said group 2 influenza viruses are selected from the group consisting of H3, H4, H7, H10, H14 and H15.

16. The DNA vaccine of claim 1, wherein said different variant antigenic target proteins are variants of a cancer antigen or neo-epitope.

17. The DNA vaccine of claim 1, further comprising at least third and fourth nucleic acid constructs encoding third and fourth fusion proteins comprising a targeting unit, a heterodimerization domain, and an antigenic unit in operable association, wherein said antigenic unit for each of said third and fourth fusion proteins are variant target antigenic proteins.

18. The DNA vaccine of claim 17, wherein expression of said third and fourth fusion proteins in a cell with said first and second fusion proteins results in the production of a mixture of heterodimeric proteins.

19. The DNA vaccine of claim 1, wherein when said first and second nucleic acid constructs are expressed in a cell, the production of said heterodimeric proteins is characterized by the substantial absence of the production of homodimeric proteins comprising the same target antigenic protein.

20. The DNA vaccine of claim 18, wherein when said first and second nucleic acid constructs and said at least third and fourth nucleic acid constructs are expressed in a cell, the production of said heterodimeric proteins is characterized by the substantial absence of the production of homodimeric proteins comprising the same target antigenic protein.

21. The DNA vaccine of claim 1, wherein the sequence encoding the fusion protein is operably linked to a promoter.

22. A vaccine composition comprising a heterodimeric protein molecule, wherein said heterodimeric protein molecule comprises first and second fusion protein monomers comprising a targeting unit, a heterodimerization unit, and an antigenic unit in operable association, wherein said antigenic unit for each of said first and second fusion protein monomers differ by encoding different variant target antigenic proteins, and wherein said heterodimeric protein molecule comprises two of said monomers joined by association of said dimerization domains, wherein said heterodimerization unit in one of said first and second nucleic acid constructs is an ACID heterodimerization unit and the heterodimerization unit in the other of the first and second nucleic acid constructs is a BASE heterodimerization unit that interact to form an ACID/BASE heterodimerization domain is said first heterodimeric protein.

* * * * *

SEQUENCE LISTING

<160> NUMBER OF SEQ ID NOS: 13

<210> SEQ ID NO 1
<211> LENGTH: 1800
<212> TYPE: DNA
<213> ORGANISM: Artificial sequence
<220> FEATURE:
<223> OTHER INFORMATION: synthetic

<400> SEQUENCE: 1

```
gggtgacaat gacatccact ttgcctttct ctccacaggt gtgcattccg cgccatatgg      60
agctgacacc ccgactgcct gctgcttctc ctacagccgg aagattccac gccaattcat     120
cgttgactat tttgaaacca gcagcctttg ctcccagcca ggtgtcattt tcctgactaa     180
gagaaaccgg cagatctgcg ctgactccaa agagacctgg gtccaagaat acatcactga     240
cctggaactg aacgctggtg agtcgtacgc tagcaagctt ggccagcgca gggagggagg     300
gtgtctgctg gaagccaggc tcagccctcc tgcctggacg catcccggct gtgcagtccc     360
agcccagggc accaaggcag gccccgtctg actcctcacc cggaggcctc tgcccgcccc     420
actcatgctc agggagaggg tcttctggct ttttccacca ggctccgggc aggcacaggc     480
tggatgcccc taccccaggc ccttcacaca caggggcagg tgctgcgctc agagctgcca     540
aaagccatat ccaggaggac cctgcccctg acctaagccc accccaaagg ccaaactctc     600
tactcactca gctcagacac cttctctctt cccagatctg agtaactccc aatcttctct     660
ctgcagagct caaaacccca cttggtgaca caactcacac atgcccacgg tgcccaggag     720
gtagcagcgg tggaaaattc ggcggttcca ctacagctcc atcagctcag ctcgaaaaag     780
agctccaggc cctggagaag gaaaatgcac agctggaatg ggagttgcaa gcactggaaa     840
aggaactggc tcagggaggt ggtagcggag ggttaaccaa attcggcggt tccactacag     900
ctccatcagc tcagctcgaa aaagagctcc aggccctgga aggaaaat gcacagctgg     960
aatgggagtt gcaagcactg gaaaaggaac tggctcaggg aggtggtagc ggagggttaa    1020
ccggcctcag cggcctggat gtacagcttc aggagtcagg acctggcctc gtgaaacctt    1080
ctcagtctct gtctctcacc tgctctgtca ctggctactc catcaccagt gggtatttct    1140
ggaactggat acggcagttt ccaggaaaca aactggaatg gttgggcttc ataaagtacg    1200
acggtagcaa tggctacaat ccatctctca aaaatcgagt ttccatcact cgtgacacat    1260
ctgagaacca gttttttcctg aagttgaatt ctgtgactac tgaggacaca gctacatatt    1320
actgtgccgg agataatgat cacctctact actttgacta ctggggccaa ggcaccactc    1380
tcacagtctc ctcaggtgga ggcggatctg gcggaggtgg ctctggcggt ggcggatcgc    1440
aggctgttgt gactcaggaa tctgcactca ccacatcacc tggtggaaca gtcatactca    1500
cttgtcgctc aagtactggg gctgttacaa ctagtaacta tgccaactgg atacaagaaa    1560
aaccagatca tttattcact ggtctaatcg gtggtaccag caaccgagct ccaggtgttc    1620
ctgtcagatt ctcaggctcc ctgattggag acaaggctgc cctcaccatc acaggggcac    1680
agactgagga tgatgcaatg tatttctgtg ctctatggtt cagaaaccat tttgttttcg    1740
gcggtggaac caaggtcact gtcctatgag gcctgcaggg ccggtccgtc gactctagag    1800
```

<210> SEQ ID NO 2
<211> LENGTH: 1331
<212> TYPE: DNA
<213> ORGANISM: Artificial sequence
<220> FEATURE:
<223> OTHER INFORMATION: synthetic

<400> SEQUENCE: 2

```
ctccacaggt gtgcattccg cgccatatgg agctgacacc ccgactgcct gctgcttctc    60
ctacagccgg aagattccac gccaattcat cgttgactat tttgaaacca gcagcctttg   120
ctcccagcca ggtgtcattt tcctgactaa gagaaaccgg cagatctgcg ctgactccaa   180
agagacctgg gtccaagaat acatcactga cctggaactg aacgctgagc tcaaaacccc   240
acttggtgac acaactcaca catgcccacg gtgcccagga ggtagcagcg gtggaaaatt   300
cggcggttcc actacagctc catcagctca gctcgaaaaa gagctccagg ccctggagaa   360
ggaaaatgca cagctggaat gggagttgca agcactggaa aaggaactgg ctcagggagg   420
tggtagcgga gggttaacca aattcggcgg ttccactaca gctccatcag ctcagctcga   480
aaaagagctc caggccctgg agaaggaaaa tgcacagctg gaatgggagt tgcaagcact   540
ggaaaaggaa ctggctcagg gaggtggtag cggagggtta accggcctca gcggcctgga   600
tgtacagctt caggagtcag gacctggcct cgtgaaacct tctcagtctc tgtctctcac   660
ctgctctgtc actggctact ccatcaccag tgggtatttc tggaactgga tacggcagtt   720
tccaggaaac aaactggaat ggttgggctt cataaagtac gacggtagca atggctacaa   780
tccatctctc aaaaatcgag tttccatcac tcgtgacaca tctgagaacc agttttttcct   840
gaagttgaat tctgtgacta ctgaggacac agctacatat tactgtgccg agataatga   900
tcacctctac tactttgact actggggcca aggcaccact ctcacagtct cctcaggtgg   960
aggcggatct ggcggaggtg gctctggcgg tggcggatcg caggctgttg tgactcagga  1020
atctgcactc accacatcac ctggtggaac agtcatactc acttgtcgct caagtactgg  1080
ggctgttaca actagtaact atgccaactg gatacaagaa aaaccagatc atttattcac  1140
tggtctaatc ggtggtacca gcaaccgagc tccaggtgtt cctgtcagat ctcaggctc  1200
cctgattgga gacaaggctg ccctcaccat cacaggggca cagactgagg atgatgcaat  1260
gtatttctgt gctctatggt tcagaaacca ttttgttttc ggcggtggaa ccaaggtcac  1320
tgtcctatga g                                                      1331
```

<210> SEQ ID NO 3
<211> LENGTH: 442
<212> TYPE: PRT
<213> ORGANISM: Artificial sequence
<220> FEATURE:
<223> OTHER INFORMATION: synthetic

<400> SEQUENCE: 3

```
Ser Thr Gly Val His Ser Ala Pro Tyr Gly Ala Asp Thr Pro Thr Ala
1               5                   10                  15

Cys Cys Phe Ser Tyr Ser Arg Lys Ile Pro Arg Gln Phe Ile Val Asp
            20                  25                  30

Tyr Phe Glu Thr Ser Ser Leu Cys Ser Gln Pro Gly Val Ile Phe Leu
        35                  40                  45

Thr Lys Arg Asn Arg Gln Ile Cys Ala Asp Ser Lys Glu Thr Trp Val
    50                  55                  60

Gln Glu Tyr Ile Thr Asp Leu Glu Leu Asn Ala Glu Leu Lys Thr Pro
65                  70                  75                  80

Leu Gly Asp Thr Thr His Thr Cys Pro Arg Cys Pro Gly Gly Ser Ser
                85                  90                  95

Gly Gly Lys Phe Gly Gly Ser Thr Thr Ala Pro Ser Ala Gln Leu Glu
            100                 105                 110
```

Lys Glu Leu Gln Ala Leu Glu Lys Glu Asn Ala Gln Leu Glu Trp Glu
    115                 120                 125

Leu Gln Ala Leu Glu Lys Glu Leu Ala Gln Gly Gly Gly Ser Gly Gly
    130                 135                 140

Leu Thr Lys Phe Gly Gly Ser Thr Thr Ala Pro Ser Ala Gln Leu Glu
145                 150                 155                 160

Lys Glu Leu Gln Ala Leu Glu Lys Glu Asn Ala Gln Leu Glu Trp Glu
                165                 170                 175

Leu Gln Ala Leu Glu Lys Glu Leu Ala Gln Gly Gly Gly Ser Gly Gly
        180                 185                 190

Leu Thr Gly Leu Ser Gly Leu Asp Val Gln Leu Gln Glu Ser Gly Pro
        195                 200                 205

Gly Leu Val Lys Pro Ser Gln Ser Leu Ser Leu Thr Cys Ser Val Thr
    210                 215                 220

Gly Tyr Ser Ile Thr Ser Gly Tyr Phe Trp Asn Trp Ile Arg Gln Phe
225                 230                 235                 240

Pro Gly Asn Lys Leu Glu Trp Leu Gly Phe Ile Lys Tyr Asp Gly Ser
                245                 250                 255

Asn Gly Tyr Asn Pro Ser Leu Lys Asn Arg Val Ser Ile Thr Arg Asp
        260                 265                 270

Thr Ser Glu Asn Gln Phe Phe Leu Lys Leu Asn Ser Val Thr Thr Glu
    275                 280                 285

Asp Thr Ala Thr Tyr Tyr Cys Ala Gly Asp Asn Asp His Leu Tyr Tyr
    290                 295                 300

Phe Asp Tyr Trp Gly Gln Gly Thr Thr Leu Thr Val Ser Ser Gly Gly
305                 310                 315                 320

Gly Gly Ser Gly Gly Gly Gly Ser Gly Gly Gly Gly Ser Gln Ala Val
                325                 330                 335

Val Thr Gln Glu Ser Ala Leu Thr Thr Ser Pro Gly Gly Thr Val Ile
        340                 345                 350

Leu Thr Cys Arg Ser Ser Thr Gly Ala Val Thr Thr Ser Asn Tyr Ala
    355                 360                 365

Asn Trp Ile Gln Glu Lys Pro Asp His Leu Phe Thr Gly Leu Ile Gly
    370                 375                 380

Gly Thr Ser Asn Arg Ala Pro Gly Val Pro Val Arg Phe Ser Gly Ser
385                 390                 395                 400

Leu Ile Gly Asp Lys Ala Ala Leu Thr Ile Thr Gly Ala Gln Thr Glu
                405                 410                 415

Asp Asp Ala Met Tyr Phe Cys Ala Leu Trp Phe Arg Asn His Phe Val
        420                 425                 430

Phe Gly Gly Gly Thr Lys Val Thr Val Leu
    435                 440

<210> SEQ ID NO 4
<211> LENGTH: 1800
<212> TYPE: DNA
<213> ORGANISM: Artificial sequence
<220> FEATURE:
<223> OTHER INFORMATION: synthetic

<400> SEQUENCE: 4
gggtgacaat gacatccact ttgcctttct ctccacaggt gtgcattccg cgccatatgg    60
agctgacacc ccgactgcct gctgcttctc ctacagccgg aagattccac gccaattcat   120
cgttgactat tttgaaacca gcagcctttg ctcccagcca ggtgtcattt tcctgactaa   180

```
gagaaaccgg cagatctgcg ctgactccaa agagacctgg gtccaagaat acatcactga      240
cctggaactg aacgctggtg agtcgtacgc tagcaagctt ggccagcgca gggagggagg      300
gtgtctgctg gaagccaggc tcagccctcc tgcctggacg catcccggct gtgcagtccc      360
agcccagggc accaaggcag gccccgtctg actcctcacc cggaggcctc tgcccgcccc      420
actcatgctc agggagaggg tcttctggct ttttccacca ggctccgggc aggcacaggc      480 tggatgccc taccccaggc ccttcacaca caggggcagg tgctgcgctc agagctgcca      540
aaagccatat ccaggaggac cctgcccctg acctaagccc accccaaagg ccaaactctc      600
tactcactca gctcagacac cttctctctt cccagatctg agtaactccc aatcttctct      660
ctgcagagct caaaacccca cttggtgaca caactcacac atgcccacgg tgcccaggag      720 gtagcagcg tggaaaattc ggcggttcca ctacagctcc atcagctcag ttgaaaaga      780 aattgcaagc actgaagaaa aagaacgctc agctgaagtg gaaacttcaa gccctcaaga      840
agaaactcgc ccagggaggt ggtagcgag ggttaaccaa attcggcggt tccactacag      900
ctccatcagc tcagttgaaa agaaattgc aagcactgaa gaaaagaac gctcagctga      960 agtggaaact tcaagccctc aagaagaaac tcgcccaggg aggtggtagc ggagggttaa     1020
ccggcctcag cggcctggat gtacagcttc aggagtcagg acctggcctc gtgaaacctt     1080
ctcagtctct gtctctcacc tgctctgtca ctggctactc catcaccagt gggtatttct     1140
ggaactggat acggcagttt ccaggaaaca aactggaatg gttgggcttc ataaagtacg     1200
acggtagcaa tggctacaat ccatctctca aaaatcgagt ttccatcact cgtgacacat     1260
ctgagaacca gttttttcctg aagttgaatt ctgtgactac tgaggacaca gctacatatt     1320
actgtgccgg agataatgat cacctctact actttgacta ctggggccaa ggcaccactc     1380
tcacagtctc ctcaggtgga ggcggatctg gcggaggtgg ctctggcggt ggcggatcgc     1440
aggctgttgt gactcaggaa tctgcactca ccacatcacc tggtggaaca gtcatactca     1500
cttgtcgctc aagtactggg gctgttacaa ctagtaacta tgccaactgg atacaagaaa     1560
aaccagatca tttattcact ggtctaatcg gtggtaccag caaccgagct ccaggtgttc     1620
ctgtcagatt ctcaggctcc ctgattggag acaaggctgc cctcaccatc acaggggcac     1680
agactgagga tgatgcaatg tatttctgtg ctctatggtt cagaaaccat tttgttttcg     1740
gcggtggaac caaggtcact gtcctatgag gcctgcaggg ccggtccgtc gactctagag     1800
```

<210> SEQ ID NO 5
<211> LENGTH: 1321
<212> TYPE: DNA
<213> ORGANISM: Artificial sequence
<220> FEATURE:
<223> OTHER INFORMATION: synthetic

<400> SEQUENCE: 5

```
gtgcattccg cgcccatatgg agctgacacc ccgactgcct gctgcttctc ctacagccgg       60
aagattccac gccaattcat cgttgactat tttgaaacca gcagcctttg ctcccagcca      120
ggtgtcattt tcctgactaa gagaaaccgg cagatctgcg ctgactccaa agagacctgg      180
gtccaagaat acatcactga cctggaactg aacgctgagc tcaaaacccc acttggtgac      240
acaactcaca catgcccacg gtgcccagga ggtagcagcg tggaaaatt cggcggttcc      300 actacagctc catcagctca gttgaaaaag aaattgcaag cactgaagaa aaagaacgct      360
cagctgaagt ggaaacttca agccctcaag aagaaactcg cccagggagg tggtagcgga      420
```

-continued

```
gggttaacca aattcggcgg ttccactaca gctccatcag ctcagttgaa aaagaaattg    480
caagcactga agaaaaagaa cgctcagctg aagtggaaac ttcaagccct caagaagaaa    540
ctcgcccagg gaggtggtag cggagggtta accggcctca gcggcctgga tgtacagctt    600
caggagtcag gacctggcct cgtgaaacct tctcagtctc tgtctctcac ctgctctgtc    660
actggctact ccatcaccag tgggtatttc tggaactgga tacggcagtt tccaggaaac    720
aaactggaat ggttgggctt cataaagtac gacggtagca atggctacaa tccatctctc    780
aaaaatcgag tttccatcac tcgtgacaca tctgagaacc agttttttcct gaagttgaat    840
tctgtgacta ctgaggacac agctacatat tactgtgccg agataatga tcacctctac     900
tactttgact actggggcca aggcaccact ctcacagtct cctcaggtgg aggcggatct    960
ggcggaggtg gctctggcgg tggcggatcg caggctgttg tgactcagga atctgcactc   1020
accacatcac ctggtggaac agtcatactc acttgtcgct caagtactgg ggctgttaca   1080
actagtaact atgccaactg gatacaagaa aaaccagatc atttattcac tggtctaatc   1140
ggtggtacca gcaaccgagc tccaggtgtt cctgtcagat tctcaggctc cctgattgga   1200
gacaaggctg ccctcaccat cacaggggca cagactgagg atgatgcaat gtatttctgt   1260
gctctatggt tcagaaacca ttttgttttc ggcggtggaa ccaaggtcac tgtcctatga   1320
g                                                                   1321
```

<210> SEQ ID NO 6
<211> LENGTH: 439
<212> TYPE: PRT
<213> ORGANISM: Artificial sequence
<220> FEATURE:
<223> OTHER INFORMATION: synthetic

<400> SEQUENCE: 6

```
Val His Ser Ala Pro Tyr Gly Ala Asp Thr Pro Thr Ala Cys Cys Phe
1               5                   10                  15

Ser Tyr Ser Arg Lys Ile Pro Arg Gln Phe Ile Val Asp Tyr Phe Glu
            20                  25                  30

Thr Ser Ser Leu Cys Ser Gln Pro Gly Val Ile Phe Leu Thr Lys Arg
        35                  40                  45

Asn Arg Gln Ile Cys Ala Asp Ser Lys Glu Thr Trp Val Gln Glu Tyr
    50                  55                  60

Ile Thr Asp Leu Glu Leu Asn Ala Glu Leu Lys Thr Pro Leu Gly Asp
65                  70                  75                  80

Thr Thr His Thr Cys Pro Arg Cys Pro Gly Gly Ser Ser Gly Gly Lys
                85                  90                  95

Phe Gly Gly Ser Thr Thr Ala Pro Ser Ala Gln Leu Lys Lys Lys Leu
            100                 105                 110

Gln Ala Leu Lys Lys Lys Asn Ala Gln Leu Lys Trp Lys Leu Gln Ala
        115                 120                 125

Leu Lys Lys Lys Leu Ala Gln Gly Gly Gly Ser Gly Gly Leu Thr Lys
    130                 135                 140

Phe Gly Gly Ser Thr Thr Ala Pro Ser Ala Gln Leu Lys Lys Lys Leu
145                 150                 155                 160

Gln Ala Leu Lys Lys Lys Asn Ala Gln Leu Lys Trp Lys Leu Gln Ala
                165                 170                 175

Leu Lys Lys Lys Leu Ala Gln Gly Gly Gly Ser Gly Gly Leu Thr Gly
            180                 185                 190

Leu Ser Gly Leu Asp Val Gln Leu Gln Glu Ser Gly Pro Gly Leu Val
```

```
                195                 200                 205
Lys Pro Ser Gln Ser Leu Ser Leu Thr Cys Ser Val Thr Gly Tyr Ser
            210                 215                 220
Ile Thr Ser Gly Tyr Phe Trp Asn Trp Ile Arg Gln Phe Pro Gly Asn
225                 230                 235                 240
Lys Leu Glu Trp Leu Gly Phe Ile Lys Tyr Asp Gly Ser Asn Gly Tyr
                245                 250                 255
Asn Pro Ser Leu Lys Asn Arg Val Ser Ile Thr Arg Asp Thr Ser Glu
            260                 265                 270
Asn Gln Phe Phe Leu Lys Leu Asn Ser Val Thr Thr Glu Asp Thr Ala
        275                 280                 285
Thr Tyr Tyr Cys Ala Gly Asp Asn Asp His Leu Tyr Tyr Phe Asp Tyr
    290                 295                 300
Trp Gly Gln Gly Thr Thr Leu Thr Val Ser Ser Gly Gly Gly Gly Ser
305                 310                 315                 320
Gly Gly Gly Gly Ser Gly Gly Gly Ser Gln Ala Val Val Thr Gln
                325                 330                 335
Glu Ser Ala Leu Thr Thr Ser Pro Gly Gly Thr Val Ile Leu Thr Cys
            340                 345                 350
Arg Ser Ser Thr Gly Ala Val Thr Thr Ser Asn Tyr Ala Asn Trp Ile
        355                 360                 365
Gln Glu Lys Pro Asp His Leu Phe Thr Gly Leu Ile Gly Gly Thr Ser
    370                 375                 380
Asn Arg Ala Pro Gly Val Pro Val Arg Phe Ser Gly Ser Leu Ile Gly
385                 390                 395                 400
Asp Lys Ala Ala Leu Thr Ile Thr Gly Ala Gln Thr Glu Asp Asp Ala
                405                 410                 415
Met Tyr Phe Cys Ala Leu Trp Phe Arg Asn His Phe Val Phe Gly Gly
            420                 425                 430
Gly Thr Lys Val Thr Val Leu
            435

<210> SEQ ID NO 7
<211> LENGTH: 242
<212> TYPE: PRT
<213> ORGANISM: Artificial sequence
<220> FEATURE:
<223> OTHER INFORMATION: synthetic

<400> SEQUENCE: 7

Asp Val Gln Leu Gln Glu Ser Gly Pro Gly Leu Val Lys Pro Ser Gln
1               5                   10                  15
Ser Leu Ser Leu Thr Cys Ser Val Thr Gly Tyr Ser Ile Thr Ser Gly
            20                  25                  30
Tyr Phe Trp Asn Trp Ile Arg Gln Phe Pro Gly Asn Lys Leu Glu Trp
        35                  40                  45
Leu Gly Phe Ile Lys Tyr Asp Gly Ser Asn Gly Tyr Asn Pro Ser Leu
    50                  55                  60
Lys Asn Arg Val Ser Ile Thr Arg Asp Thr Ser Glu Asn Gln Phe Phe
65                  70                  75                  80
Leu Lys Leu Asn Val Thr Thr Glu Asp Thr Ala Thr Tyr Tyr Cys Ala
                85                  90                  95
Gly Asp Asn Asp His Leu Tyr Tyr Phe Asp Tyr Trp Gly Gln Gly Thr
            100                 105                 110
Thr Leu Thr Val Ser Ser Gly Gly Gly Gly Ser Gly Gly Gly Gly Ser
```

```
                115                 120                 125
Gly Gly Gly Gly Ser Gln Ala Val Val Thr Gln Glu Ser Ala Leu Thr
            130                 135                 140

Thr Ser Pro Gly Gly Thr Val Ile Leu Thr Cys Arg Ser Ser Thr Gly
145                 150                 155                 160

Ala Val Thr Thr Ser Asn Tyr Ala Asn Trp Ile Gln Glu Lys Pro Asp
                165                 170                 175

His Leu Phe Thr Gly Leu Ile Gly Gly Thr Ser Asn Arg Ala Pro Gly
            180                 185                 190

Val Pro Val Arg Phe Ser Gly Ser Leu Ile Gly Asp Lys Ala Ala Leu
        195                 200                 205

Thr Ile Thr Gly Ala Gln Thr Glu Asp Asp Ala Met Tyr Phe Cys Ala
    210                 215                 220

Leu Trp Phe Arg Asn His Phe Val Phe Gly Gly Gly Thr Lys Val Thr
225                 230                 235                 240

Val Leu
```

<210> SEQ ID NO 8
<211> LENGTH: 733
<212> TYPE: DNA
<213> ORGANISM: Artificial sequence
<220> FEATURE:
<223> OTHER INFORMATION: synthetic

<400> SEQUENCE: 8

```
gatgtacagc ttcaggagtc aggacctggc ctcgtgaaac cttctcagtc tctgtctctc    60
acctgctctg tcactggcta ctccatcacc agtgggtatt tctggaactg gatacggcag   120
tttccaggaa acaaactgga atggttgggc ttcataaaat acgacggtag caatggctac   180
aatccatctc tcaaaaatcg agtttccatc actcgtgaca catctgagaa ccagttttc    240 ctgaagttga attctgtgac tactgaggac acagctacat attactgtgc cggagataat   300
gatcacctct actctttga ctactggggc caaggcacca ctctcacagt ctcctcaggt    360
ggaggcggat ctggcggagg tggctctggc ggtggcggat cgcaggctgt tgtgactcag   420
gaatctgcac tcaccacatc acctggtgga acagtcatac tcacttgtcg ctcaagtact   480
ggggctgtta caactagtaa ctatgccaac tggatacaag aaaaaccaga tcatttattc   540
actggtctaa tcggtggtac cagcaaccga gctccaggtg ttcctgtcag attctcaggc   600
tccctgattg gagacaaggc tgccctcacc atcacagggg cacagactga ggatgatgca   660
atgtatttct gtgctctatg gttcagaaac cattttgttt tcggcggtgg aaccaaggtc   720
actgtcctat gag                                                      733
```

<210> SEQ ID NO 9
<211> LENGTH: 850
<212> TYPE: DNA
<213> ORGANISM: Artificial sequence
<220> FEATURE:
<223> OTHER INFORMATION: synthetic

<400> SEQUENCE: 9

```
acgcagaaga gcctctccct gtctccgggt aaaggcctcg gtggcctgat ggtccaactg    60
cagcagtcag ggcctgacct tgtgaaacct gggatgtccg tgaaactgtc ctgtaagact   120
ttgggttaca atttctccga caagtggatt cactggatta acagaagcc tggccgaggc   180 cttgaatggg ttggaaggat tgatcctcct aacggtgata ctgactataa tgcggacttc   240
```

```
aagaccccgg ccacactaac tgttgacaga ccctccaaca cagcctactt agaactcaac    300
aacctgacat ctggggactc tgcggtctat tattgttcaa tatcgggtga ttattccgcc    360
tgcgactatt ggggccaagg taccgaactc acagtctcct caggtggagg tggctctggc    420
ggtggcggat cggaggagg cggttctgat gttgtgatga cgcagactcc actctccctg    480
gccgtcagtc ttggagatca cgtgaaaatg tcttgtagat gtaatcagag ccttgtaaac    540
agtcatggag actcctttt acactggttt ctgcagaagc caggccagtc tccaaaactc    600
ctgatctaca aggtttccag ccgatttttt ggggtcccag agaggttcag tggcagtggt    660
tcagggacag atttcacact cgagatcagt cgagtggagg ctgaggatct gggaatttat    720
ttctgttctc aaggtgcaca tgttccgtgg acgttcggtg gaggcacaaa gctggaagtc    780
aaatgaggcc tgcagggccg gtccgtcgac tctagaggat ccactagtaa cggccgccag    840
tgtgctggaa                                                           850
```

<210> SEQ ID NO 10
<211> LENGTH: 261
<212> TYPE: PRT
<213> ORGANISM: Artificial sequence
<220> FEATURE:
<223> OTHER INFORMATION: synthetic

<400> SEQUENCE: 10

```
Thr Gln Lys Ser Leu Ser Leu Ser Pro Gly Lys Gly Leu Gly Gly Leu
1               5                   10                  15

Met Val Gln Leu Gln Gln Ser Gly Pro Asp Leu Val Lys Pro Gly Met
            20                  25                  30

Ser Val Lys Leu Ser Cys Lys Thr Leu Gly Tyr Asn Phe Ser Asp Lys
        35                  40                  45

Trp Ile His Trp Ile Lys Gln Lys Pro Gly Arg Gly Leu Glu Trp Val
    50                  55                  60

Gly Arg Ile Asp Pro Ser Asn Gly Asp Thr Asp Tyr Asn Ala Asp Phe
65                  70                  75                  80

Lys Thr Pro Ala Thr Leu Thr Val Asp Arg Pro Ser Asn Thr Ala Tyr
                85                  90                  95

Leu Glu Leu Asn Asn Leu Thr Ser Gly Asp Ser Ala Val Tyr Tyr Cys
            100                 105                 110

Ser Ile Ser Gly Asp Tyr Ser Ala Cys Asp Tyr Trp Gly Gln Gly Thr
        115                 120                 125

Glu Leu Thr Val Ser Ser Gly Gly Gly Ser Gly Gly Gly Gly Ser
    130                 135                 140

Gly Gly Gly Gly Ser Asp Val Val Met Thr Gln Thr Pro Leu Ser Leu
145                 150                 155                 160

Ala Val Ser Leu Gly Asp His Val Lys Met Ser Cys Arg Cys Asn Gln
                165                 170                 175

Ser Leu Val Asn Ser His Gly Asp Ser Phe Leu His Trp Phe Leu Gln
            180                 185                 190

Lys Pro Gly Gln Ser Pro Lys Leu Leu Ile Tyr Lys Val Ser Ser Arg
        195                 200                 205

Phe Phe Gly Val Pro Glu Arg Phe Ser Gly Ser Gly Ser Gly Thr Asp
    210                 215                 220

Phe Thr Leu Glu Ile Ser Arg Val Glu Ala Glu Asp Leu Gly Ile Tyr
225                 230                 235                 240

Phe Cys Ser Gln Gly Ala His Val Pro Trp Thr Phe Gly Gly Gly Thr
                245                 250                 255
```

Lys Leu Glu Val Lys
            260

<210> SEQ ID NO 11
<211> LENGTH: 245
<212> TYPE: PRT
<213> ORGANISM: Artificial sequence
<220> FEATURE:
<223> OTHER INFORMATION: synthetic

<400> SEQUENCE: 11

Met Val Gln Leu Gln Gln Ser Gly Pro Asp Leu Val Lys Pro Gly Met
1               5                   10                  15

Ser Val Lys Leu Ser Cys Lys Thr Leu Gly Tyr Asn Phe Ser Asp Lys
            20                  25                  30

Trp Ile His Trp Ile Lys Gln Lys Pro Gly Arg Gly Leu Glu Trp Val
        35                  40                  45

Gly Arg Ile Asp Pro Ser Asn Gly Asp Thr Tyr Asn Ala Asp Phe
    50                  55                  60

Lys Thr Pro Ala Thr Leu Thr Val Asp Arg Pro Ser Asn Thr Ala Tyr
65                  70                  75                  80

Leu Glu Leu Asn Asn Leu Thr Ser Gly Asp Ser Ala Val Tyr Tyr Cys
                85                  90                  95

Ser Ile Ser Gly Asp Tyr Ser Ala Cys Asp Tyr Trp Gly Gln Gly Thr
            100                 105                 110

Glu Leu Thr Val Ser Ser Gly Gly Gly Ser Gly Gly Gly Gly Ser
        115                 120                 125

Gly Gly Gly Gly Ser Asp Val Val Met Thr Gln Thr Pro Leu Ser Leu
    130                 135                 140

Ala Val Ser Leu Gly Asp His Val Lys Met Ser Cys Arg Cys Asn Gln
145                 150                 155                 160

Ser Leu Val Asn Ser His Gly Asp Ser Phe Leu His Trp Phe Leu Gln
                165                 170                 175

Lys Pro Gly Gln Ser Pro Lys Leu Leu Ile Tyr Lys Val Ser Ser Arg
            180                 185                 190

Phe Phe Gly Val Pro Glu Arg Phe Ser Gly Ser Gly Ser Gly Thr Asp
        195                 200                 205

Phe Thr Leu Glu Ile Ser Arg Val Glu Ala Glu Asp Leu Gly Ile Tyr
    210                 215                 220

Phe Cys Ser Gln Gly Ala His Val Pro Trp Thr Phe Gly Gly Gly Thr
225                 230                 235                 240

Lys Leu Glu Val Lys
            245

<210> SEQ ID NO 12
<211> LENGTH: 523
<212> TYPE: PRT
<213> ORGANISM: Artificial sequence
<220> FEATURE:
<223> OTHER INFORMATION: synthetic

<400> SEQUENCE: 12

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala

```
            35                  40                  45
Pro Leu Gln Leu Gly Lys Cys Asn Ile Ala Gly Trp Leu Leu Gly Asn
 50                  55                  60

Pro Glu Cys Asp Pro Leu Leu Pro Val Arg Ser Trp Ser Tyr Ile Val
 65                  70                  75                  80

Glu Thr Pro Asn Ser Glu Asn Gly Ile Cys Tyr Pro Gly Asp Phe Ile
                     85                  90                  95

Asp Tyr Glu Glu Leu Arg Glu Gln Leu Ser Ser Val Ser Ser Phe Glu
                    100                 105                 110

Arg Phe Glu Ile Phe Pro Lys Glu Ser Ser Trp Pro Asn His Asn Thr
                    115                 120                 125

Asn Gly Val Thr Ala Ala Cys Ser His Glu Gly Lys Ser Ser Phe Tyr
                    130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Lys Gly Lys Glu Val Leu Val Leu Trp
                    165                 170                 175

Gly Ile His His Pro Pro Asn Ser Lys Glu Gln Gln Asn Leu Tyr Gln
                    180                 185                 190

Asn Glu Asn Ala Tyr Val Ser Val Val Thr Ser Asn Tyr Asn Arg Arg
                    195                 200                 205

Phe Thr Pro Glu Ile Ala Glu Arg Pro Lys Val Arg Asp Gln Ala Gly
                    210                 215                 220

Arg Met Asn Tyr Tyr Trp Thr Leu Leu Lys Pro Gly Asp Thr Ile Ile
225                 230                 235                 240

Phe Glu Ala Asn Gly Asn Leu Ile Ala Pro Met Tyr Ala Phe Ala Leu
                    245                 250                 255

Ser Arg Gly Phe Gly Ser Gly Ile Ile Thr Ser Asn Ala Ser Met His
                    260                 265                 270

Glu Cys Asn Thr Lys Cys Gln Thr Pro Leu Gly Ala Ile Asn Ser Ser
                    275                 280                 285

Leu Pro Tyr Gln Asn Ile His Pro Val Thr Ile Gly Glu Cys Pro Lys
                    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                    325                 330                 335

Glu Gly Gly Trp Thr Gly Met Ile Asp Gly Trp Tyr Gly Tyr His His
                    340                 345                 350

Gln Asn Glu Gln Gly Ser Gly Tyr Ala Ala Asp Gln Lys Ser Thr Gln
                    355                 360                 365

Asn Ala Ile Asn Gly Ile Thr Asn Lys Val Asn Ser Val Ile Glu Lys
                    370                 375                 380

Met Asn Ile Gln Phe Thr Ala Val Gly Lys Glu Phe Asn Lys Leu Glu
385                 390                 395                 400

Lys Arg Met Glu Asn Leu Asn Lys Lys Val Asp Asp Gly Phe Leu Asp
                    405                 410                 415

Ile Trp Thr Tyr Asn Ala Glu Leu Leu Val Leu Leu Glu Asn Glu Arg
                    420                 425                 430

Thr Leu Asp Phe His Asp Ser Asn Val Lys Asn Leu Tyr Glu Lys Val
                    435                 440                 445

Lys Ser Gln Leu Lys Asn Asn Ala Lys Glu Ile Gly Asn Gly Cys Phe
450                 455                 460
```

```
Glu Phe Tyr His Lys Cys Asp Asn Glu Cys Met Glu Ser Val Arg Asn
465                 470                 475                 480

Gly Thr Tyr Asp Tyr Pro Lys Tyr Ser Glu Ser Lys Leu Asn Arg
            485                 490                 495

Glu Lys Val Asp Gly Val Lys Leu Glu Ser Met Gly Ile Tyr Gln Ile
            500                 505                 510

Leu Ala Ile Tyr Ser Thr Val Ala Ser Ser Leu
        515                 520

<210> SEQ ID NO 13
<211> LENGTH: 523
<212> TYPE: PRT
<213> ORGANISM: Artificial sequence
<220> FEATURE:
<223> OTHER INFORMATION: synthetic

<400> SEQUENCE: 13

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Trp Ser Tyr Ile Val Glu
65                  70                  75                  80

Thr Ser Ser Ser Asp Asn Gly Thr Cys Tyr Pro Gly Asp Phe Ile Asp
                85                  90                  95

Tyr Glu Glu Leu Arg Glu Gln Leu Ser Ser Val Ser Ser Arg Glu Arg
            100                 105                 110

Phe Glu Ile Phe Pro Lys Thr Ser Ser Trp Pro Asn His Asp Ser Asn
        115                 120                 125

Lys Gly Val Thr Ala Ala Cys Pro His Ala Gly Ala Lys Ser Phe Tyr
    130                 135                 140

Lys Asn Leu Ile Trp Leu Val Lys Lys Gly Asn Ser Tyr Pro Lys Leu
145                 150                 155                 160

Ser Lys Ser Tyr Ile Asn Asp Lys Gly Lys Glu Val Leu Val Leu Trp
                165                 170                 175

Gly Ile His His Pro Ser Thr Ser Ala Asp Gln Gln Ser Leu Tyr Gln
            180                 185                 190

Asn Ala Asp Ala Tyr Val Phe Val Gly Ser Ser Arg Tyr Ser Lys Lys
        195                 200                 205

Phe Lys Pro Glu Ile Ala Ile Arg Pro Lys Val Arg Asp Gln Glu Gly
    210                 215                 220

Arg Met Asn Tyr Tyr Trp Thr Leu Val Glu Pro Gly Asp Lys Ile Thr
225                 230                 235                 240

Phe Glu Ala Thr Gly Asn Leu Val Val Pro Arg Tyr Ala Phe Ala Met
                245                 250                 255

Glu Arg Asn Ala Gly Ser Gly Ile Ile Ile Ser Asp Thr Pro Val His
            260                 265                 270

Asp Cys Asn Thr Thr Cys Gln Thr Pro Lys Ala Gly Ile Asn Thr Ser
        275                 280                 285

Leu Pro Phe Gln Asn Ile His Pro Ile Thr Ile Gly Lys Cys Pro Lys
    290                 295                 300
```

-continued

```
Tyr Val Lys Ser Thr Lys Leu Arg Leu Ala Thr Gly Leu Arg Asn Val
305                 310                 315                 320

Pro Ser Ile Gln Ser Arg Gly Leu Phe Gly Ala Ile Ala Gly Phe Ile
            325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Leu Lys Ser Thr Gln
            355                 360                 365

Asn Ala Ile Asp Glu Ile Thr Asn Lys Val Asn Ser Val Ile Glu Lys
    370                 375                 380

Met Asn Thr Gln Phe Thr Ala Val Gly Lys Glu Phe Asn His Leu Glu
385                 390                 395                 400

Lys Arg Ile Glu Asn Leu Asn Lys Lys Val Asp Asp Gly Phe Leu Asp
            405                 410                 415

Ile Trp Thr Tyr Asn Ala Glu Leu Leu Val Leu Leu Glu Asn Glu Arg
            420                 425                 430

Thr Leu Asp Tyr His Asp Ser Asn Val Lys Asn Leu Tyr Glu Lys Val
            435                 440                 445

Arg Ser Gln Leu Lys Asn Asn Ala Lys Glu Ile Gly Asn Gly Cys Phe
    450                 455                 460

Glu Phe Tyr His Lys Cys Asp Asn Thr Cys Met Glu Ser Val Lys Asn
465                 470                 475                 480

Gly Thr Tyr Asp Tyr Pro Lys Tyr Ser Glu Glu Ala Lys Leu Asn Arg
            485                 490                 495

Glu Glu Ile Asp Gly Val Lys Leu Glu Ser Thr Arg Ile Tyr Gln Ile
            500                 505                 510

Leu Ala Ile Tyr Ser Thr Val Ala Ser Ser Leu
            515                 520
```